(12) United States Patent
Naumenko et al.

(10) Patent No.: US 12,236,603 B2
(45) Date of Patent: Feb. 25, 2025

(54) SYSTEMS AND METHODS FOR IMAGING SAMPLES WITH REDUCED SAMPLE MOTION ARTIFACTS

(71) Applicant: SamanTree Medical SA, Lausanne (CH)

(72) Inventors: Andrey Naumenko, Chavannes-près-Renens (CH); Aurèle Timothée Horisberger, Crissier (CH); Diego Joss, Renens (CH); Frédéric Schmitt, Vulliens (CH); Etienne Shaffer, Pailly (CH); Jonathan Abel Pirolet, Aclens (CH); Bastien Rachet, Lausanne (CH); Andrew Logvinov, Minsk (BY)

(73) Assignee: SamanTree Medical SA, Lausanne (CH)

( * ) Notice: Subject to any disclaimer, the term of this patent is extended or adjusted under 35 U.S.C. 154(b) by 1011 days.

(21) Appl. No.: 17/174,919

(22) Filed: Feb. 12, 2021

(65) Prior Publication Data

US 2021/0248746 A1 Aug. 12, 2021

Related U.S. Application Data

(60) Provisional application No. 62/975,742, filed on Feb. 12, 2020.

(51) Int. Cl.
*G06T 7/00* (2017.01)
*G01N 33/483* (2006.01)
(Continued)

(52) U.S. Cl.
CPC ....... *G06T 7/0016* (2013.01); *G01N 33/4833* (2013.01); *G02B 21/002* (2013.01);
(Continued)

(58) Field of Classification Search
CPC .............. G06T 7/0016; G06T 3/4038; G06T 2207/10056; G06T 2207/30024; G01N 21/6456; G01N 21/0024
See application file for complete search history.

(56) References Cited

U.S. PATENT DOCUMENTS

| 5,889,881 A | 3/1999 | MacAulay et al. |
| 7,812,944 B1 | 10/2010 | Schmidt |

(Continued)

FOREIGN PATENT DOCUMENTS

| DE | 4432304 A1 * | 3/1996 | ............ G01Q 10/06 |
| WO | WO-2004/079405 A2 | 9/2004 | |

(Continued)

OTHER PUBLICATIONS

International Search Report, International Application No. PCT/EP2021/053525, 6 pages, Sep. 13, 2021.

(Continued)

*Primary Examiner* — Kathleen V Nguyen
(74) *Attorney, Agent, or Firm* — Choate, Hall & Stewart LLP; Michael D. Schmitt

(57) ABSTRACT

Systems and methods to identify and/or reduce or eliminate sample motion artifacts are disclosed. Sample motion artifacts may be reduced or eliminated using scan patterns where an acquisition time difference between when perimeter pixels in adjacent tiles are acquired is reduced, as compared to a conventional raster scan to reduce or eliminate discontinuities that would otherwise appear at tile boundaries in an image. In some embodiments, test images acquired using relatively small test scan patterns or intensities of test points acquired at different times may be compared to determine whether sample motion has occurred. In some embodiments, intensity of adjacent pixels at a tile boundary are compared. In some embodiments, intensity of one or more single pixels is monitored over time (Continued)

to determine whether sample motion has occurred over a period of time. In some embodiments, a flattening or reshaping tool may be used to suppress sample motion during imaging.

19 Claims, 44 Drawing Sheets

(51) Int. Cl.
*G02B 21/00* (2006.01)
*G02B 21/36* (2006.01)
*G06T 3/4038* (2024.01)

(52) U.S. Cl.
CPC ....... *G02B 21/0044* (2013.01); *G02B 21/008* (2013.01); *G02B 21/367* (2013.01); *G06T 3/4038* (2013.01); *G06T 7/0012* (2013.01); *G06T 2207/10056* (2013.01); *G06T 2207/30024* (2013.01)

(56) References Cited

U.S. PATENT DOCUMENTS

| | | | |
|---|---|---|---|
| 10,094,784 B2 | 10/2018 | Rachet et al. | |
| 10,539,776 B2 | 1/2020 | Shaffer et al. | |
| 10,928,621 B2 | 2/2021 | Shaffer et al. | |
| 2001/0017649 A1 | 8/2001 | Yaron | |
| 2002/0180865 A1 | 12/2002 | Lee et al. | |
| 2009/0225411 A1 | 9/2009 | Cui et al. | |
| 2011/0101243 A1* | 5/2011 | Wimberger-Friedl | G01N 21/6452 250/459.1 |
| 2015/0381915 A1* | 12/2015 | Mabuchi | H04N 25/772 348/302 |
| 2016/0013016 A1 | 1/2016 | Otten et al. | |
| 2017/0003491 A1 | 1/2017 | Waller et al. | |
| 2019/0137752 A1 | 5/2019 | Shaffer et al. | |
| 2019/0213736 A1 | 7/2019 | Varekamp et al. | |
| 2019/0384184 A1 | 12/2019 | Pandey et al. | |
| 2020/0073022 A1 | 3/2020 | Watanabe et al. | |
| 2020/0284703 A1 | 9/2020 | Shaffer et al. | |
| 2022/0381672 A1 | 12/2022 | Pecker et al. | |
| 2023/0058111 A1 | 2/2023 | Shaffer et al. | |

FOREIGN PATENT DOCUMENTS

| | | |
|---|---|---|
| WO | WO-2009/156942 A1 | 12/2009 |
| WO | WO-2016/156516 A2 | 10/2016 |
| WO | WO-2019/077610 A1 | 4/2019 |
| WO | WO-2021/160843 A2 | 8/2021 |
| WO | WO-2023/012241 A1 | 2/2023 |

OTHER PUBLICATIONS

Written Opinion, International Application No. PCT/EP2021/053525, 12 pages, Sep. 13, 2021.
International Search Report for PCT/EP2022/071873, filed Aug. 3, 2022, 6 pages, (mailed Jan. 26, 2023).
Invitation to Pay Additional Fees for PCT/EP2022/071873, filed Aug. 3, 2022, 11 pages, (mailed Dec. 5, 2022).
Written Opinion for PCT/EP2022/071873, filed Aug. 3, 2022, 11 pages, (mailed Jan. 26, 2023).

* cited by examiner

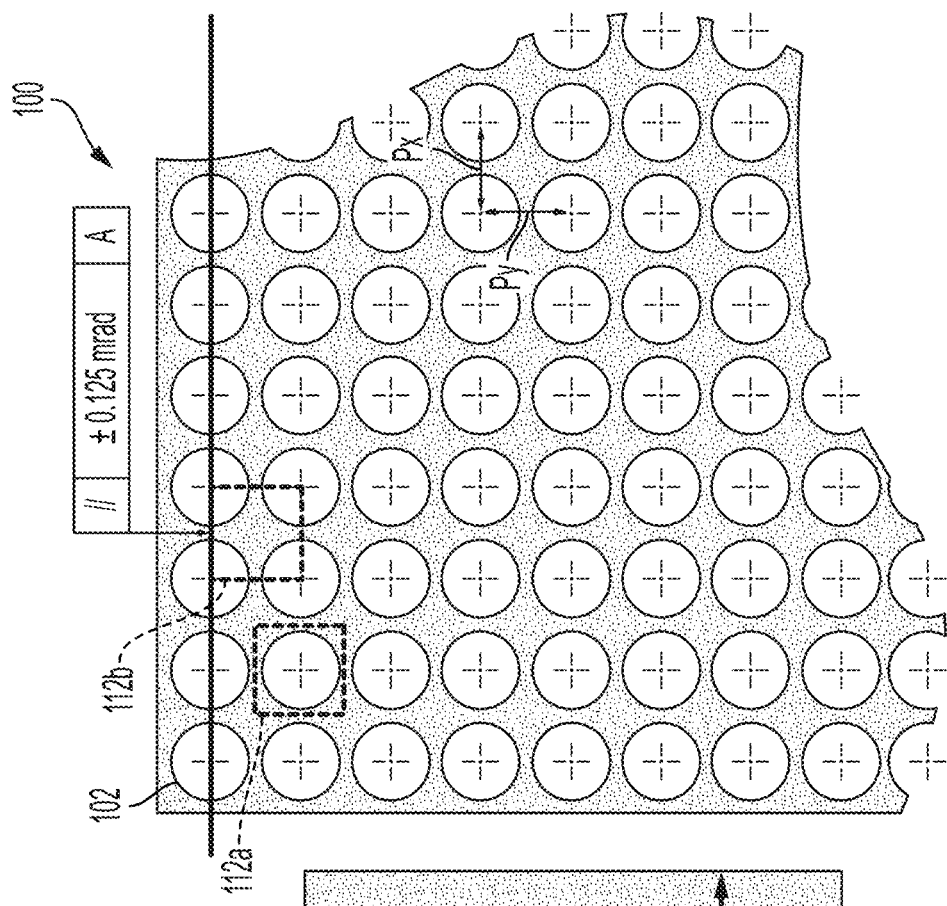
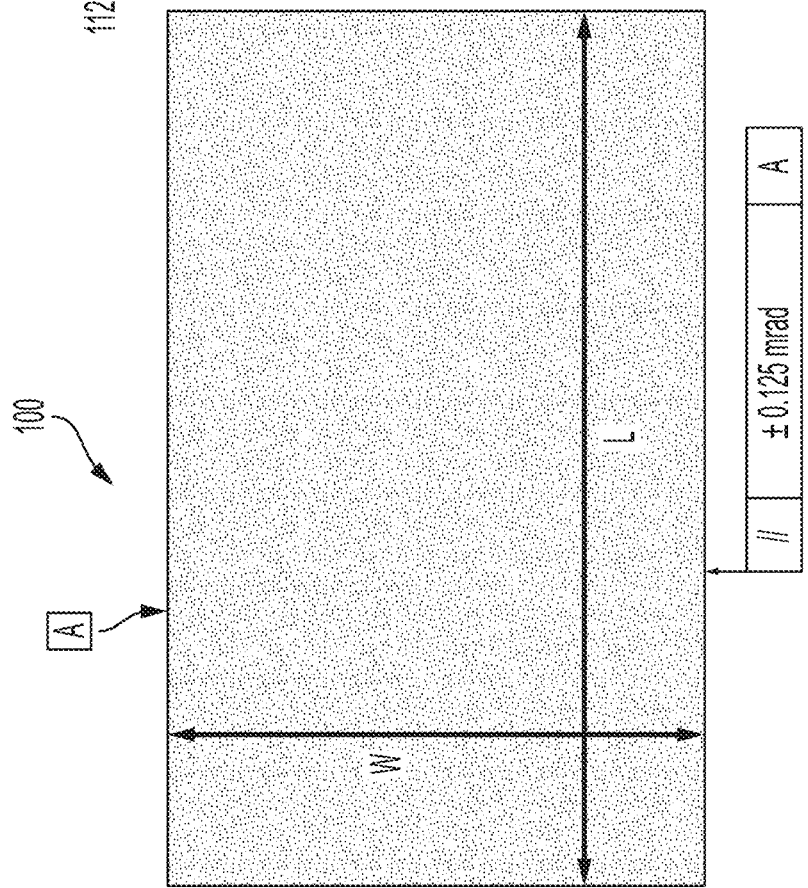
FIG. 1B
FIG. 1A

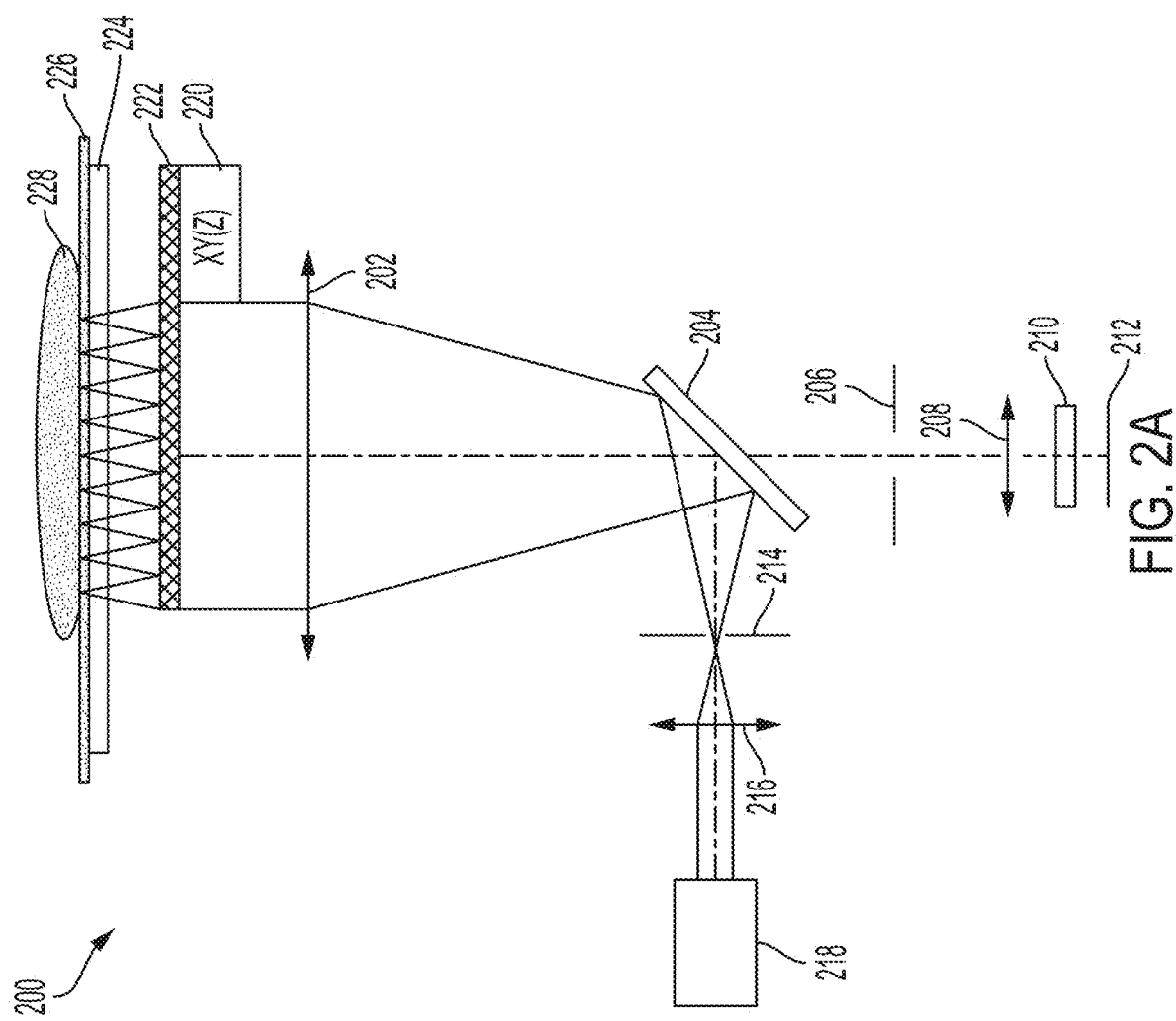

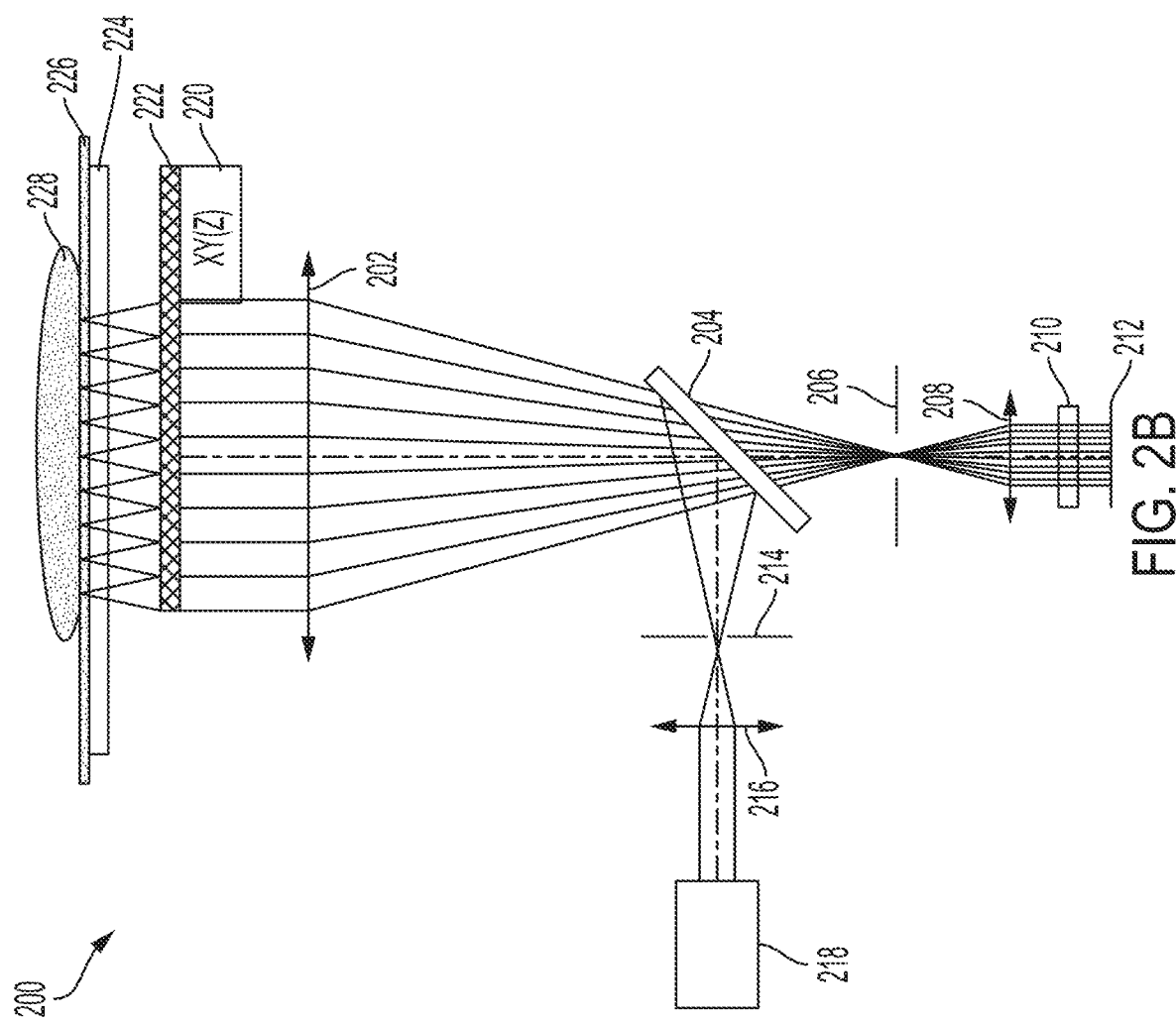

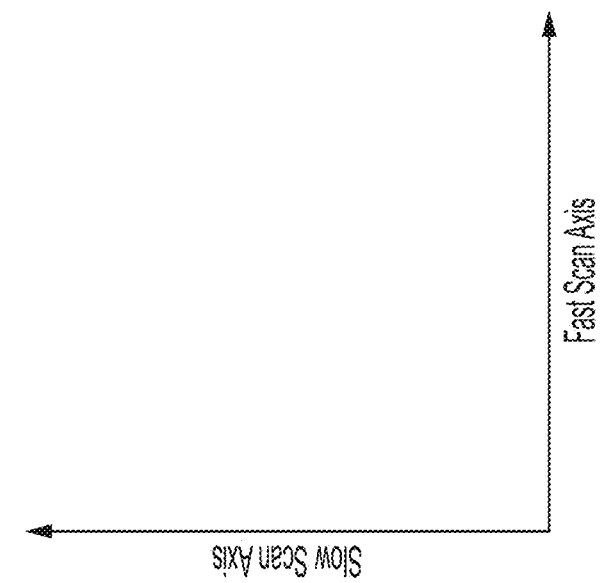
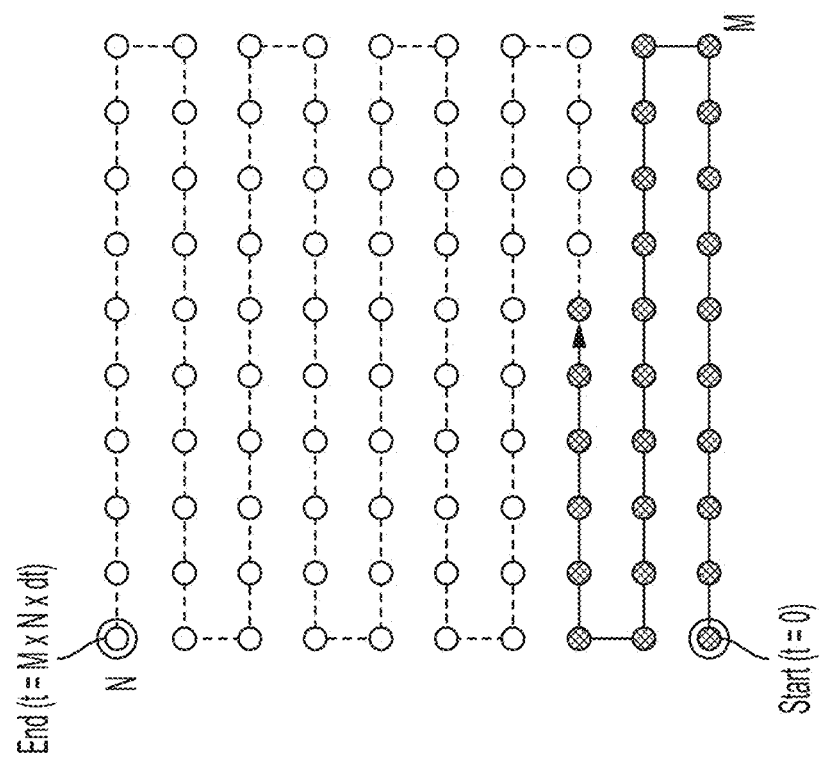
FIG. 3

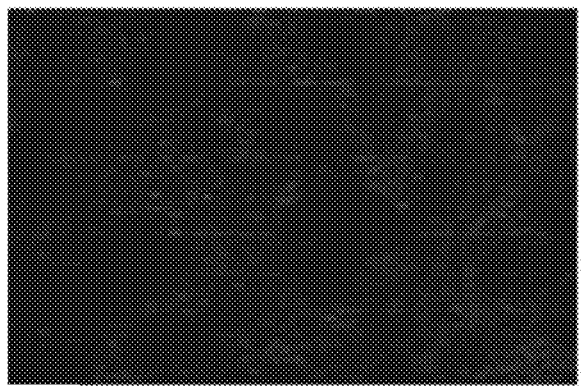
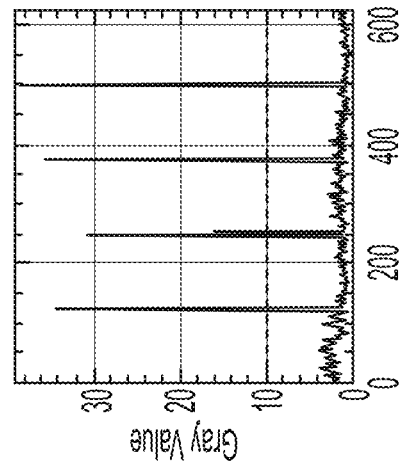
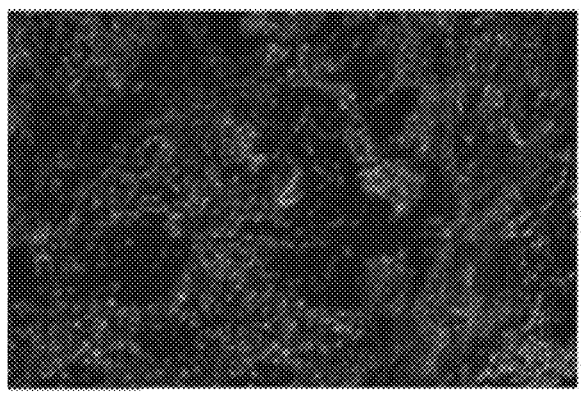
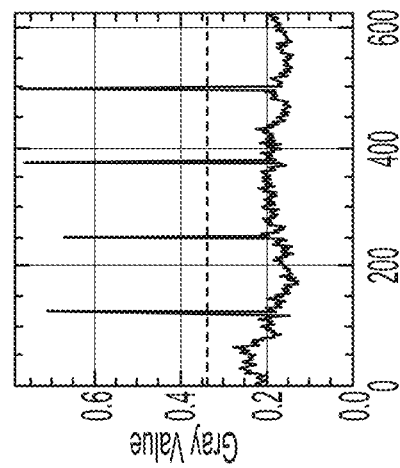
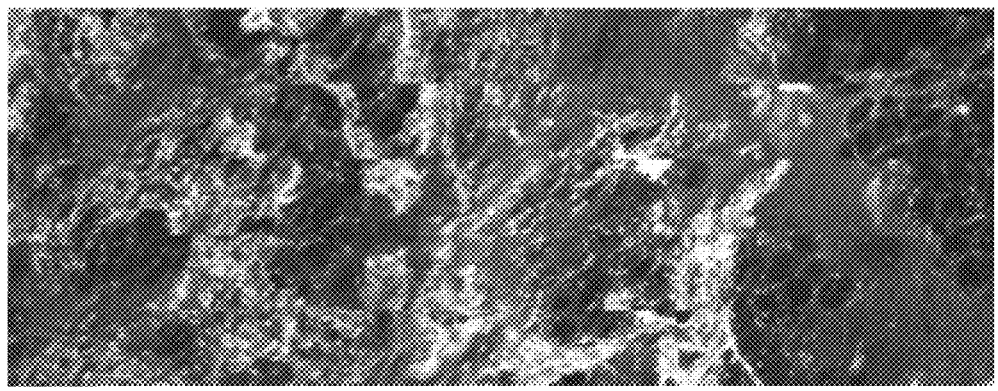

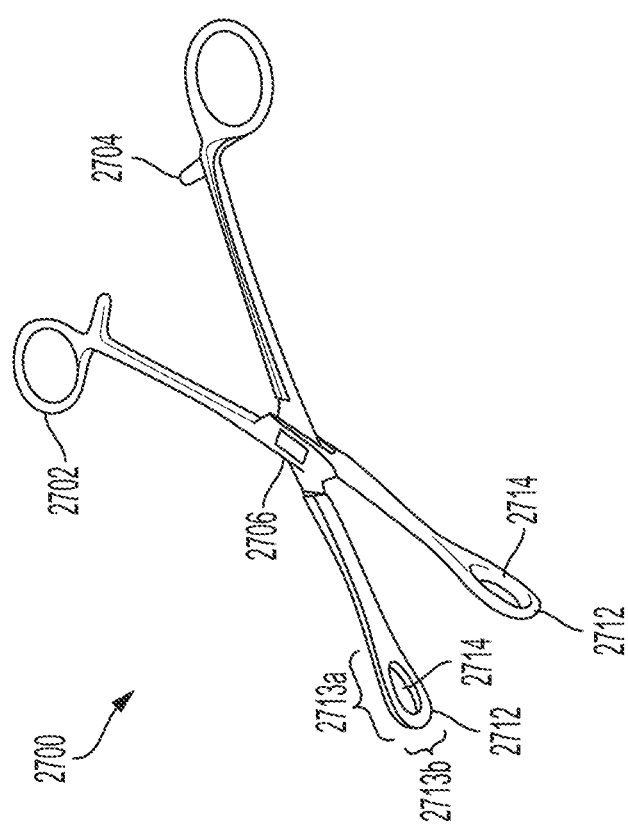
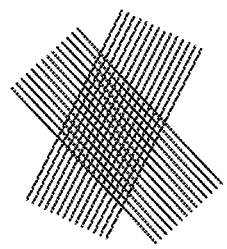
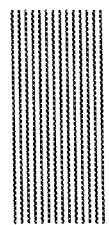
FIG. 27
FIG. 28A
FIG. 28B
FIG. 28C

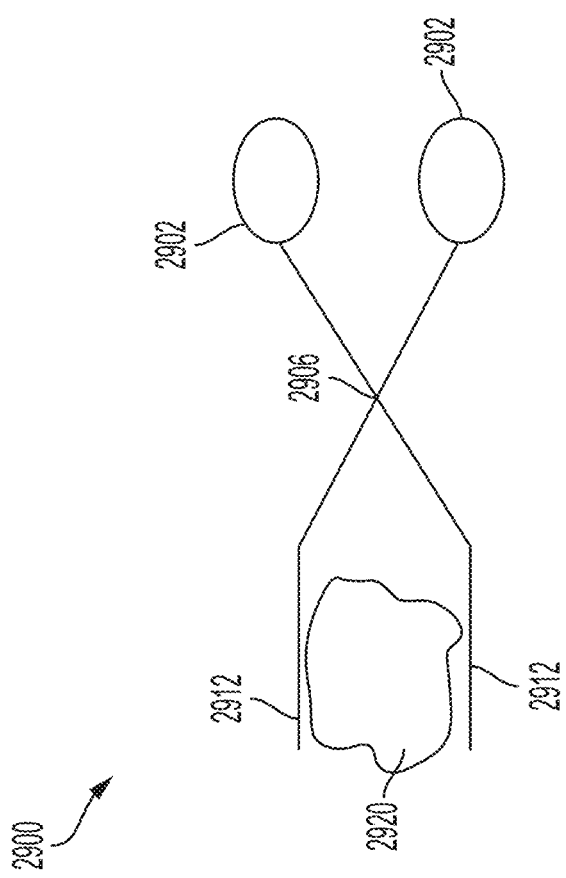

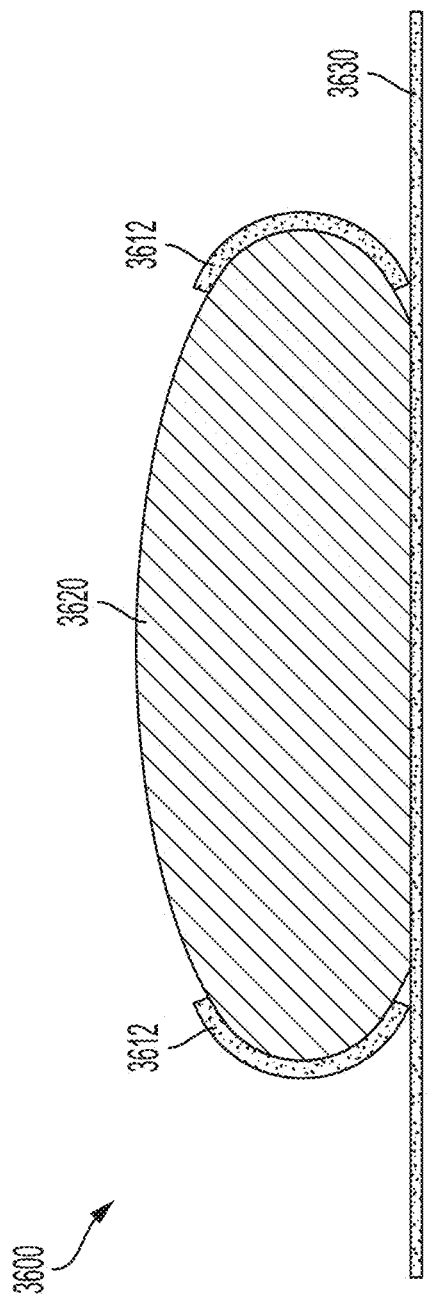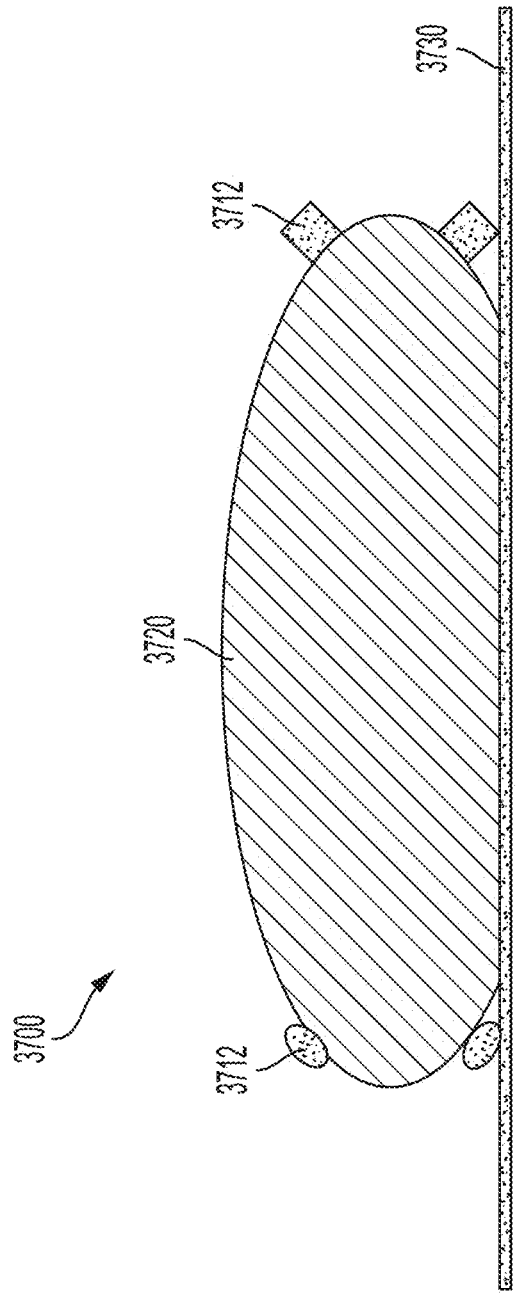

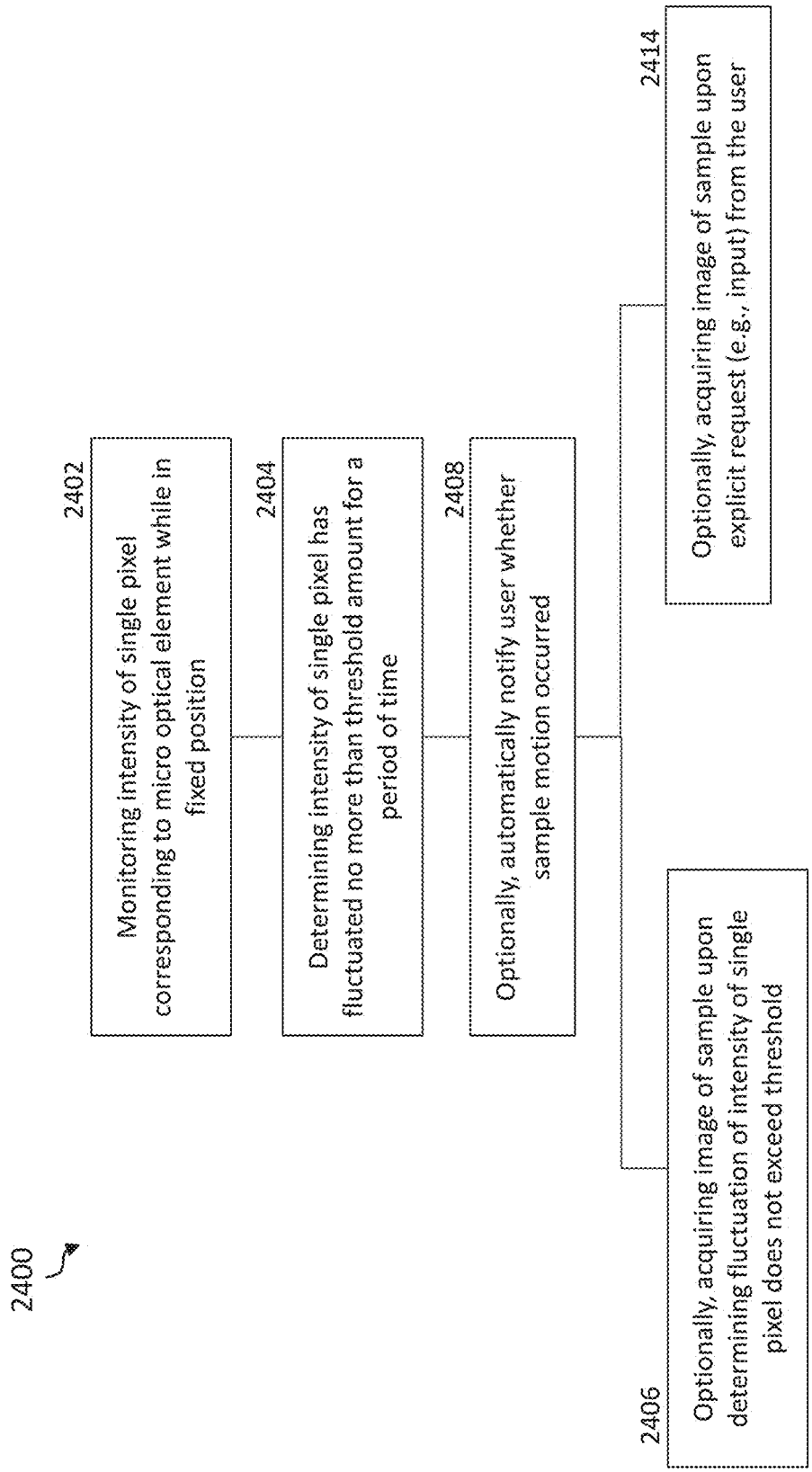

SYSTEMS AND METHODS FOR IMAGING SAMPLES WITH REDUCED SAMPLE MOTION ARTIFACTS

PRIORITY APPLICATION

This application claims the benefit of U.S. Provisional Patent Application No. 62/975,742, filed on Feb. 12, 2020, the disclosure of which is hereby incorporated by reference herein in its entirety.

TECHNICAL FIELD

This disclosure relates generally to systems, methods, and tools for imaging samples (e.g., biological tissue). In certain embodiments, systems, methods, and/or tools are used to reduce or eliminate artifacts from sample motion.

BACKGROUND

Microscopy of biological tissue samples often involves extensive tissue processing steps, including tissue fixing, embedding in paraffin, slicing to a section of a few microns thick and mounting on glass slide. The thin tissue section in the resulting "slide" is therefore completely inert and further maintained by the rigidity of the glass slide. Therefore, even if the slide imaging takes time and involves moving the glass slide around to take images at various locations to reconstruct a larger mosaic, with or without stitching, there are never problems related to undesired motion of the tissue sample during the imaging. Some systems allow a sample to perform "slide-free" tissue microscopy. These tissue samples can even be unfixed and unfrozen (e.g., can be fresh tissue samples excised during surgery). In some techniques that do not use such a fixation procedure, a sample may move (e.g., relax) during imaging, for example due to its size and/or weight. Sample motion may be appreciable over an image acquisition time. Therefore, sample motion during imaging may result in undesirable imaging artifacts.

An imaging system used to acquire an image may be a sequential imaging system. For example, an imaging system may acquire the image of one tile before acquiring the image of another tile. Imaging a moving sample with such an imaging system can produce images containing sample motion artifacts that will manifest as discontinuities between the tiles.

SUMMARY

While small sample motion artifacts in an image can be annoying for the image observer, larger magnitude sample motion artifacts may disturb interpretation of an image (e.g., by a physician or a computer algorithm). For example, a fresh breast lump put on a flat imaging window of an imaging system can take several minutes to fully relax and stop moving—at the microscopic scale. Over this time frame, sample motion may be large initially (thus producing larger magnitude sample motion artifacts) and eventually smaller (thus producing small sample motion artifacts) and eventually become imperceptible relative to a resolution of the image being acquired.

The present disclosure provides, inter alia, systems and methods that can reduce or eliminate image artifacts that may otherwise be present in an image due to sample motion that occurs during imaging. Systems may include, and/or methods may use, an array of micro optical elements (e.g., including one or more of refractive lenses, Fresnel zone plates, reflective objectives, and gradient-index (GRIN) lenses). Images acquired by such systems may include tiles of pixels, each of the tiles corresponding to a micro optical element in an array of micro optical elements and each of the pixels corresponding to a position of a micro optical element in a scan pattern during image acquisition. An imaging system used to acquire an image may be a parallel imaging system. For example, an imaging system may acquire pixels from all tiles simultaneously while imaging. For example objectives may be micro optical elements in an array of micro optical elements. Imaging a moving sample with such an imaging system may also produce images containing sample motion artifacts that will manifest as discontinuities between the tiles, for example if a conventional raster scan is used.

Sample motion artifacts may be mitigated by balance image acquisition time and scan resolution (e.g., where a minimum acceptable resolution is determined by sample features to imaged). Sample motion artifacts may also be reduced or eliminated using scan patterns where an acquisition time difference between when perimeter pixels in adjacent tiles are acquired is reduced, as compared to a conventional raster scan. For example, spiral scan patterns (either inward or outward spirals) may be used to achieve a smaller time difference across adjacent pixels in adjacent tiles of an image. A reduced time difference may reduce or eliminate discontinuities that would otherwise appear at tile boundaries in an image (e.g., along one or two dimensions). In some embodiments, test images acquired using relatively small test scan patterns or intensities of test points acquired at different times (e.g., periodically) may be compared to determine whether sample motion has occurred. In some embodiments, acquired images are analyzed to determine whether sample motion has occurred during imaging by comparing adjacent pixels at a tile boundary. For example, sample motion may be determined to occur when pixel intensity differences across tile boundaries exceeds a threshold (e.g., determined by interior pixels in one or more tiles). In some embodiments, intensity of one or more single pixels (e.g., one in each of one or more tiles) is monitored over time to determine whether sample motion has occurred over a period of time. In some embodiments, a flattening or reshaping tool may be used to suppress sample motion during imaging.

In some aspects, a method of imaging a sample using an array of micro optical elements (e.g., with reduced sample motion artifacts) comprises scanning the array of micro optical elements along a scan pattern defined by an array of sequential positions to generate an image of the sample. The array of sequential positions may be an M×N array where M and N are each no less than 10, and, optionally, M≥N. In some embodiments, the image comprises tiles of pixels. The tiles may each correspond to a respective micro optical element in the array and the pixels each corresponding to a position in the array of sequential positions. In some embodiments, for each pair of a first pixel in a first one of the tiles and a second pixel adjacent to the first pixel, the second pixel being in a different one of the tiles than the first one of the tiles, a time difference between acquisition of the first pixel and the second pixel is less than 30% (e.g., less than 10% or less than 5% or less than 1%) of a total time required to scan the array of micro optical elements along every position in the scan pattern.

In some embodiments, the method comprises during the scanning, (i) providing illumination light to the sample through the micro optical elements and (ii) collecting corresponding back-emitted light from the sample with the micro optical elements that is subsequently received at a detector. In some embodiments, the method comprises generating, by a processor of a computing device, the image of the sample based on the corresponding back-emitted light received at the detector.

In some embodiments, the scan pattern has a size corresponding to a size of a unit cell of a micro optical element in the array of micro optical elements.

In some embodiments, for each pair of a first pixel in a first one of the tiles and a second pixel adjacent to the first pixel, the second pixel being in a different one of the tiles than the first one of the tiles, a time difference between acquisition of the first pixel and the second pixel is less than $(MN-2M+1)dt$, wherein dt is a time step for scanning, M and N are each no less than 5, and $M \geq N$ (e.g., a position difference between the position corresponding to the first pixel and the position corresponding to the second pixel is less than $(MN-2M+1)$). In some embodiments, the time difference is no more than $(3M-3)dt$. In some embodiments, the time difference is no more than $(2M-1)dt$.

In some embodiments, the array of sequential positions comprises a starting position and a final position and wherein the final position is a distance of no more than two thirds of a length of the scan pattern from the starting position in a length dimension and no more than two thirds of a width of the scan pattern in a width dimension. In some embodiments, the final position is no more than half the length in the length dimension and no more than half the width in the width dimension, from the starting position. In some embodiments, the width dimension is perpendicular to the length dimension. In some embodiments, a set of positions in a perimeter of the scan pattern comprises at least a third (e.g., at least half or at least three quarters) of all positions in the perimeter, wherein the positions in the set are successive sequential positions in the scan pattern.

In some embodiments, the array of sequential positions forms a spiral (e.g., an inward spiral or an outward spiral). In some embodiments, after each of a plurality of direction changes in the series of sequential positions, the array of micro optical elements moves to a number of positions in the series of sequential positions before another of the plurality of direction changes occurs that is either (i) always no less than or (ii) always no more than a number of positions that were moved to since an immediately preceding one of the plurality of direction changes.

In some embodiments, the series of sequential positions comprises a series of sequential rows of positions, wherein each of the sequential rows in the series that is not first or last is spatially separated from its temporally adjacent rows in the series by at least one other row in the series. In some embodiments, the scan pattern is unidirectional (e.g., such that sequentially adjacent rows in the series of sequential rows are scanned in a same direction). In some embodiments, the scan pattern is bidirectional (e.g., such that sequentially adjacent rows in the series of sequential rows are scanned in different directions). In some embodiments, a starting position of the scan pattern is in an interior one of the sequential rows of positions and a final position of the scan pattern is in an exterior one of the sequential rows of positions. In some embodiments, each row in the series of sequential rows of positions is no closer to the interior one of the sequential rows of positions than an immediately preceding row in the series of sequential rows of positions.

In some embodiments, a starting position of the scan pattern is in an exterior one of the sequential rows of positions and a final position of the scan pattern is in an interior one of the sequential rows of positions. In some embodiments, each row in the series of sequential rows of positions is no further from the interior one of the sequential rows of positions than an immediately preceding row in the series of sequential rows of positions. In some embodiments, each of the sequential rows in the series that is not first or last is spatially separated from its temporally adjacent rows in the series by at least one other row in the series In some embodiments, the array of sequential positions is a regular array (e.g., a square array).

In some aspects, a method of imaging a sample [e.g., a biological sample (e.g., a resected tissue sample) (e.g., a stained biological sample)] using an array of micro optical elements (e.g., with reduced sample motion artifacts) comprises scanning the array of micro optical elements along a scan pattern defined by an array of sequential positions to generate an image of the sample. A set of perimeter positions in a perimeter of the scan pattern may comprise at least a third (e.g., at least half or at least three quarters) of all positions in the perimeter. The perimeter positions in the set may be successive sequential positions in the scan pattern.

In some aspects, a method of imaging a sample [e.g., a biological sample (e.g., a resected tissue sample) (e.g., a stained biological sample)] using an array of micro optical elements (e.g., with reduced sample motion artifacts) comprises scanning the array of micro optical elements along a scan pattern defined by an array of sequential positions to generate an image. The series of sequential positions may comprise a starting position and a final position. The final position may be a distance of no more than two thirds of a length of the scan pattern from the starting position in a length dimension. The final position may be a distance of no more than two thirds of a width of the scan pattern in a width dimension (e.g., and no more than two thirds of a length of the scan pattern in a length dimension).

In some aspects, a method of imaging a sample [e.g., a biological sample (e.g., a resected tissue sample) (e.g., a stained biological sample)] using an array of micro optical elements (e.g., with reduced sample motion artifacts) comprises scanning the array of micro optical elements along a series of sequential positions defining a scan pattern to generate an image of the sample (e.g., based on back-emitted light collected from the sample during the scanning). In some embodiments, after each of a plurality of direction changes in the series of sequential positions, the array of micro optical elements moves to a number of positions in the series of sequential positions before another of the plurality of direction changes occurs that is either (i) always no less or (ii) always no more than a number of positions that were moved to since an immediately preceding one of the plurality of direction changes.

In some aspects, a method of imaging a sample [e.g., a biological sample (e.g., a resected tissue sample) (e.g., a stained biological sample)] using an array of micro optical elements (e.g., with reduced sample motion artifacts) comprises scanning the array of micro optical elements along a scan pattern defined by an array of sequential positions to generate an image of the sample, wherein the array of sequential positions is an M×N array. The image may comprise tiles of pixels. The tiles may each correspond to a unit cell of a respective micro optical element in the array. The pixels may each correspond to a position in the array of sequential positions. In some embodiments, for each pair of a first pixel in a first one of the tiles and a second pixel adjacent to the first pixel, the second pixel being in a different one of the tiles than the first one of the tiles, a position difference between the position corresponding to the first pixel and the position corresponding to the second pixel is less than (MN−2M+1), wherein M and N are each no less than 5 and M≥N. In some embodiments, M=N and the position difference is no more than (3M−3). In some embodiments, M=N and the position difference is no more than (2M−1).

In some aspects, a method of imaging a sample [e.g., a biological sample (e.g., a resected tissue sample) (e.g., a stained biological sample)] using an array of micro optical elements (e.g., with reduced sample motion artifacts) comprises scanning the array of micro optical elements along a scan pattern defined by an array of sequential positions to generate an image of the sample. The array of sequential positions may be an M×N array of the sequential positions consisting of perimeter positions and interior positions that are interior to the perimeter positions. In some embodiments, an average sequence location of the perimeter positions in the array of sequential positions is less than MN/2 (e.g., wherein an average time during the scanning at which pixels corresponding to the perimeter positions were acquired is less than (MN/2)dt and dt is a time step for each respective position in the array of sequential positions during the scanning). In some embodiments, the average sequence location is less than 0.6*(MN/2). In some embodiments, the average sequence location is less than 0.1*(MN/2).

In some aspects, a method of detecting whether sample motion has occurred during acquisition of an image comprises receiving, by a processor of a computing device, an image comprising tiles of pixels, each of the tiles corresponding to an area scanned by a micro optical element in an array of micro optical elements when acquiring the image. In some embodiments, the method comprises determining, by the processor, whether sample motion has occurred during imaging (e.g., and an amount of sample motion) based, at least in part, on at least one pair of adjacent perimeter pixels in the image. In some embodiments, each of the at least one pair comprises a first perimeter pixel of the pixels in a first tile of the tiles and a second perimeter pixel of the pixels in a second tile adjacent to the first tile, the second perimeter pixel being adjacent to the first perimeter pixel in the image.

In some embodiments, the method comprises determining, by the processor, whether the sample motion has occurred during imaging based, at least in part, on an intensities of the pixels in the at least one pair of adjacent perimeter pixels. In some embodiments, the at least one pair of adjacent perimeter pixels comprises a plurality of first pixels (e.g., every pixel) in a first tile edge and a plurality of second pixels in a second tile edge, the first tile edge being adjacent to the second tile edge in the image. In some embodiments, the method comprises determining, by the processor, whether the sample motion has occurred during imaging based, at least in part, on an average of intensities of the plurality of first pixels and an average of intensities of the plurality of second pixels. In some embodiments, the method comprises determining, by the processor, whether the sample motion has occurred during imaging based, at least in part, on a sum of intensities of the plurality of first pixels and a sum of intensities of the plurality of second pixels. In some embodiments, the at least one pair of adjacent perimeter pixels comprises pixels from more than two pairs of neighboring tiles [e.g., is at least half of the tiles (e.g., is every one of the tiles)].

In some embodiments, the method comprises determining, by the processor, an intensity statistic (e.g., mean, median, mode, variance, standard deviation) based on intensities of interior ones of the pixels of one or more of the tiles. The method may comprise determining, by the processor, an intensity difference threshold based at least in part on the intensity statistic. The method may comprises determining, by the processor, whether the sample motion has occurred during imaging based at least on a comparison between (i) the at least one pair of adjacent perimeter pixels and (ii) the intensity difference threshold.

In some embodiments, each of the interior ones of the pixels is adjacent to at least one other pixel of the interior ones of the pixels in the image. In some embodiments, the method comprises determining, by the processor, that whether the sample motion has occurred during imaging (e.g., that the sample motion has occurred) (e.g., and an amount of sample motion) based on determining that a difference in intensity between the pixels in each of the at least one pair of adjacent perimeter pixels exceeds the intensity difference threshold.

In some embodiments, the at least one pair of adjacent perimeter pixels comprises a plurality of first pixels (e.g., every pixel) in a first tile edge and a plurality of second pixels in a second tile edge, the first tile edge being adjacent to the second tile edge in the image and determining, by the processor, whether the sample motion has occurred during imaging comprises comparing an intensity difference based on intensities of the plurality of first pixels and intensities of the plurality of second pixels to the intensity difference threshold. In some embodiments, the intensity difference is based on an average of intensities of the plurality of first pixels and an average of intensities of the plurality of second pixels. In some embodiments, the intensity difference is based on a sum of intensities of the plurality of first pixels and a sum of intensities of the plurality of second pixels.

In some embodiments, the method comprises applying, by the processor, the intensity difference threshold to the image, thereby generating a thresholded image and displaying, via one or more graphical user interfaces (e.g., by the processor), the thresholded image.

In some embodiments, the method comprises determining, by the processor, that the sample motion has occurred during imaging based, at least in part, the at least one pair of adjacent perimeter pixels (e.g., an intensity of the pixels in the at least one pair of adjacent perimeter pixels). In some embodiments, the method comprises automatically notifying (e.g., in one or more graphical user interfaces) a user that the sample motion has occurred during imaging (e.g., and the amount of sample motion) upon determining that the sample motion has occurred. In some embodiments, the method comprises automatically acquiring, by the processor, a second image of the sample upon determining that the sample motion has occurred during imaging. In some embodiments, acquiring the second image comprises scanning the array of micro optical elements along a scan pattern (e.g., wherein a size of the scan pattern corresponds to a size of a unit cell of a micro optical element in the array).

In some embodiments, the method comprises normalizing, by the processor, the image based on characteristic (e.g., average) intensities of tiles in the image prior to determining whether the sample motion has occurred during imaging (e.g., thereby reducing effect(s) resulting from a Gaussian distribution of intensity in light provided through the array of micro optical elements when acquiring the image). In some embodiments, the method comprises applying, by the processor, one or more morphological operators to the image prior to determining whether the sample motion has occurred during imaging (e.g., and after determining the intensity difference threshold). In some embodiments, the one or more morphological operators comprises an erode followed by a dilate. In some embodiments, the erode is a one dimensional erode and the dilate is a one dimensional dilate (e.g., applied perpendicularly to a slow scan direction).

In some embodiments, the method comprises displaying, by the processor, to a user the amount of sample movement in a graphical user interface.

In some embodiments, the pixels correspond to positions in a scan pattern along which the array of micro optical elements is scanned in order to acquire the image. In some embodiments, the tiles each comprise data corresponding to back-emitted light received from the sample through a respective micro optical element in the array of micro optical elements during acquisition of the image.

In some aspects, a method of detecting whether sample motion has occurred during acquisition of an image comprises receiving, by a processor of a computing device, an image comprising tiles of pixels. Each of the tiles may correspond to an area scanned by a micro optical element in an array of micro optical elements when acquiring the image. The method may include generating, by the processor, a difference image from the image based on a single pixel shift (e.g., in a horizontal or vertical direction). The method may include determining, by the processor, whether sample motion has occurred during imaging (e.g., and an amount of sample motion) based, at least in part, on the difference image.

In some embodiments, the method comprises determining whether the sample motion has occurred during imaging based, at least in part, on whether intensities of pixels in the difference image exceed an intensity threshold. In some embodiments, the intensity threshold is based on an average intensity of pixels (e.g., all pixels) (e.g., interior pixels) in the difference image. In some embodiments, the method comprises normalizing the difference image prior to determining whether the sample motion has occurred. In some embodiments, the method comprises applying, by the processor, one or more morphological operators to the image prior to determining whether the sample motion has occurred during imaging (e.g., and after normalization).

In some aspects, a system for detecting whether sample motion has occurred during acquisition of an image may include a processor and a non-transitory computer readable medium having instructions stored thereon, wherein the instructions, when executed by the processor, cause the processor to: receive an image comprising tiles of pixels, each of the tiles corresponding to an area scanned by a micro optical element in an array of micro optical elements when acquiring the image. The instructions, when executed, may cause the processor to determine whether sample motion has occurred during imaging (e.g., and an amount of sample motion) based, at least in part, on at least one pair of adjacent perimeter pixels in the image. In some embodiments, each of the at least one pair comprises a first perimeter pixel of the pixels in a first tile of the tiles and a second perimeter pixel of the pixels in a second tile adjacent to the first tile, the second perimeter pixel being adjacent to the first perimeter pixel in the image. In some embodiments, the system comprises the micro optical element array.

In some aspects, an imaging system for detecting whether sample motion has occurred during acquisition of an image comprises a processor and a non-transitory computer readable medium having instructions stored thereon, wherein the instructions, when executed by the processor, cause the processor to: receive an image comprising tiles of pixels, each of the tiles corresponding to an area scanned by a micro optical element in an array of micro optical elements when acquiring the image. The instructions, when executed, may cause the processor to generate a difference image from the image based on a single pixel shift (e.g., in a horizontal or vertical direction). The instructions, when executed, may cause the processor to determine whether sample motion has occurred during imaging (e.g., and an amount of sample motion) based, at least in part, on the difference image. In some embodiments, the system comprises the micro optical element array.

In some aspects, a method of determining whether a sample [e.g., a biological sample (e.g., a resected tissue sample) (e.g., a stained biological sample)] has moved (e.g., has self-stabilized prior to imaging) comprises acquiring (e.g., automatically) a first test image of the sample in part by scanning an array of micro optical elements over a first test scan pattern. The first test scan pattern may have an area that is smaller than an area of a unit cell of a micro optical element in the array of micro optical elements; In some embodiments, the method comprises acquiring (e.g., automatically), after a period of delay (e.g., and without manipulating the sample), a second test image of the sample in part by scanning the array over a second test scan pattern. The second test scan pattern may correspond in size to the first test scan pattern. In some embodiments, the method comprises determining, by a processor of a computing device, whether sample motion has occurred between acquiring the first test image and acquiring the second test image at least in part by comparing the second test image to the first test image.

In some embodiments, comparing the second test image to the first test image comprises determining a stabilization index $S(t_2-t_1)$. In some embodiments, comparing the second test image to the first test image comprises comparing one or more corresponding pairs of pixels from the first test image and the second test image.

In some embodiments, whether sample motion has occurred is determined based, at least in part, on whether a rate of sample motion is no more than a predetermined sample-motion-rate threshold. In some embodiments, whether sample motion has occurred is determined based, at least in part, on whether an amount of sample motion is no more than a predetermined sample motion threshold.

In some embodiments, the method comprises determining that the rate of sample motion is no more than the predetermined sample-motion-rate threshold. In some embodiments, the method comprises subsequently acquiring (e.g., automatically, e.g., without user input) a full image in part by scanning the array of micro optical elements over a scan pattern. The scan pattern may have an area corresponding to the area of the unit cell. In some embodiments, positions in the first test scan pattern and positions in the second scan pattern are each respectively spatially denser than positions in the scan pattern used to acquire the full image. In some embodiments, a resolution of the first test image and a resolution of the second test image are each higher than a resolution of the full image. In some embodiments, the method comprises acquiring a full test image of the sample between acquiring the first test image and acquiring the second test image. The full test image may be acquired in part by scanning the array of micro optical elements over a scan pattern having an area corresponding to the area of the unit cell of the micro optical element in the array. In some embodiments, the full test image is acquired (i) relatively quickly, (ii) at a relatively low resolution, or (iii) both relatively quickly and at a relatively low resolution and the full image is acquired (i) relatively slowly, (ii) at a relatively high resolution, or (iii) both relatively slowly and at a relatively high resolution, respectively.

In some embodiments, whether sample motion has occurred is determined based at least in part on whether a rate of sample motion is no more than a predetermined sample-motion-rate threshold and the predetermined sample-motion-rate threshold is no more than 1.5× a pixel size (e.g., an image resolution) of the full image divided by an acquisition time of the full image. In some embodiments, the predetermined sample-motion-rate threshold is a pixel size (e.g., an image resolution) of the full image divided by an acquisition time of the full image. In some embodiments, the period of delay corresponds to an acquisition time of the full image. In some embodiments, the period of delay corresponds to no more than 50% (e.g., no more than 25% or no more than 10%) of an acquisition time of the full image.

In some embodiments, the area of the first test scan pattern and the area of the second test scan pattern are each no less than one thousandth (e.g., no less than one hundredth) and no more than one quarter (e.g., no more than one hundredth) of the area of the unit cell. In some embodiments, the area of the first test scan pattern and the area of the second test scan pattern are each no less than one hundredth and no more than one tenth of the area of the unit cell. In some embodiments, the area of the first test scan pattern and the area of the second test scan pattern are each no less than one thousandth and no more than one hundredth of the area of the unit cell.

In some embodiments, each position in the first test scan pattern corresponds to a respective position in the second test scan pattern (e.g., the second test scan pattern is the first test scan pattern). In some embodiments, comparing the second test image to the first test image comprises determining an intensity difference (e.g., of normalized intensity) (e.g., an average intensity difference) between a portion of the first test image and a spatially corresponding portion of the second test image. In some embodiments, determining the intensity difference comprises directly comparing a pixel of the first test image to a pixel of the second test image (e.g., comprises directly comparing a subset of pixels of the first test image to a subset of pixels of the second test image). In some embodiments, comparing the second test image to the first test image comprises: applying an image correlation technique thereby determining a displacement from the first test image to the second test image.

In some embodiments, the period of delay is at least 2 seconds and no more than 60 seconds. In some embodiments, the period of delay is at least 2 seconds (e.g., at least 5 seconds) and no more than 30 seconds.

In some embodiments, the method comprises acquiring (e.g., automatically), after a second period of delay, a third test image of the sample in part by scanning the array over a third test scan pattern, wherein the third test scan pattern corresponds in size to the first test scan pattern. The method may comprise determining whether sample motion has occurred at least in part by comparing the third test image to the second test image. In some embodiments, the second period of delay is equal to the period of delay. In some embodiments, the method comprises determining that the sample motion has occurred, wherein acquiring, after the second period of delay, the third test image occurs subsequent to determining that the sample motion has occurred.

A period of delay may be the time it takes to reset to a starting point of a scan pattern and begin scanning again or the time it takes to make another scan (e.g., where every other scan is compared or otherwise analyzed).

In some embodiments, the method comprises determining that a rate of sample motion is no more than a predetermined sample-motion-rate threshold and, optionally, subsequently notifying a user (e.g., via a graphical user interface, e.g., a pop-up notification) that the sample has self-stabilized (e.g., automatically).

In some embodiments, the first test scan pattern and the second test scan pattern are each a one-dimensional scan pattern. In some embodiments, a size of the first test scan pattern and/or a size of the second test scan pattern is less than a size of the unit cell (e.g., optionally and/or a resolution of the first test image and/or the second test image is less than a resolution of a subsequently acquired full image). In some embodiments, the first test scan pattern and/or the second test scan pattern corresponds to a fast scan axis (e.g., for a subsequently acquired full image). In some embodiments, the first test scan pattern and the second test scan pattern are each a two-dimensional scan pattern.

In some aspects, an imaging system for determining whether a sample [e.g., a biological sample (e.g., a resected tissue sample) (e.g., a stained biological sample)] has moved (e.g., has self-stabilized prior to imaging) comprises a processor and a non-transitory computer readable medium having instructions stored thereon, wherein the instructions, when executed by the processor, cause the processor to: acquire (e.g., automatically) a first test image of the sample in part by scanning an array of micro optical elements over a first test scan pattern. The first test scan pattern may have an area that is smaller than an area of a unit cell of a micro optical element in the array of micro optical elements. The instructions, when executed, may cause the processor to acquire (e.g., automatically), after a period of delay (e.g., and without manipulating the sample), a second test image of the sample in part by scanning the array over a second test scan pattern. The second test scan pattern may correspond in size to the first test scan pattern. The instructions, when executed, may cause the processor to determine whether sample motion has occurred between acquiring the first test image and acquiring the second test image at least in part by comparing the second test image to the first test image. In some embodiments, the system comprises the micro optical element array.

In some aspects, a method for determining whether a sample [e.g., a biological sample (e.g., a resected tissue sample) (e.g., a stained biological sample)] has moved (e.g., self-stabilized) prior to imaging comprises monitoring, by a processor of a computing device, intensity of a single pixel corresponding to a micro optical element in an array of micro optical elements while the array remains in a fixed position. The intensity may be based on an amount of light back-emitted from the sample and received by a detector through the micro optical element. The method may include determining, by the processor, whether sample motion has occurred based on fluctuation in the intensity of the single pixel.

In some embodiments, determining whether the sample motion has occurred is based on an intensity difference between a minimum intensity and a maximum intensity of the single pixel (e.g., per tile) over a period of time. In some embodiments, determining whether the sample motion has occurred is based on a cumulative absolute difference in intensity of the single pixel (e.g., between all successive values recorded) over a period of time (e.g., wherein the cumulative absolute difference in intensity has been averaged, e.g., with a moving average filter).

In some embodiments, determining whether the sample motion has occurred is based, at least in part, on determining whether the intensity of the single pixel has fluctuated no more than a threshold amount (e.g., a predetermined threshold amount) for a period of time. In some embodiments, the threshold amount is no more than 20%. In some embodiments, the threshold amount is no more than 10%.

In some embodiments, the method comprises acquiring an image of the sample (e.g., automatically, e.g., without user input) upon determining that the intensity of the single pixel has fluctuated no more than the threshold amount for the period of time. In some embodiments, the threshold amount is a predetermined threshold amount and the method comprises predetermining the threshold amount based on one or more of (i) a resolution (e.g., a selected resolution) of the image to be acquired before beginning the monitoring and (ii) one or more characteristics of the sample. In some embodiments, acquiring the image of the sample comprises scanning the array of micro optical elements over a scan pattern, wherein the scan pattern has an area corresponding to an area of a unit cell of the micro optical element.

In some embodiments, the method comprises acquiring a test image of the sample concurrently with the monitoring of the intensity of the single pixel by acquiring the test image between discrete measurements of the intensity of the single pixel. In some embodiments, the method comprises acquiring a test image of the sample during the monitoring of the intensity of the single pixel, wherein at least one discrete measurement of the intensity of the single pixel is cancelled or delayed in order to complete acquisition of the test image. In some embodiments, acquiring the test image comprises scanning the array of micro optical elements over a scan pattern. The scan pattern may have an area corresponding to an area of a unit cell of the micro optical element. In some embodiments, the method comprises acquiring an image of the sample (e.g., automatically, e.g., without user input) upon determining that the intensity of the single pixel has fluctuated no more than a threshold amount for a period of time. The test image may be acquired (i) relatively quickly, (ii) at a relatively low resolution, or (iii) both relatively quickly and at a relatively low resolution and the image of the sample is acquired (i) relatively slowly, (ii) at a relatively high resolution, or (iii) both relatively slowly and at a relatively high resolution, respectively.

In some embodiments, the method comprises notifying a user (e.g., via a graphical user interface, e.g., a pop-up notification) that the sample has self-stabilized (e.g., automatically) upon determining that the intensity of the single pixel has fluctuated no more than a threshold amount for a period of time.

In some embodiments, the method comprises monitoring intensity of a respective single pixel corresponding to one of a plurality of the micro optical elements in the array, for each of the plurality of the micro optical elements, while the array remains in the fixed position. The intensity of the respective single pixel may be based on an amount of light back-emitted from the sample and received by a detector through the one of the plurality of the micro optical elements. The method may comprise determining whether the sample motion has occurred based, at least in part, on the respective single pixel for each of the plurality of the micro optical elements.

In some embodiments, the method comprises acquiring an image of the sample (e.g., automatically) upon determining that a maximum fluctuation in the intensity of the respective single pixel for each of the plurality of micro optical elements is no more than a threshold amount for a period of time. In some embodiments, the method comprises acquiring an image of the sample (e.g., automatically) upon determining that a difference between maximum and a minimum fluctuation in the intensity of the respective single pixel for each of the plurality of micro optical elements is no more than a threshold amount for a period of time. In some embodiments, the method comprises acquiring an image of the sample (e.g., automatically) upon determining that cumulative absolute difference in the intensity of the respective single pixel for each of the plurality of micro optical elements is no more than a threshold amount for a period of time (e.g., after normalization, e.g., with a moving average filter).

In some embodiments, the method comprises acquiring an image of the sample (e.g., automatically) upon determining that the intensity of the respective single pixel for each of the plurality of micro optical elements has fluctuated no more than a threshold amount for a period of time. In some embodiments, the method comprises acquiring an image of the sample (e.g., automatically) upon determining that an average of the intensity of the respective single pixel for each of the plurality of micro optical elements has fluctuated no more than a threshold amount for a period of time. In some embodiments, the method comprises acquiring an image of the sample (e.g., automatically) upon determining that an average fluctuation of the intensity of the respective single pixel for each of the plurality of micro optical elements does not exceed a threshold amount for a period of time. In some embodiments, the plurality of micro optical elements comprises at least a quarter (e.g., at least half) of the micro optical elements in the array. In some embodiments, the plurality of micro optical elements comprises every micro optical element in the array.

In some embodiments, the period of time is at least 2 seconds and no more than 90 seconds. In some embodiments, the period of time is at least 5 seconds and no more than 30 seconds.

In some embodiments, monitoring the intensity of the single pixel comprises: receiving on the detector first back-emitted light from the sample through the micro optical element over a first period. the intensity of the single pixel at a first time may be automatically determined based on the first back-emitted light received. Monitoring the intensity of the single pixel may further comprise receiving on the detector (e.g., after a period of delay from receiving the first back-emitted light) second back-emitted light from the sample through the micro optical element over a second period equal in length to the first period. The intensity of the single pixel at a second time may be automatically determined based on the second back-emitted light received.

In some embodiments, determining whether the sample motion has occurred comprises comparing at least the intensity of the single pixel at the first time and the intensity of the single pixel at the second time.

In some embodiments, the detector is a CCD or CMOS camera.

In some aspects, an imaging system for determining whether a sample [e.g., a biological sample (e.g., a resected tissue sample) (e.g., a stained biological sample)] has moved (e.g., self-stabilized) prior to imaging comprises a processor and a non-transitory computer readable medium having instructions stored thereon, wherein the instructions, when executed by the processor, cause the processor to: monitor intensity of a single pixel corresponding to a micro optical element in an array of micro optical elements while the array remains in a fixed position. The intensity may be based on an amount of light back-emitted from the sample and received by a detector through the micro optical element. The instructions, when executed, may cause the processor to determine whether sample motion has occurred based on fluctuation in the intensity of the single pixel. In some embodiments, the system comprises the micro optical element array.

In some aspects, a sample [e.g., a biological sample (e.g., a resected tissue sample) (e.g., a stained biological sample)] flattening tool for flattening a biological sample comprises a support member having a shape that defines a channel and, optionally, a removable flattening member comprising a retention lip sized and shaped to rest on the support member. The removable flattening member may comprise an insertable portion sized and shaped to be inserted in the channel.

In some embodiments, the insertable portion has a shape defining one or more holes (e.g., square or circular holes) each sized to accommodate a harpoon protruding from the sample (e.g., each hole having a dimension of no more than 1 cm, e.g., no more than 5 mm). In some embodiments, the support member has a shape defining one or more holes each sized to accommodate a harpoon protruding from the sample (e.g., each hole having a dimension of no more than 1 cm, e.g., no more than 5 mm).

In some embodiments, the tool comprises one or more removable weights sized and shaped to be disposed on a top surface of the insertable portion (e.g., wherein the one or more removable weights are sized and shaped such that when disposed on the top surface of the insertable portion, at least one of the one or more holes remains uncovered).

In some embodiments, when the retention lip rests on the support member, a bottom surface of the flattening member is disposed no more than 1 mm (e.g., no more than 500 µm) above a bottom of the support member.

In some embodiments, the support member has an annular cross section. In some embodiments, the support member has a rectangular cross section.

In some aspects, a sample [e.g., a biological sample (e.g., a resected tissue sample) (e.g., a stained biological sample)] flattening tool for flattening a biological sample comprising: a planar top portion and, optionally, one or more wings extending downward from the top portion (e.g., such that the one or more wings partially cover the sample when the tool is flattening the sample).

In some embodiments, the one or more wings is one wing. In some embodiments, the tool has a rotational symmetry. In some embodiments, the one or more wings comprises one or more weight supports. In some embodiments, the one or more weight supports is a plurality of weight supports evenly spaced around a perimeter of the tool. In some embodiments, the one or more weight supports extend horizontally and parallel to the planar top portion.

In some embodiments, the tool comprises one or more removable weights each sized and shaped to be disposed on at least one of the one or more weight supports. In some embodiments, the one or more wings each have a shape defining one or more holes (e.g., square or circular holes) each sized to accommodate a harpoon protruding from the sample (e.g., each hole having a dimension of no more than 1 cm, e.g., no more than 5 mm).

In some embodiments, the top portion has a shape defining one or more holes (e.g., square or circular holes) each sized to accommodate a harpoon protruding from the sample (e.g., each hole having a dimension of no more than 1 cm, e.g., no more than 5 mm). In some embodiments, the one or more wings are connected to a top surface of the top portion such that the top portion and the one or more wings define a recess. In some embodiments, the tool comprises one or more removable weights sized and shaped to be disposed on a top surface of top portion at least partially in the recess (e.g., wherein the one or more removable weights are sized and shaped such that when disposed on the top surface of the top portion, at least one of the one or more holes remains uncovered).

In some embodiments, the tool is made of injection molded plastic. In some embodiments, the tool comprises metal.

In some aspects, a method of stabilizing a sample [e.g., a biological sample (e.g., a resected tissue sample) (e.g., a stained biological sample)] for imaging using an imaging system comprises: disposing the sample on a transparent imaging window such that the sample is accessible to a user during imaging; reshaping the sample with a reshaping tool; resting a portion of the reshaping toolclamp on an upper working surface of the imaging system such that the sample remains reshaped during imaging; and imaging the sample while the sample remains reshaped.

In some aspects, a method of imaging a sample [e.g., a biological sample (e.g., a resected tissue sample) (e.g., a stained biological sample)] using an array of micro optical elements (e.g., with reduced sample motion artifacts) comprises selecting an imaging time and an imaging resolution based on one or more features of the sample to be resolved (e.g., cell in the sample, nuclei of the cells, or organelles of the cells). The imaging time may be from 5 s to 30 s and, optionally, the imaging resolution may be from 10 µm to 2 µm. The method may further comprise acquiring (e.g., automatically) an image of the sample in part by scanning the array of micro optical elements over a scan pattern. The scan pattern may have an area corresponding to the area of a unit cell of a micro optical element in the array. In some embodiments, the imaging time is selected based on the imaging resolution. In some embodiments, the imaging resolution is selected based on the imaging time. In some embodiments, the imaging time is no more than 10 seconds and the imaging resolution is 5 µm or better. In some embodiments, the method comprises selecting the imaging time and the imaging resolution further based, at least in part, on a material of the sample. In some embodiments, an imaging time (t) to image resolution (r) ratio, Q, is no less than 1 and no more than 5 ($1 \leq Q \leq 5$) (e.g., $2 \leq Q \leq 5$).

In some aspects, a method of imaging a sample with an imaging system comprising an array of micro optical elements comprises: acquiring (e.g., automatically) partial image data over a period of time; determining a change in the partial image data over the period of time; determining that no more than an predetermined amount of sample motion has occurred during the period of time based on the change in partial image data; and acquiring (e.g., automatically) a full image of the sample upon determining that no more than the predetermined amount of sample motion has occurred during the period of time, wherein the full image corresponds to a larger area of the sample than an area that corresponds to the partial image data.

In some embodiments, the partial image data comprises intensity data corresponding to back-emitted light collected from the sample. In some embodiments, acquiring the partial image data comprises acquiring (e.g., automatically) one or more test images of the sample in part by scanning an array of micro optical elements over a first test scan pattern, wherein the first test scan pattern has an area that is smaller than an area of a unit cell of a micro optical element in the array of micro optical elements. In some embodiments, the one or more test images comprises two or more test images acquired at different times and determining the change in the partial image data over the period of time comprises comparing the two or more test images (e.g., by comparing intensity data therein). In some embodiments, the intensity data corresponds to intensity data for one or more single pixels (e.g., only one single pixel) (e.g., a single pixel from each of a plurality of tiles) (e.g., isolated single pixels within one or more tiles). In some embodiments, determining whether sample motion has occurred during the period of time comprises determining whether a motion index or a stabilization index exceeds a predetermined threshold. In some embodiments, the imaging system automatically acquires the full image once the imaging system has determined that no more than the predetermined amount of sample motion has occurred during the period of time.

In some embodiments, the method comprises presenting to a user, via a graphical user interface provided by the imaging system, an indicator (e.g., graphic, text, and/or sound) that no more than the predetermined amount of sample motion has occurred during the period of time. In some embodiments, the indicator is a graphic (e.g., a color and/or symbol) or text (e.g., a value and/or measure). In some embodiments, the indicator is representative of all of the sample (e.g., based on a single scalar representative for all of the sample) (e.g., is derived from data for a plurality of tiles, each corresponding to a different micro optical element in the array). In some embodiments, the indicator updates in real time. In some embodiments, acquiring the full image occurs automatically upon receiving an start imaging input from a user after or while presenting the indicator in the graphical user interface. In some embodiments, determining that no more than the predetermined amount of sample motion has occurred is based on partial image data from multiple tiles each corresponding to a different micro optical element in the array. In some embodiments, determining that no more than the predetermined amount of sample motion has occurred is based on an average of the partial image data from multiple tiles each corresponding to a different micro optical element in the array. In some embodiments, the full image is acquired using an imaging time (t) to image resolution (r) ratio, Q, is no less than 1 and no more than 5 ($1 \leq Q \leq 5$) (e.g., $2 \leq Q \leq 5$).

In some aspects, a method of detecting whether sample motion has occurred during acquisition of an image comprises: receiving, by a processor of a computing device, an image comprising tiles of pixels, each of the tiles corresponding to an area scanned by a micro optical element in an array of micro optical elements when acquiring the image; and determining, by the processor, whether sample motion has occurred during imaging (e.g., and an amount of sample motion) based, at least in part, on a motion index ($M\alpha\beta$) (e.g., where sample motion is determined to have occurred if $M_{\alpha\beta} > 2.75$).

In some aspects, a method of detecting whether sample motion has occurred during acquisition of an image comprises: receiving, by a processor of a computing device, an image comprising tiles of pixels, each of the tiles corresponding to an area scanned by a micro optical element in an array of micro optical elements when acquiring the image; and determining, by the processor, whether sample motion has occurred during imaging (e.g., and an amount of sample motion) based, at least in part, on a motion index ($M_{YZ}$) (e.g., where sample motion is determined to have occurred if $M_{YZ} > 2.75$).

In some aspects, a method of detecting whether sample motion has occurred during acquisition of an image comprises: receiving, by a processor of a computing device, an image comprising tiles of pixels, each of the tiles corresponding to an area scanned by a micro optical element in an array of micro optical elements when acquiring the image; and determining, by the processor, whether sample motion has occurred during imaging (e.g., and an amount of sample motion) based, at least in part, on a comparison of an intensity difference between adjacent pixels in a first pair of adjacent pixels in adjacent rows to an intensity difference between adjacent pixels in a second pair of adjacent pixels in a same row. In some embodiments, one of the pixels in the first pair is one of the pixels in the second pair.

In some aspects, a method of determining whether a sample [e.g., a biological sample (e.g., a resected tissue sample) (e.g., a stained biological sample)] has moved (e.g., has self-stabilized prior to imaging) comprises: acquiring (e.g., automatically) a first test image of the sample (e.g., in part by scanning an array of micro optical elements over a first test scan pattern, wherein the first test scan pattern has an area that is smaller than an area of a unit cell of a micro optical element in the array of micro optical elements); acquiring (e.g., automatically), after a period of delay (e.g., and without manipulating the sample), a second test image of the sample (e.g., in part by scanning the array over a second test scan pattern, wherein the second test scan pattern corresponds in size to the first test scan pattern); and determining, by a processor of a computing device, whether sample motion has occurred at least in part by determining a stabilization index $S(t_2-t_1)$.

In some aspects, a method of determining whether a sample [e.g., a biological sample (e.g., a resected tissue sample) (e.g., a stained biological sample)] has moved (e.g., has self-stabilized prior to imaging) comprises: acquiring (e.g., automatically) a first test image of the sample (e.g., in part by scanning an array of micro optical elements over a first test scan pattern, wherein the first test scan pattern has an area that is smaller than an area of a unit cell of a micro optical element in the array of micro optical elements); acquiring (e.g., automatically), after a period of delay (e.g., and without manipulating the sample), a second test image of the sample (e.g., in part by scanning the array over a second test scan pattern, wherein the second test scan pattern corresponds in size to the first test scan pattern); and determining, by a processor of a computing device, whether sample motion has occurred at least in part by comparing one or more corresponding pairs of pixels from the first test image and the second test image.

Any two or more of the features described in this specification, including in this summary section, may be combined to form implementations not specifically (e.g., expressly) described in this specification.

Definitions

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Image: As used herein, the term "image", for example, as in a two- or three-dimensional image of resected tissue (or other sample), includes any visual representation, such as a photo, a video frame, streaming video, as well as any electronic, digital, or mathematical analogue of a photo, video frame, or streaming video. Any system or apparatus described herein, in certain embodiments, includes a display for displaying an image or any other result produced by a processor. Any method described herein, in certain embodiments, includes a step of displaying an image or any other result produced by the method. Any system or apparatus described herein, in certain embodiments, outputs an image to a remote receiving device [e.g., a cloud server, a remote monitor, or a hospital information system (e.g., a picture archiving and communication system (PACS))] or to an external storage device that can be connected to the system or to the apparatus. In some embodiments, an image is produced using a fluorescence imaging system, a luminescence imaging system, and/or a reflectance imaging system. In some embodiments, an image is a two-dimensional (2D) image. In some embodiments, an image is a three-dimensional (3D) image. In some embodiments, an image is a reconstructed image. In some embodiments, an image is a confocal image. An image (e.g., a 3D image) may be a single image or a set of images. In some embodiments, whether sample motion has occurred is reflected by the presence of one or more sample motion artifacts in an image (e.g., a full image or a test image). The one or more sample motion artifacts may be detectable by image processing performed by an imaging system. In some embodiments, determining whether one or more sample motion artifacts are present determines (e.g., is determinative of) whether sample motion has occurred.

User: As used herein, a user is any person who uses an imaging system disclosed herein. A user may be, for example, but not limited to, a surgeon, a surgical staff (e.g., a nurse or medical practitioner in an operating room), a lab technician, a scientist, or a pathologist. It is understood that when an action is described as being performed by a surgeon, in some embodiments, a user who is not a surgeon performs an equivalent function.

BRIEF DESCRIPTION OF THE DRAWINGS

Drawings are presented herein for illustration purposes, not for limitation. The foregoing and other objects, aspects, features, and advantages of the disclosure will become more apparent and may be better understood by referring to the following description taken in conjunction with the accompanying drawings, in which:

FIG. 1A and FIG. 1B are plan views representing an illustrative rectangular optical chip comprising an array of micro lenses disposed in a square lattice, according to illustrative embodiments of the present disclosure;

FIG. 2A is a schematic of an illustrative imaging system showing illumination of a tissue sample, according to illustrative embodiments of the present disclosure;

FIG. 2B is a schematic of the illustrative imaging system according to FIG. 2A showing detection of back-emitted light from a sample by a detector, according to illustrative embodiments of the present disclosure;

FIG. 3 is a schematic illustrating a conventional bidirectional scan pattern for an objective (e.g., a micro optical element in an array of micro optical elements), according to illustrative embodiments of the present disclosure.

FIGS. 21A-E illustrate methods of determining whether sample motion has occurred during imaging based on comparing perimeter pixels of tiles to interior pixels of tiles, according to illustrative embodiments of the present disclosure;

FIG. 27 is an illustration of a clamp, according to illustrative embodiments of the present disclosure;

FIGS. 28A-C are an illustration of ribbing styles that can be used on gripping member(s) of a clamp, according to illustrative embodiments of the present disclosure;

FIG. 29 is an illustration of a clamp, according to illustrative embodiments of the present disclosure;

FIG. 36 is a cross section of a reshaping tool having concave gripping members, according to illustrative embodiments of the present disclosure;

FIG. 37 is a cross section of a reshaping tool having apertures with different cross sections, according to illustrative embodiments of the present disclosure;

FIG. 49 is a process diagram of methods for determining whether a sample has moved, according to illustrative embodiments of the present disclosure.

DETAILED DESCRIPTION OF CERTAIN EMBODIMENTS

Figure 1C:
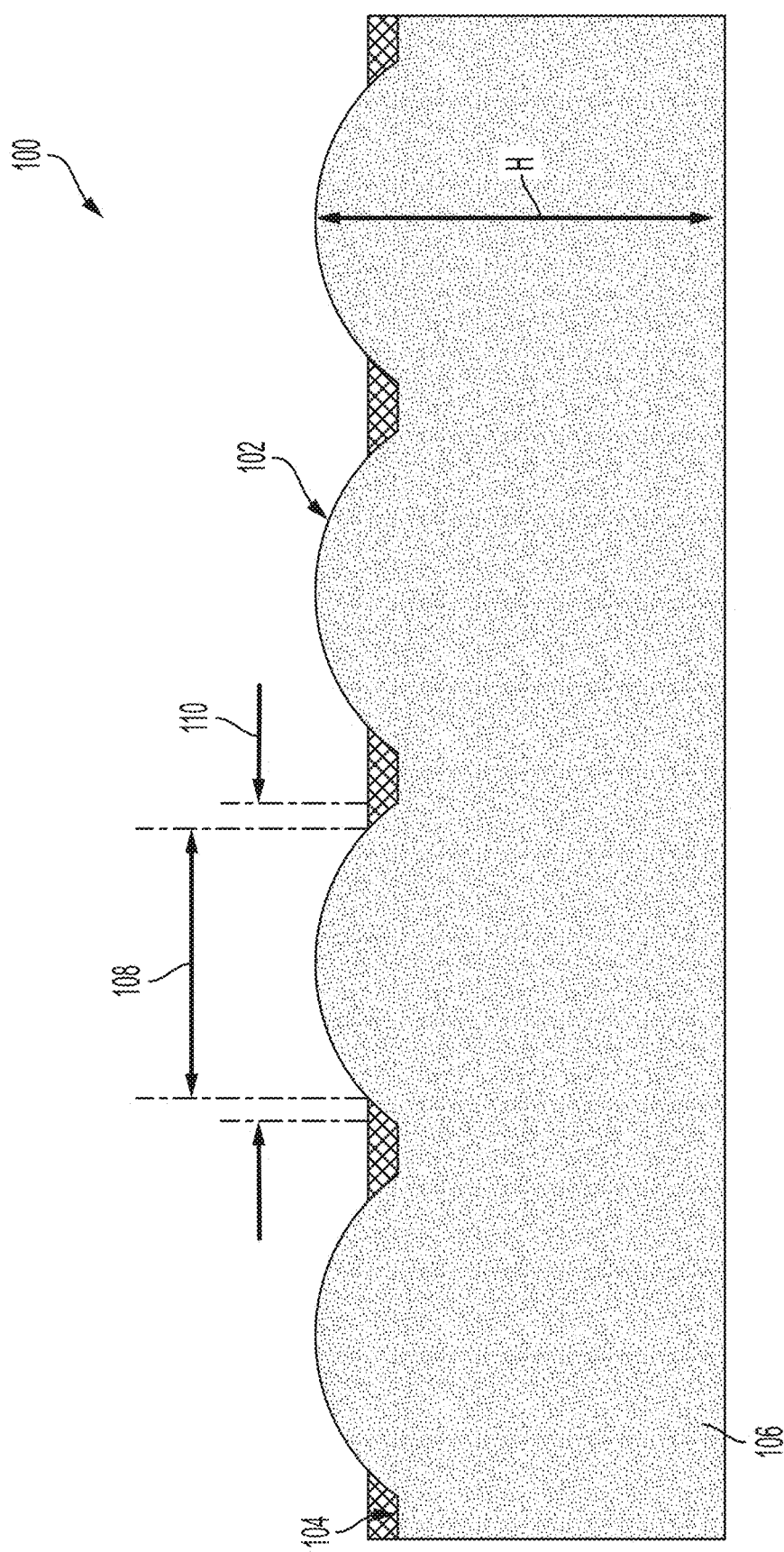
FIG. 1C is a cross section of a portion of the optical chip illustrated in FIGS. 1A and 1B, according to illustrative embodiments of the present disclosure.

It is contemplated that systems, devices, methods, and processes of the disclosure encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems according to certain embodiments of the present disclosure that consist essentially of, or consist of, the recited components, and that there are processes and methods according to certain embodiments of the present disclosure that consist essentially of, or consist of, the recited processing steps.

It should be understood that the order of steps or order for performing certain action is immaterial so long as operability is not lost or unless otherwise explicitly or implicitly stated. Moreover, two or more steps or actions may be conducted simultaneously.

Headers are provided for the convenience of the reader and are not intended to be limiting with respect to the claimed subject matter. Implementations, or portions thereof, from under one header may be used with or applied to implementations, or portions thereof, from under another header as will be clear to those of ordinary skill in the art.

The present disclosure provides, inter alia, systems and methods that can reduce or eliminate image artifacts that may otherwise be present in an image due to sample motion that occurs during imaging. A sample may be exposed to a user (e.g., in an open-top architecture) during imaging, for example being disposed on an open sample dish that is disposed on a transparent imaging window of an imaging system. Such a sample may be able to move during imaging. For example, certain biological samples, such as resected tissue samples, may relax during a period of time in which an image is acquired. Imaging artifacts may arise, for example, when an imaging system uses a parallel scanning approach, such as, for example, an imaging system that includes an array of micro optical elements that are used to image a sample. In such an example, sample motion may lead to discontinuities (e.g., noticeable lines) in an image at one or more boundaries between areas corresponding to different micro optical elements in an array.

Examples of Arrays of Micro Optical Elements and Imaging Systems

In some embodiments, an imaging system used to image includes an array of micro optical elements that may include one or more of refractive lenses, Fresnel zone plates, reflective objectives, and gradient-index (GRIN) lenses. An array of micro optical elements may be scanned over a scan pattern during imaging, for example by a scanning stage that includes an actuator. A scan pattern may have a size that corresponds to a size of a unit cell for a micro optical element in an array of micro optical elements (e.g., be squares of approximately equivalent size). In such a way, each micro optical element in an array of micro optical elements may scan an area corresponding to its unit cell in order to produce an image corresponding in size (e.g., having a size of the same order of magnitude) as the array of micro optical elements. A scan pattern may include a series of sequential positions (e.g., disposed in an array, such as a regular array) that are moved to sequentially during imaging. An array of sequential positions defining a scan pattern may generally be an M×N array where M=N or M≠N. Illumination light may be provided to a sample through an array of micro optical elements at a subset (e.g., all) of the sequential positions in a series (e.g., array). Back-emitted light may be collected from a sample with an array of micro optical elements at a subset (e.g., all) of the sequential positions in a series (e.g., array), for example when an imaging system is a fluorescence microscope, such as a confocal microscope.

In some embodiments, an imaging system is disposed in an operating room and used during surgical procedures (e.g., diagnostic procedures or treatment of a diagnosed illness). In some embodiments, systems are used and/or methods are performed intraoperatively.

An array of micro optical elements may be disposed on a surface of an optical chip. For example, the micro optical elements may be disposed on a surface of a substrate of an optical chip. In some embodiments, an optical chip includes an array of micro optical elements attached to a holder around the periphery of the array (e.g., is not disposed on a substrate). Generally, the outer perimeter of an optical chip can have any shape. In some embodiments, an optical chip is a rectangle (e.g., a square or a non-square). For example, in some embodiments, an array of micro optical elements is integral with a substrate of an optical chip. An array of micro optical elements can be non-integral, but attached to a substrate of an optical chip. An array of micro optical elements may include at least 25,000 micro lenses (e.g., with a radius of curvature (ROC) of between 200 µm and 300 µm. An absorptive and/or reflective layer may be provided on an optical chip between micro optical elements in an array (e.g., to act as an aperture). An optical chip may be made of fused silica. Micro optical elements may be arranged in a regular array on an optical chip (e.g., a square lattice). In some embodiments, an array of micro optical elements has a pitch of from 100 µm to 500 µm (e.g., from 200 µm to 300 µm). In some embodiments, an optical chip has a non-regular array of micro optical elements, for example, having a different pitch in an x-direction and a y-direction. In some embodiments, an optical chip has a high numerical aperture for high resolution imaging and more efficient background rejection.

In some embodiments, an array of micro optical elements is not part of an optical chip. For example, in some embodiments, an array of micro optical elements is an array of discrete objectives, for example that are mounted (e.g., to each other or to a physical support) in a fixed relative position.

In some embodiments, an array of micro optical elements is a regular array and a pitch of micro optical elements in the array in a first direction equals a pitch of micro optical elements in the array in a second direction that is perpendicular to the first direction. For example, micro optical elements may be arranged in a square lattice. In some embodiments, each micro optical element of an array of micro optical elements has at least one convex surface. For example, each micro optical element may be a planoconvex lens or a biconvex lens. A convex surface of each micro optical element may have a shape obtained by the revolution of a conic section (e.g., with a radius of curvature of between 200 µm and 300 µm). In some embodiments, each micro optical element in an array of micro optical elements focuses light onto an area (spot) smaller than a pitch (e.g., the pitch) of the array. In some embodiments, micro optical elements in an array of micro optical elements collectively focus onto a common focal plane. For example, each element of an micro optical element array may focus onto a single point on the common focal plane.

FIG. 1A and FIG. 1B schematically illustrate two views of illustrative optical chip 100 that includes an array of micro optical elements 102, which may be used in systems disclosed herein and/or to perform methods disclosed herein. FIG. 1A shows a plan view of the entirety of optical chip 100 (individual micro optical elements and optional reflective/absorptive layer are not shown in FIG. 5A). Optical chip 100 has a rectangular cross section having dimensions W and L (i.e., with W≠L). In some embodiments, W=L. Optical chip 100 has high parallelism with edges of optical chip 100 having a parallelism of better than about ±0.250 mrad (e.g., no more than or about ±0.125 mrad). FIG. 5B shows a portion of optical chip 100 including a portion of array of micro optical elements 102. An array of micro optical elements disposed on a surface of optical chip 100 may include at least 1,000 micro optical elements, at least 5,000 micro optical elements, at least 10,000 micro optical elements, at least 20,000 micro optical elements, at least 30,000 micro optical elements, at least 50,000 micro optical elements, at least 60,000 micro optical elements, or at least 100,000 micro optical elements. Array of micro optical elements 102 is highly parallel relative to edges of optical chip 100. Array 102 has a parallelism relative to edges of an optical chip of better than about ±0.250 mrad (e.g., no more than or about ±0.125 mrad). Array 102 is a regular array. In some embodiments, an array of micro optical elements is non-regular. Dashed box 112a shows an example of a unit cell of a micro optical element in array 102. Dashed box 112b shows an example of a unit cell of a micro optical element in array 102 drawn with a different origin than for dashed box 112a. In general, the selection of origin is arbitrary. Crosshairs in each micro optical element of array 102 indicate the respective centers of the micro optical elements.

FIG. 1C shows a diagram of a cross section of a portion of an illustrative optical chip 100. Optical chip 100 includes a substrate 106 and an array of micro optical elements. Each micro optical element 102 is a convex microlens. The convex microlenses 102 are integral with the substrate 106 such that the substrate 106 and microlenses 102 are together one continuous material. For example, they may be formed simultaneously during fabrication. The thickness (H) of optical chip 100 can be taken as the distance between the top of the micro optical elements and the opposite surface of the substrate, as shown. Thickness of an optical chip may be less than 2.0 mm (e.g., less than 1.5 mm or about 1.5 mm). An optical chip may have a total thickness variation and/or total flatness deviation of less than 20 µm (e.g., less than less than 10 or less than 5 µm). Optical chip 100 is coated with a reflective layer 104 of chromium. Reflective layer 104 is disposed in inter-lens area between micro optical elements 102. It is understood that a reflective layer disposed in an inter-lens area may extend partially onto one or more lenses near the periphery of the lens(es) as shown in FIG. 1A and FIG. 1B. If a reflective layer 104 extends partially over micro optical elements near peripheries of the micro optical elements, a micro optical element diameter 110 is larger than a reflective layer aperture 108 formed by reflective layer 104.

Figure 25:
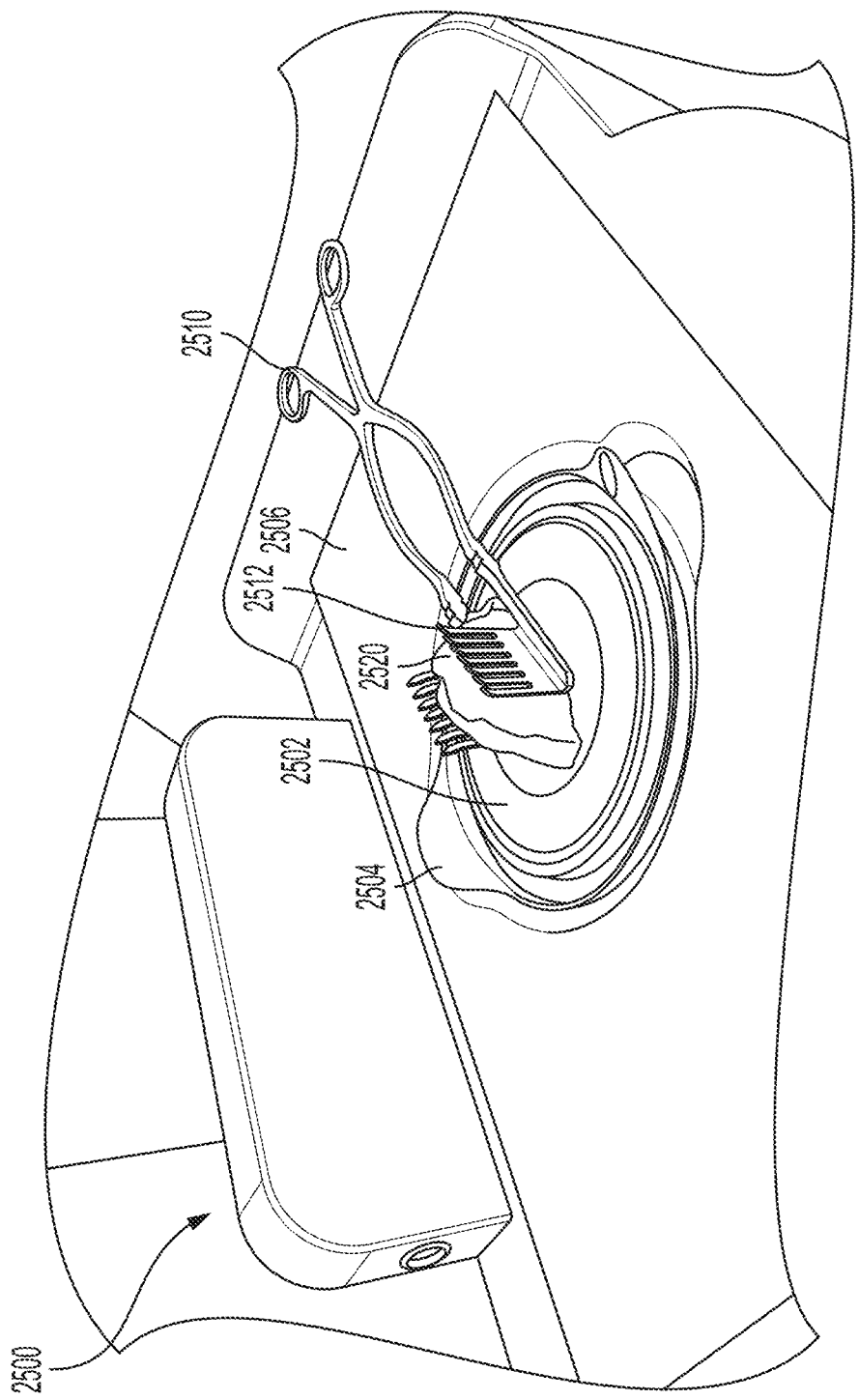
FIG. 25 is an image of an imaging system, according to illustrative embodiments of the present disclosure.

FIG. 2A is a schematic of illustrative imaging system 200 showing behavior of optics of the illustrative system during illumination of a tissue sample. Imaging system 200 may include features set forth herein and/or may be used to perform methods disclosed herein. FIG. 2B is a schematic illustrative imaging system 200 showing detection of back-emitted light from a sample by a detector. Referring now to FIG. 2A, a laser 218 that provides light with a wavelength that is between 450 nm and 490 nm provides an illumination beam to a focusing lens 216. The illumination beam passes through the focusing lens 216 and a first aperture 214 before being directed by a dichroic mirror 214. The dichroic mirror reflects the illumination beam onto a collimating lens 202. The illumination beam is collimated by collimating lens 202 and the collimated illumination beam propagates to an optical chip 222. The optical chip includes an array of micro optical elements. Micro optical elements in an array of micro optical elements may be refractive lenses, Fresnel zone plates, reflective objectives, GRIN lenses, or micro lenses. In certain embodiments, an optical chip includes an array of refractive micro lenses. The micro optical elements focus light from the collimated illumination beam onto a sample through an imaging window. In this case, a sample 228 is disposed on a disposable sample holder 226 that is mounted directly onto an imaging window 224. In some embodiments, a sample is disposed over an imaging window (e.g., on a sample dish) (e.g., without contacting the imaging window) during imaging. In some embodiments, sample holder 226 is not present and a sample is mounted directly on a transparent imaging window during imaging. Use of a sample dish may reduce or eliminate the need to clean (e.g., sterilize) a transparent imaging window when changing samples. FIG. 25 shows a sample dish 2504 mounted on a transparent imaging window 2502 with sample 2520 disposed therein, as an example of an imaging system 2500 that can be and/or is used with a sample dish 2502. Imaging system 200 may be similarly modified or designed.

Referring again to FIG. 2A, optical chip 222 is connected to a support of a scanning stage 220. Scanning stage 220 moves optical chip 222 along a scan pattern during imaging using a controller and an actuator connected to the support. Each micro optical element of optical chip 222 produces a tight focus (e.g., a small spot) of light from the collimated illumination beam on or in a sample during imaging on a common focal (imaging) plane that is on or in the sample.

FIG. 2B is a schematic of illustrative imaging system 200 showing behavior of the optics shown in FIG. 2A during detection. Light from the collimated illumination beam focused onto the sample 228 by the array of micro optical elements in the optical chip 222 produces light (e.g., fluorescence or luminescence) in the sample 228 that is back-emitted through imaging window 224 towards optical chip 222. Back-emitted light is then collected by the micro optical elements in the array in optical chip 222 and directed towards a detector 212. Back-emitted light passes through dichroic mirror 204 as it is within the transmission band of the mirror. Back-emitted light then passes through a second aperture 206 and is collimated by an imaging lens 208. The collimated back-emitted light passes through an emission filter 210 and then onto a detector 212. Detector 212 is a CMOS camera that includes an array of detector elements (e.g., pixels in the camera) that each receive back-emitted light from a micro optical in the array of optical elements in optical chip 222. An opaque enclosure may be disposed about an optical path of the back-emitted light that passes through filter 210 in order to block ambient (e.g., stray) light from being incident on detector 212.

An imaging system may be used for in-operating-theatre imaging of fresh tissue resected during surgery (e.g., cancer surgery). In some embodiments, an imaging system is operable to image a portion of a sample in less than 10 minutes (e.g., less than 5 minutes, less than 3 minutes or less than 2 minutes). In some embodiments, a system is operable to image a portion of the sample in less than 2 minutes (e.g., less than 90 seconds or less than 1 minute). IN some embodiments, the portion of the sample has an area of at least 10 cm$^2$ (e.g., at least 12 cm$^2$, at least 15 cm$^2$, or at least 17 cm$^2$). In some embodiments, a sample has a volume of no more than 10 cm×10 cm×10 cm and the system is configured to image a full outer surface of the sample in an imaging time of no more than 45 minutes (e.g., no more than 30 minutes).

Imaging systems that can be used in accordance with (e.g., to perform) certain embodiments of the present disclosure are discussed in U.S. Pat. Nos. 10,094,784 and 10,539,776, each of which is hereby incorporated herein in its entirety. Sample dishes that can be used in certain embodiments of the present disclosure are discussed in U.S. patent application Ser. No. 16/146,518, filed on Sep. 28, 2018, the disclosure of which is hereby incorporated by reference herein in its entirety. Samples may be stained prior to imaging. For example, samples may be stained using a staining agent solution disclosed in U.S. patent application Ser. No. 16/806,555, filed on Mar. 2, 2020, the disclosure of which is hereby incorporated by reference herein in its entirety.

Source of Imaging Artifacts in Parallel Imaging Systems

An imaging system used to acquire an image may be a parallel imaging system. For example, an imaging system may acquire pixels from all tiles simultaneously while imaging. For example objectives may be micro optical elements in an array of micro optical elements. Imaging a moving sample with such an imaging system may also produce images containing sample motion artifacts that will manifest as discontinuities between the tiles, for example if a conventional raster scan is used.

FIG. 3 shows a conventional bidirectional raster scan pattern defined by an array of sequential positions that is used with single objective or parallel imaging systems. The scan pattern shown in FIG. 3 corresponds to a physical pattern made during scanning by a single micro optical element in an array of micro optical elements of a parallel imaging system. Thus, each micro optical element will follow the same scan pattern, but in different physical locations. Because of the nature of the raster scan pattern, there is a fast scan axis and a slow scan axis. The scan pattern of FIG. 3 is a bidirectional raster scan pattern of M×N scan steps of equal distances along the fast and the slow scan axes. Assuming that the system takes dt time for each step, regardless of the direction, it will take a time of M×dt to complete one line of scan along the fast scan axis. The time difference between two tiles along the fast scan axis (in FIG. 3, two horizontally adjacent tiles) is approximately M×dt. However, it will take a time of M×N×dt to complete the full scan over the scan area. The time difference between two tiles along the slow axis is therefore approximately M×N×dt (in FIG. 3, two vertically adjacent tiles). Therefore, the time difference between horizontal edge rows is significantly larger than the time difference between vertical edges.

Figure 4:
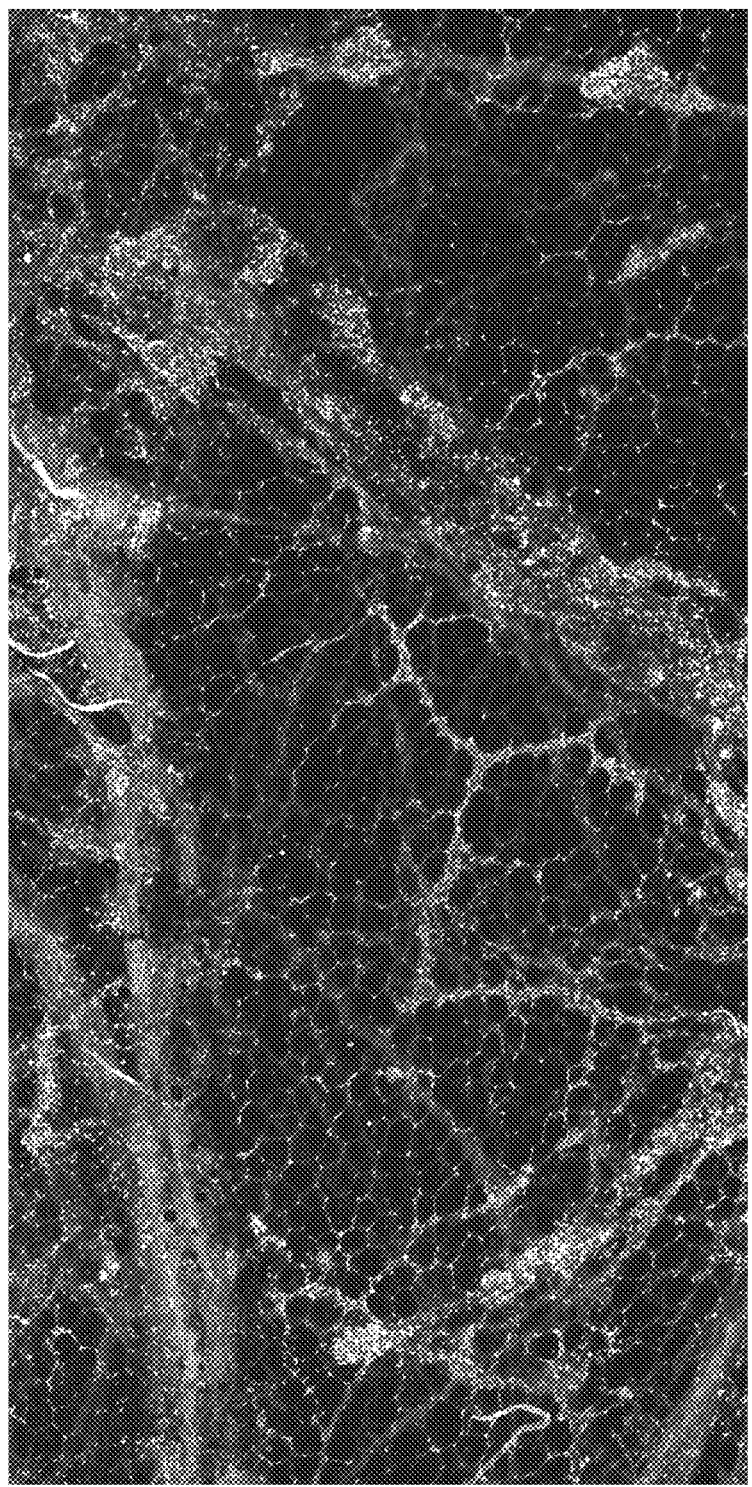
FIG. 4 is an image acquired by an imaging system in which no noticeable sample motion occurred during acquisition.
Figure 5:
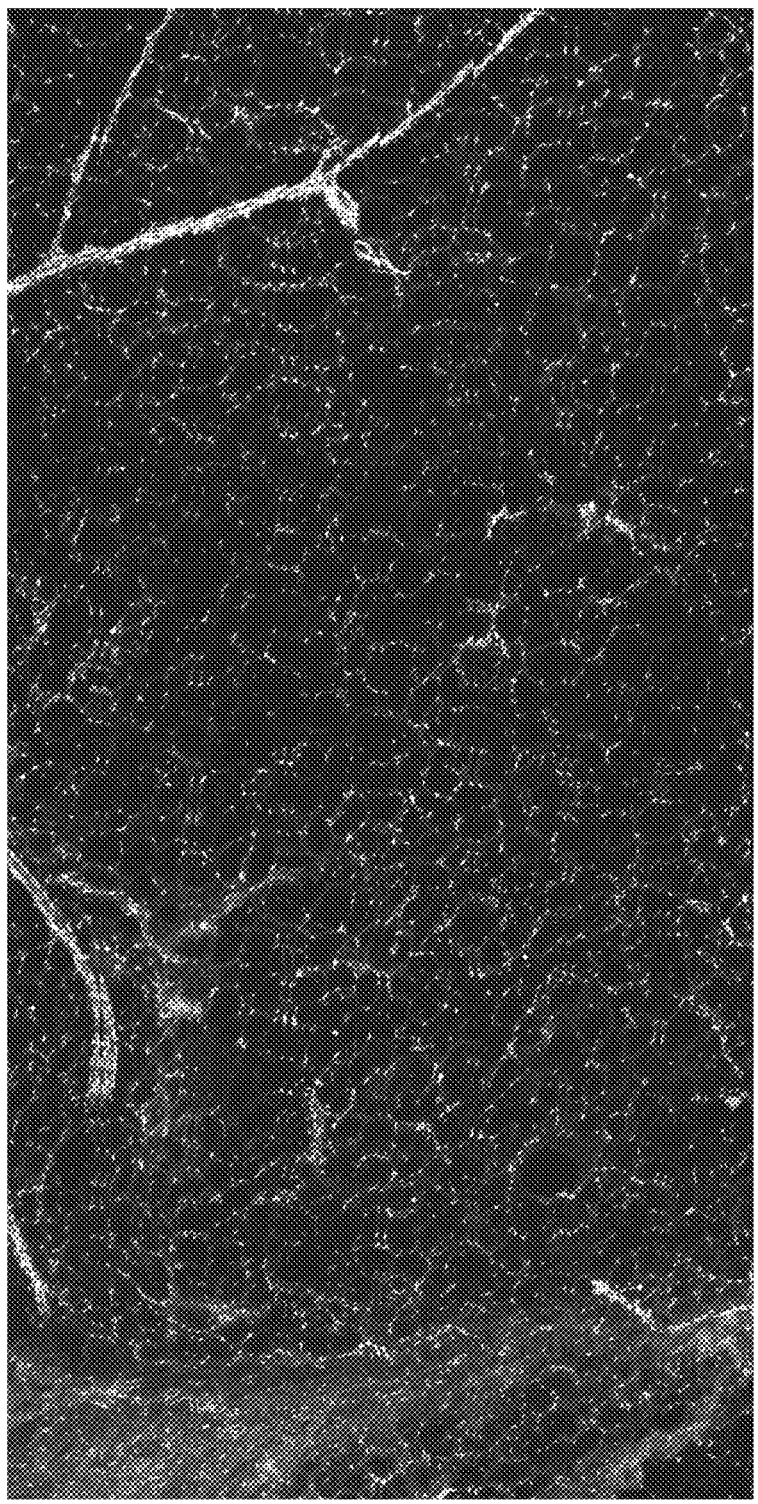
FIG. 5 is an image acquired by an imaging system in which some sample motion occurred during acquisition.
Figure 6:
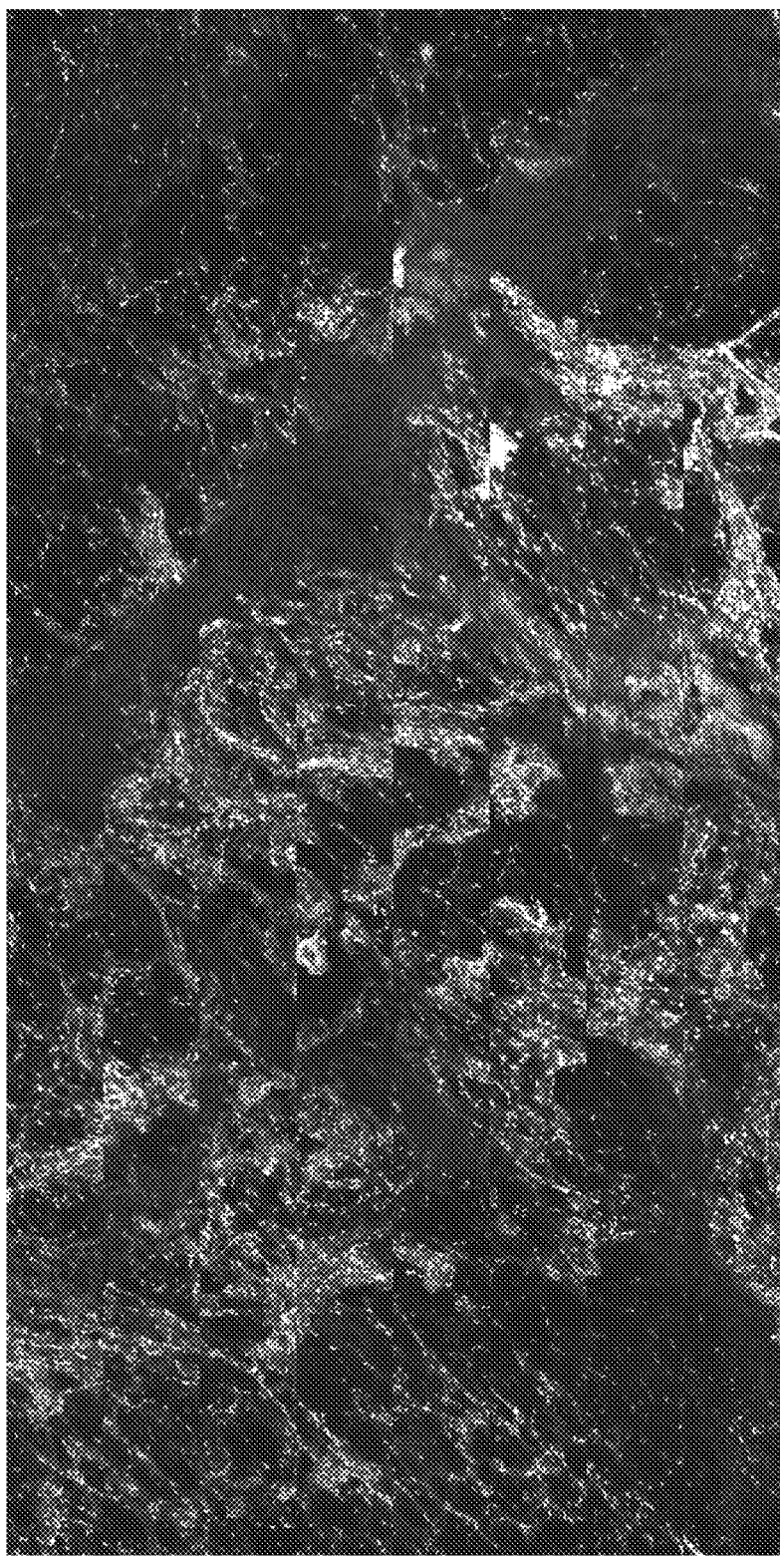
FIG. 6 is an image acquired by an imaging system in which a relatively large amount of sample motion occurred during acquisition.

For a bidirectional raster scan used in a parallel imaging system, as shown in FIG. 3, even when a sample does move somewhat during imaging, there can be almost no discontinuities (sample motion artifacts) across the tiles along the fast scan axis if M×dt is sufficiently small compared to the time it takes the sample to move over a distance comparable to or larger than one scan step. For example, M=125 and dt=2 ms can be sufficiently small compared to the time it takes a resected breast lump sample to move over a distance of about 2 micrometers. For example, while FIGS. 4-6 show different degrees of artifacts from sample motion along the slow axis, no sample motion artifacts are observed along the fast scan axis (i.e., between any two horizontally adjacent tiles). FIGS. 4-6 show images that are about 4 mm×2 mm in size and comprise an array of 16×8 tiles (e.g., where formed by scanning an array comprising 16×8 micro optical elements).

With reference still to FIG. 3, M×N×dt is more likely to be relatively large compared to the time it takes a sample to move over a distance comparable to or larger than one scan step. For example, if M=125 and dt=2 ms, an imaging system can complete imaging in about 31.25 seconds. In such an imaging set-up, if by relaxation or by motion induced by its own weight, a sample moves significantly less than 10 micrometers over about 30 seconds, no discontinuities may be observed along the slow scan axis between neighboring tiles (i.e., between any two vertically adjacent tiles) (see FIG. 4). In such an imaging set-up, if by relaxation or by motion induced by its own weight, a sample moves by about 10 micrometers over about 30 seconds, a moderate discontinuity may be observed along the slow scan axis across the border of two neighboring tiles (see FIG. 5). In such an imaging set-up, if by relaxation or by motion induced by its own weight, a sample moves by about 100 micrometers over about 30 seconds, a large discontinuity may be observed along the slow scan axis across the border of two neighboring tiles (see FIG. 6). Using different scan patterns that differ from the conventional bidirectional raster scan pattern of FIG. 3 can reduce or eliminate the discontinuities observed in FIGS. 5 and 6 even when a sample moves comparably large amounts during imaging (see "Scan Patterns" section below).

Optimized Time and Resolution for Imaging

In general, the longer the time used to image a sample with an imaging system, the more sensitive the system will be to sample motion artifact, since the sample will move more (in absolute terms) during longer imaging acquisition times than shorter imaging acquisition times. In general, the finer the resolution used in an imaging system, the more visible sample motion artifacts will appear (e.g., will appear sharper). During imaging, a sample motion over a distance of less than a system's chosen resolution for a particular image will be unnoticeable. For a given resolution, the shorter the imaging time, and thus amount of sample motion, the less visible motion artifacts will be. For a given imaging time, and thus amount of sample motion, the better the image resolution, the more visible motion artifacts will be. In practice, an imaging system may not have access to any combination of resolution and imaging time. For typical point-scanning imaging systems, the relation between the resolution and the imaging time is quadratic: improving the resolution by a factor 2 increases the imaging time by a factor 4. Therefore, some combinations of imaging time and resolution are more suitable to prevent observing sample motion artifacts in the images. For example, when imaging tissue samples (e.g., fresh tissue samples excised during surgery), an imaging time of 30 seconds and an image resolution of 2 microns will often lead to sample motion artifacts in images based on typical imaging. On the contrary, an imaging time of 5 seconds and an image resolution of 10 microns will almost never lead to sample motion artifacts in the images. There is no sharp boundary between combinations of imaging times and resolutions that are prone to sample motion artifacts and those that are not, but the above referenced combinations generally represent bounds on acceptable combinations for certain types of samples.

Of course, different samples (e.g., samples of different nature, samples made of different tissues, or samples of different shapes) may have different motion characteristics. For example, flexible (or so-called "soft") tissues (e.g., a breast lump) may have a longer characteristic relaxation time than rigid (or so-called "hard") tissues (e.g., a bone). The best optimization between imaging time and resolution will depend, among other things, on the application (e.g., which features are desired to be seen in an image), on the sample type (e.g., material, size, and/or weight), and on the imaging system characteristics (e.g., characteristic(s) of an array of micro optical elements).

Figure 7:
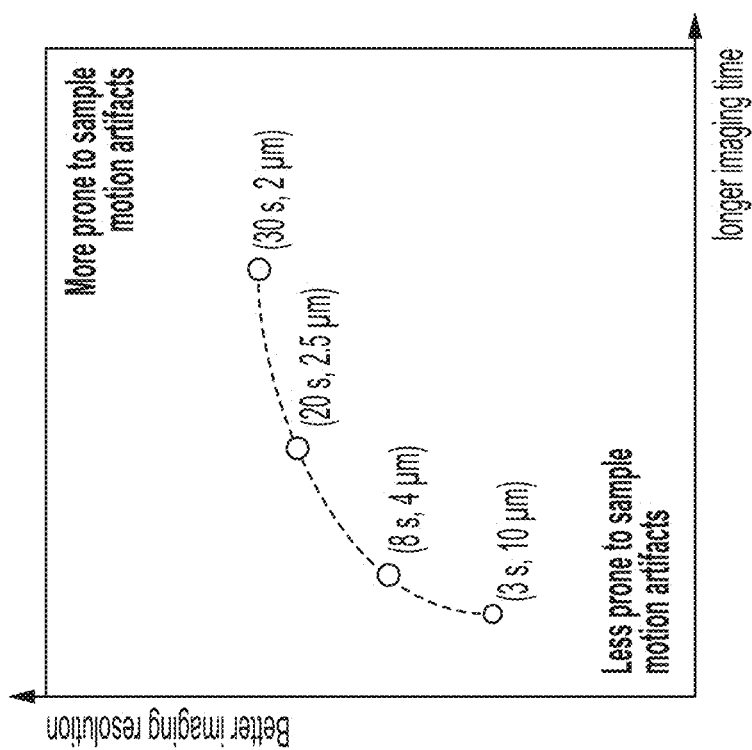
FIG. 7 is a plot showing representative optimization between image resolution and image time to mitigate sample motion artifacts, according to illustrative embodiments of the present disclosure.

In some embodiments, there is a 'sweet' area between an image resolution of 2 μm and 10 μm, which allows imaging of cells and cell nuclei in a sample, while allowing a possibility to operate with an imaging time below 30 seconds. For an application where 10 microns resolution is enough, an imaging system with an imaging time of 5 seconds would be, in many cases, free of sample motion artifacts. For applications requiring a better resolution, reducing imaging time below 10 seconds of imaging time with an image of resolution of 5 microns or better would be a good compromise between image information content and sample motion artifacts. An image with resolution of 2.5 μm with an imaging time of around 19 seconds would express significantly less motion artifacts than an image with resolution of 2 μm and an imaging time of 30 seconds. An image with resolution of 4 μm with an imaging time of around 7.5 seconds would be several times (e.g., at least 4 times) better in terms of motion artifact magnitude than an image with resolution of 2 μm and an imaging time of 30 seconds. See FIG. 7 for a plot visually depicting optimization between imaging resolution and imaging time.

The present disclosure recognizes that in some embodiments of imaging with an imaging system (e.g., with a parallel imaging system that uses, for example an array of micro optical elements), reducing the ratio ($Q=t/r$) of the imaging time (t), in seconds, over the image resolution (r), in μm, reduces the amount and magnitude of motion artifacts in the images. When imaging fresh tissue samples (e.g., fresh breast tissue samples excised during surgery), a ratio Q<1 provides a reasonable assurance that images would rarely present motion artifacts noticeable by a user, and that observed motion artifacts would not materially affect image interpretation by a user (such artifacts being referred to for this purpose as "minor" motion artifacts). A ratio 1<Q<2 would likely result in the presence of some minor motion artifacts and rare presence of motion artifacts that would be considered by the skilled user to complicate interpretation of the image (such artifacts being referred to for this purpose as "major" motion artifacts). A ratio 2<Q<5 would likely result in the presence of many minor motion artifacts, some major motion artifacts and rare presence of motion artifacts that may adversely impact image interpretation (e.g., risk accurate interpretation of the image) (such artifacts being referred to for this purpose as "critical" motion artifacts). A ratio of 5<Q<20 would likely result in the presence of many minor and major motion artifacts, as well as some critical motion artifacts. A summary of these conditions is included in Table 1. While lower Q ratio is better in terms of artifacts, it also corresponds to higher imaging times, which may be longer than acceptable for a given application. Accordingly, in some embodiments imaging is performed by an imaging system (e.g., comprising an array of micro optical elements) in a $1 \leq Q \leq 5$ (e.g., $2 \leq Q \leq 5$) condition. In some embodiments, imaging is performed by an imaging system in a $Q \leq 5$ (e.g., $Q \leq 2$ or $Q \leq 1$) condition. In some embodiments, a test image is acquired by an imaging system in a $5 \leq Q$ (e.g., $10 \leq Q$) condition.

TABLE 1

| | Minor | Major | Critical |
|---|---|---|---|
| Q < 1 | Rare | None | None |
| 1 < Q < 2 | Some | Rare | None |
| 2 < Q < 5 | Many | Some | Rare |
| 5 < Q < 20 | Many | Many | Some |
| Q > 20 | Many | Many | Many |

In some embodiments, a method of imaging a sample using an array of micro optical elements includes selecting an imaging time and an imaging resolution based, at least in part, on one or more features of the sample to be resolved (e.g., cell in the sample, nuclei of the cells, or organelles of the cells). In some embodiments, the imaging time is from 5 seconds (s) to 30 s and the imaging resolution is from 10 μm to 2 μm. Subsequently, an image of the sample may be acquired (e.g., automatically) in part by scanning the array of micro optical elements over a scan pattern. In some embodiments, the scan pattern has an area corresponding to the area of a unit cell of a micro optical element in the array. The sample may be a biological sample (e.g., a resected tissue sample) (e.g., a stained biological sample). In some embodiments, the imaging time is selected based on the imaging resolution. In some embodiments, the imaging resolution is selected based on the imaging time. In some embodiments, the imaging time is no more than 10 seconds and the imaging resolution is 5 μm or better. In some embodiments, selecting the imaging time and the imaging resolution is further based, at least in part, on a material of the sample.

Scan Patterns

Figure 14:
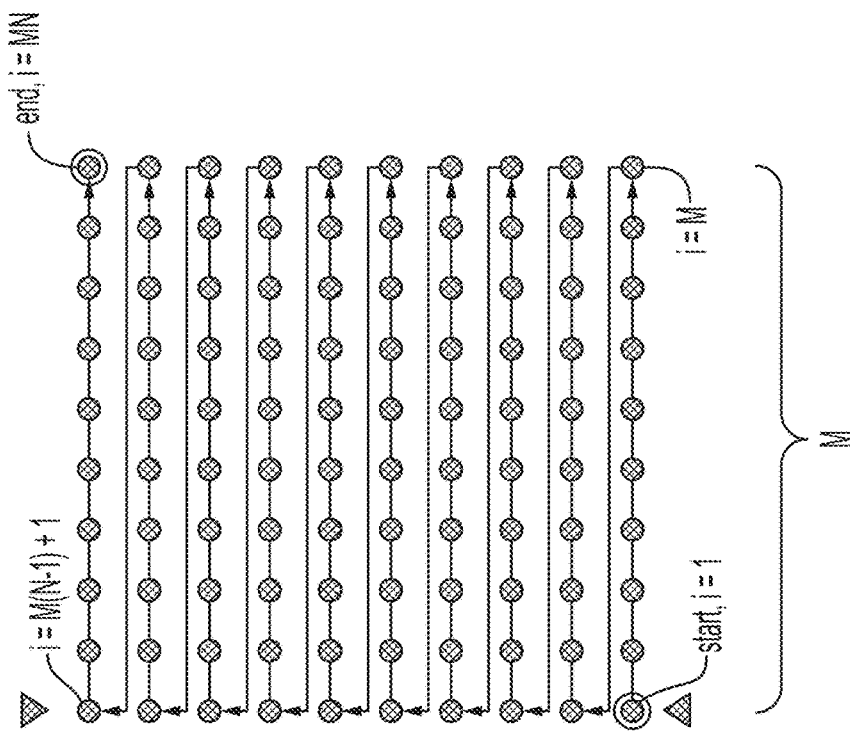
FIG. 14 illustrates relative acquisition times for various points in a conventional unidirectional raster scan pattern, according to illustrative embodiments of the present disclosure.
Figure 13:
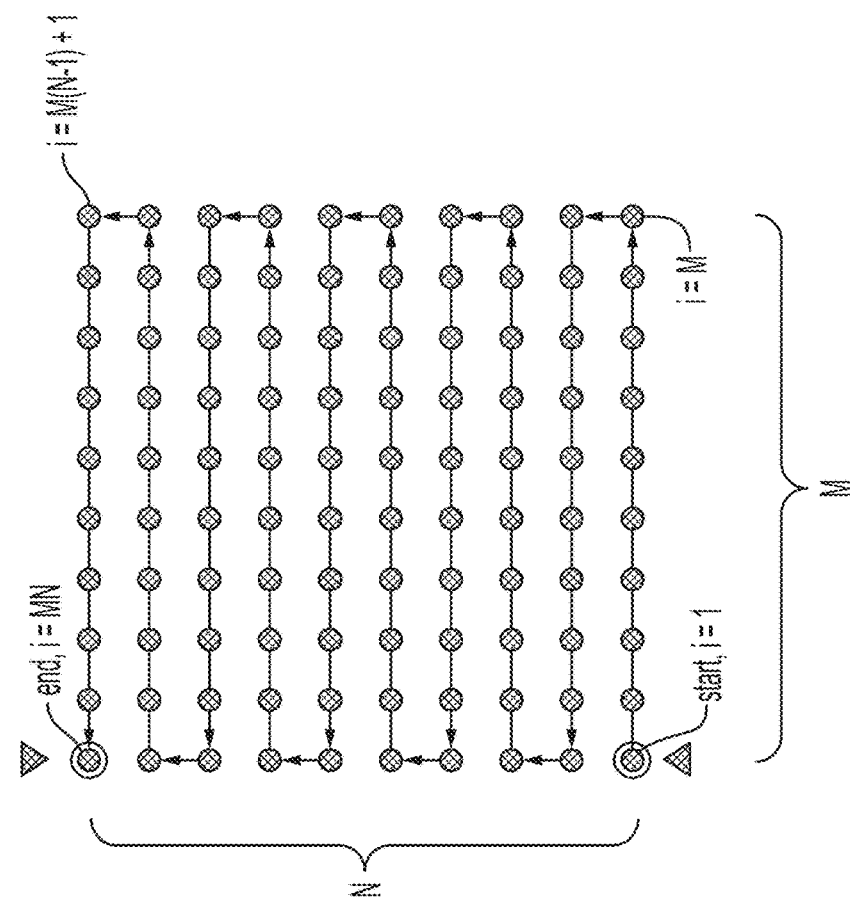
FIG. 13 illustrates relative acquisition times for various points in a conventional bidirectional raster scan pattern, according to illustrative embodiments of the present disclosure.
Figures 15, 16:
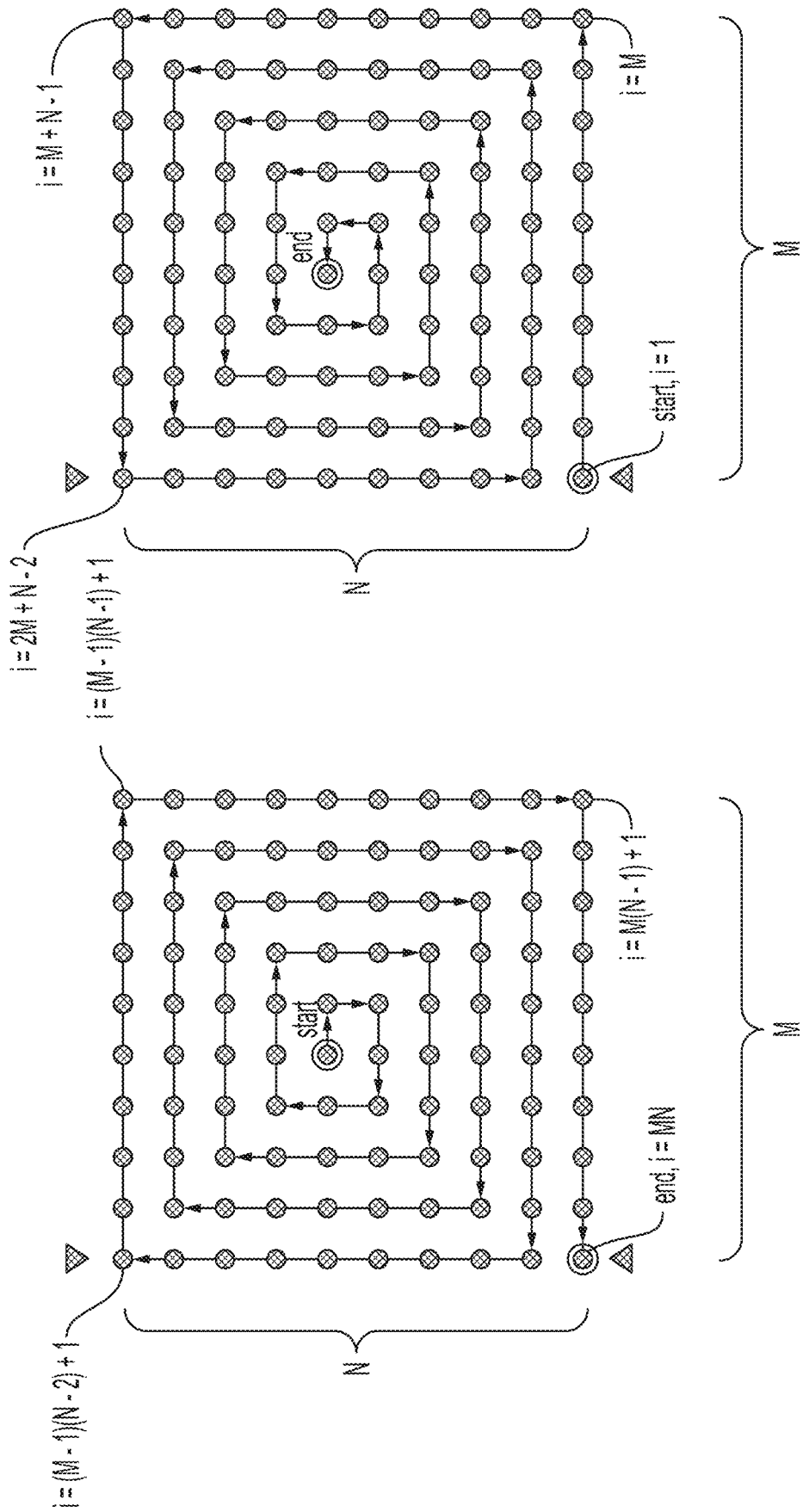
FIG. 15 illustrates relative acquisition times for various points in an outward spiral scan pattern, according to illustrative embodiments of the present disclosure.
FIG. 16 illustrates relative acquisition times for various points in an inward spiral scan pattern, according to illustrative embodiments of the present disclosure.

Conventional raster scans (whether bidirectional, e.g., as in FIG. 3, or unidirectional, e.g., as in FIG. 14) have a fast and slow scan axis (e.g., as labelled in FIG. 3). Whether or not a time step for each scan point is constant (e.g., represented as "dt"), the time at which data acquisition occurs for the last row of positions in a conventional raster scan is very late relative to the total acquisition time for the image. For example, as shown in FIG. 3, for an M×N array, the final position in the scan pattern is acquired at (M×N)dt and the first position in the row is acquired at (M(N−1)+1)dt, whereas the first position in the pattern is acquired at dt and the last position in the first row is acquired at M×dt. Thus, a time difference of (M(N−2)+1)dt elapses between acquiring the first row and beginning to acquire the final row. For parallel scanning systems (e.g., including an array of micro optical elements), where each objective (e.g., micro lens) is scanned over the scan pattern simultaneously, tiles that are adjacent in the slow scan axis direction (vertically adjacent in the case of FIG. 3) will have a large time discontinuity between when perimeter (or "border") rows are acquired in the adjacent tiles. If sample motion is occurring, especially if sample motion is large relative to the scan pattern size and image acquisition time, large discontinuities may occur in an image at the intersection of adjacent tiles (e.g., as shown in FIG. 5 or FIG. 6) that may make reading an image (e.g., for diagnostic purposes) difficult. Such artifacts may appear even when only minor artifacts (or none at all) occur along the intersections of adjacent tiles in the fast scan axis direct (horizontally adjacent in the case of FIG. 3), because the acquisition time difference between adjacent pixels (positions in the scan pattern in the adjacent tiles) can be significantly less ((M−1)dt in the case of FIG. 3). Image artifacts can be even more significant for higher resolution scans that have more scan positions in the scan pattern used (possibly unless the acquisition time step is correspondingly lowered).

By using different scan patterns (e.g., that lower the average position of perimeter positions and/or that scan perimeter positions earlier) to scan parallel objectives (e.g., an array of micro optical elements), acquisition time differences between perimeter rows or columns in adjacent tiles of an image can be reduced. Such a reduction can reduce or eliminate noticeable (e.g., to a user) image artifacts resulting from sample motion. For a constant time step (which is typically used in order to promote intensity uniformity across an image), each pair of sequential positions in a scan pattern will have a constant time difference, dt. However, by tending to have all adjacent (and/or next nearest neighbor) positions be acquired closer together, sample motion can be effectively 'hidden' within each tile. Slight discontinuities (e.g., intensity variations) may become less noticeable.

Figure 8:
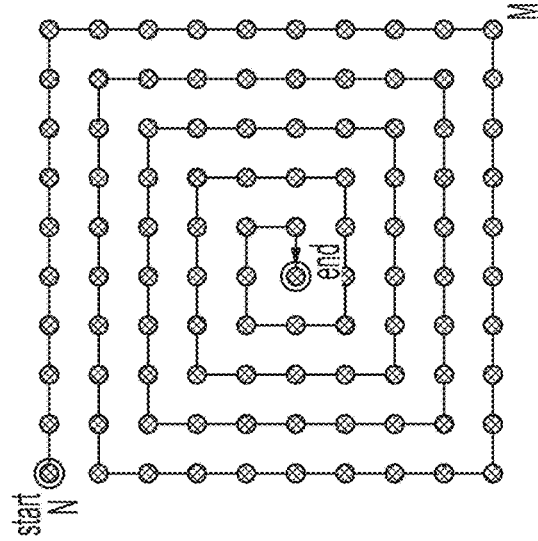
FIG. 8 illustrates an outward spiral scan pattern, according to illustrative embodiments of the present disclosure.
Figure 9:
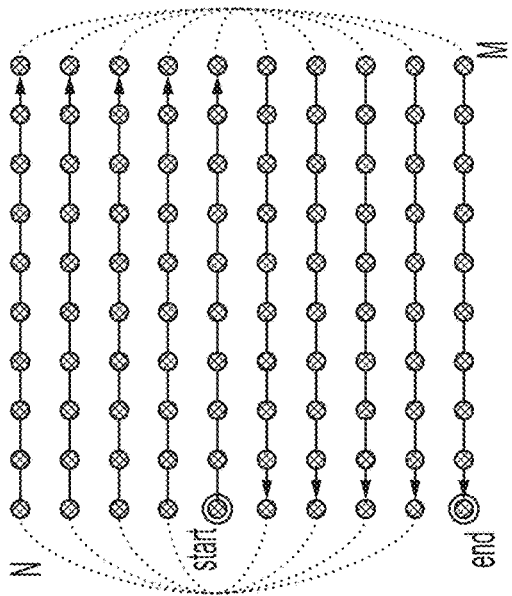
FIG. 9 illustrates an inward spiral scan pattern, according to illustrative embodiments of the present disclosure.

Certain examples of scan patterns that can be used to reduce discontinuities at tile borders by reducing acquisition time differences are given in FIGS. 8-11. FIGS. 8 and 9 show two versions of a "spiral" scan pattern where the perimeter positions are either acquired first or last, depending on whether an outward spiral (FIG. 8) or an inward spiral (FIG. 9) is used. Spirals with offset starting or end points can also be used. In contrast to conventional raster scans, the start and end position in each of the spirals is much closer together. In some embodiments, a start position and end (or "final") position of a scan pattern are separated by no more than two thirds (e.g., no more than one half) of a length and no more than two thirds (e.g., no more than one half) of a width of the scan pattern. Sometimes, sample motion decreases with time (e.g., when caused by a relaxation mechanism). In at least some such cases, an outward spiral scan pattern (e.g., with a starting point in a center of an scan pattern array) is particularly well suited to reducing or eliminating discontinuities in an acquired image, since it scans over larger distances on the edges at the end, when the rate of sample motion has decreased more than when image acquisition started.

Figure 10:
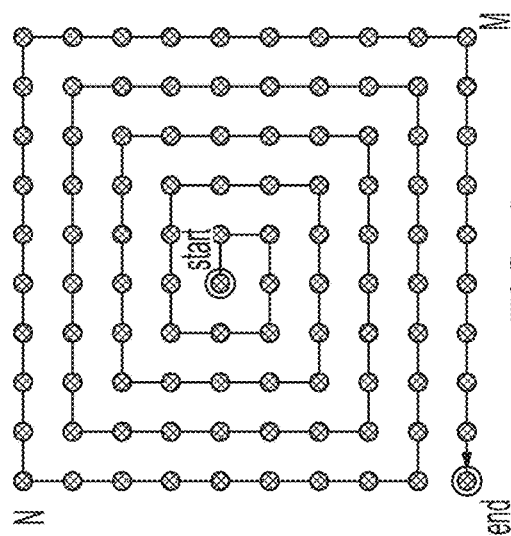
FIG. 10 illustrates an inward bidirectional alternating rows scan pattern where the first row is the top row, according to illustrative embodiments of the present disclosure.
Figure 11:
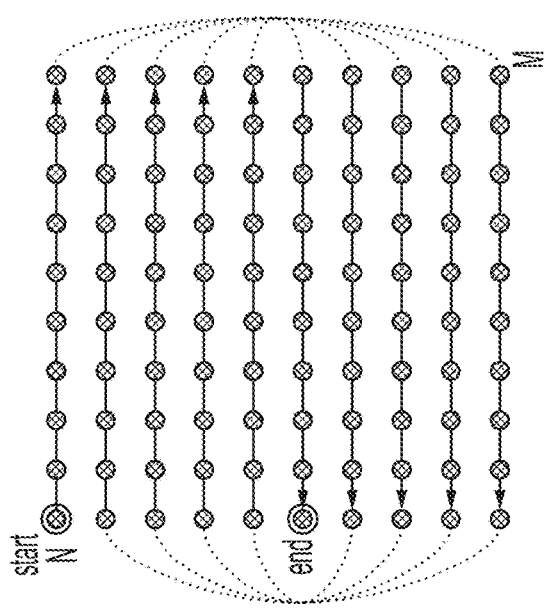
FIG. 11 illustrates an outward bidirectional alternating rows scan pattern where the first row is the middle row, according to illustrative embodiments of the present disclosure.
Figure 44:
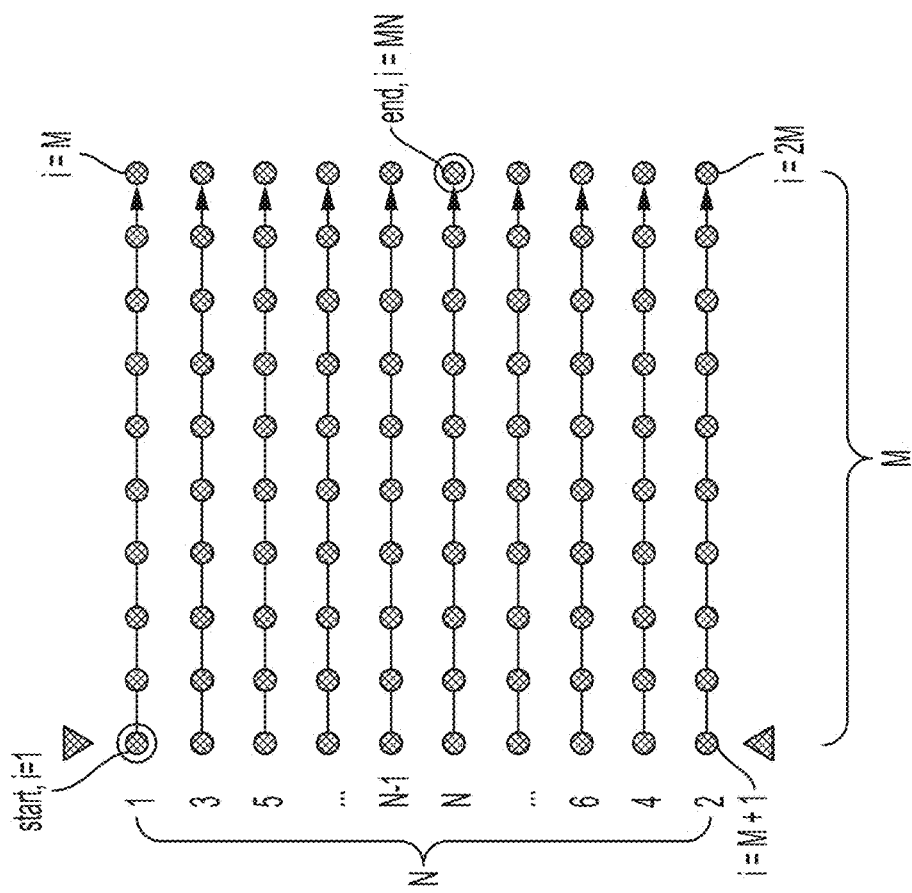
FIG. 44 illustrates an inward unidirectional alternating rows scan pattern where the first row is the top row, according to illustrative embodiments of the present disclosure.
Figure 43:
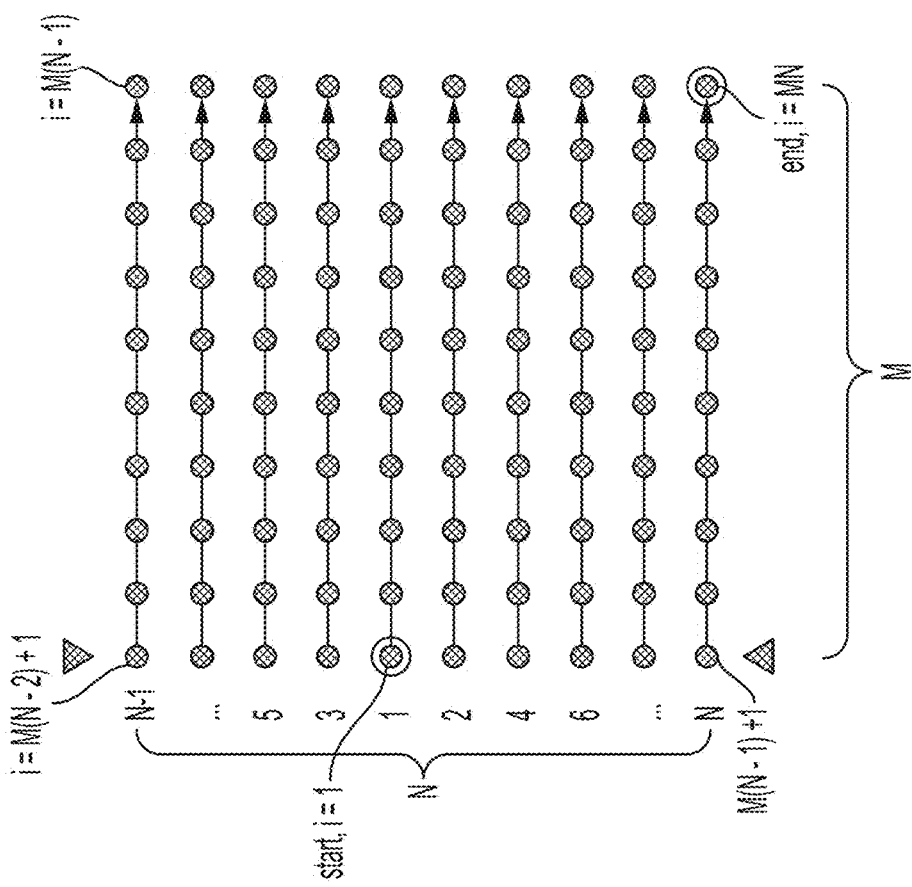
FIG. 43 illustrates an outward unidirectional alternating rows scan pattern where the first row is the middle row, according to illustrative embodiments of the present disclosure.

An alternative type of scan pattern that can be used to reduce acquisition time difference is using an "alternating rows" approach, examples of which are illustrated in FIGS. 10, 11, 43, and 44. FIGS. 10 and 11 illustrate bidirectional alternating rows scan patterns. FIG. 43 and FIG. 44 illustrate unidirectional alternating rows scan patterns. The starting row can be either somewhere interior (as in FIG. 11 or FIG. 43, where the middle row is the starting row) or at the edge (as in FIG. 10 or FIG. 44, where the top row is the starting row). In FIG. 10 and FIG. 44, rows are alternated starting with the top-most row, then the bottom-most row, then the second top-most row, then the second bottom-most row, and so forth. In FIG. 11 and FIG. 43, rows are alternated starting with the middle row, then the adjacent row below, then the adjacent row above, then the next most adjacent row below, then the next most adjacent row above, and so forth. Thus, in some embodiments, each row that is not first or last is spatially separated from its temporally adjacent rows by at least one other row. For example, in FIG. 10 and FIG. 44, the second row acquired is the spatially bottom row and the third row acquired is the second from the top spatially (and thus spatially separated by the fourth through tenth acquired rows). As another example, in FIG. 11 and FIG. 43, the second acquired and third acquired rows are spatially separated by the first acquired row. In some embodiments, a starting position of a scan pattern is in an interior row and a final position is in an exterior row and, optionally, each successive row is no closer to the interior row than an immediately preceding row. Sometimes, sample motion decreases with time (e.g., when caused by a relaxation mechanism). In at least some such cases where the time to travel from one scan row to the next depends on the distance between the two rows, an outward "alternating rows" scan pattern (e.g., with a starting row somewhere interior) is particularly well suited to reducing or eliminating discontinuities in an acquired image, since it scans over larger distances on the edges at the end, when the rate of sample motion has decreased more than when image acquisition started. In some embodiments, a starting position of a scan pattern is in an exterior row and a final position is in an interior row and, optionally, each successive row is no further from the interior row than an immediately preceding row.

By keeping more perimeter positions in a scan pattern closer together in the sequence of positions that constitute a scan pattern, acquisition time discontinuities between adjacent tiles can be reduced. In some embodiments, at least a third (e.g., at least half, or at least three quarters) of the positions in a perimeter of a scan pattern are a set of successive positions in the scan pattern (e.g., as shown in FIGS. 8-11). The width and length may be taken as perpendicular directions (e.g., if the scan pattern is a rectangular array of positions). This contrasts with conventional raster scan patterns where at most just over a quarter (a quarter plus one) of positions in a perimeter of a scan pattern are a set of successive positions (see FIG. 3).

Figure 12:
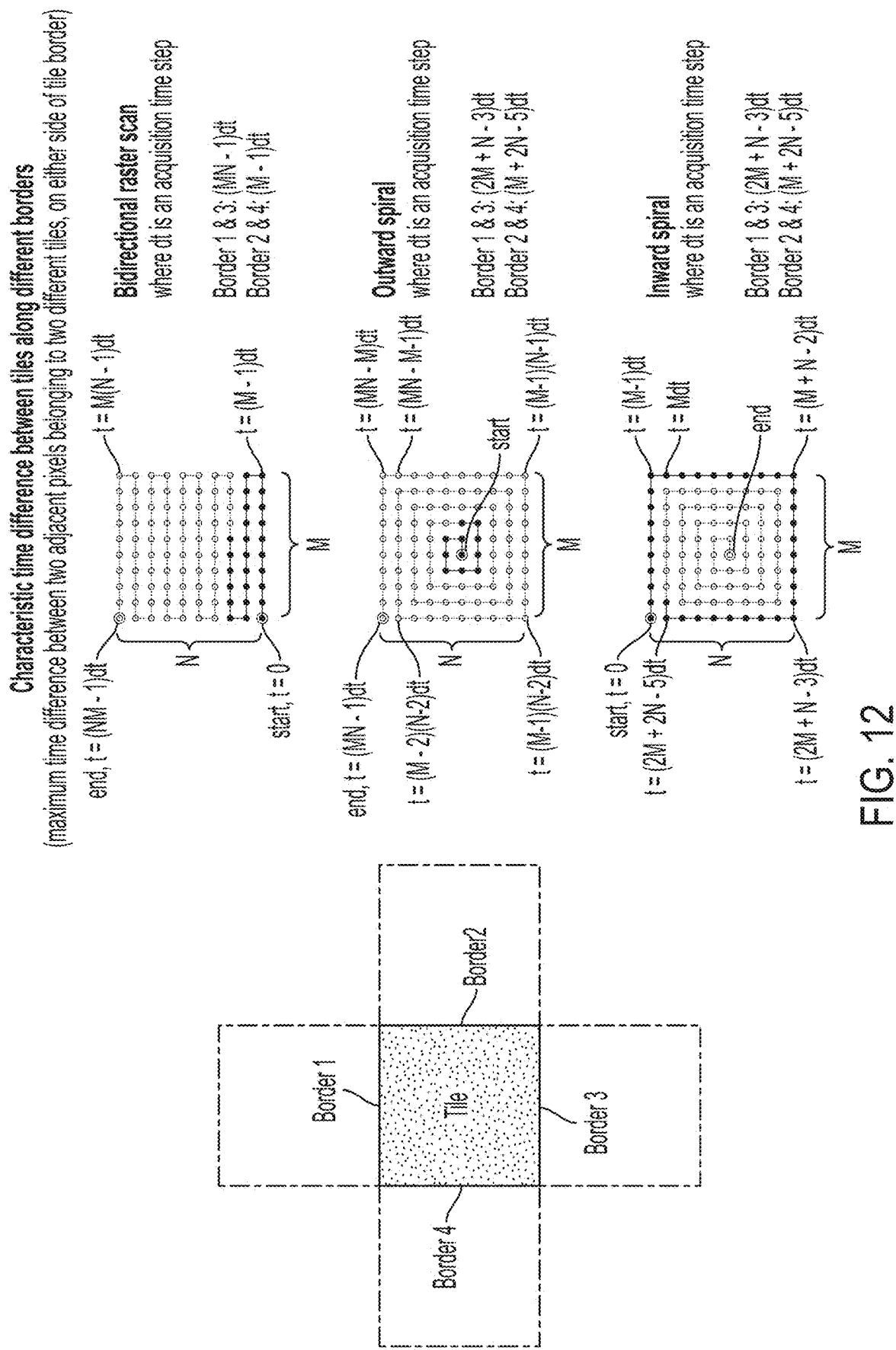
FIG. 12 is a comparison of a conventional raster scan pattern (top) to an outward spiral scan pattern (middle) and an inward spiral scan pattern (bottom), according to illustrative embodiments of the present disclosure.

FIG. 12 shows a more detailed analysis of acquisition time differences between adjacent tiles for inward and outward spiral patterns as compared to a conventional bidirectional raster scan. On the left, labels of tiles adjacent to a central tile are provided for comparison purposes. On the right, various points of each scan pattern are labelled in terms of when they are acquired relative to the starting time of the scan, where dt is an acquisition time step. (The starting point is labelled t=0, but a time of dt will elapse for data (e.g., light) acquisition prior to moving to the second position. The labels could thus be equivalently rewritten where t=dt at the starting position and the final position of each scan pattern is acquired at (MN)dt instead of (MN−1)dt, but the time differences would be unaffected. See FIGS. 13-16, where i=1 instead of i=0 at the starting position.) A characteristic time difference between tiles on different borders is given. Because greater acquisition time differences (all else being equal) generally cause more significant (e.g., noticeable and/or larger) artifacts, and for illustration purposes only, the characteristic time difference is taken as the maximum time difference of acquisition between adjacent pixels (scan positions) belonging to two different tiles (e.g., micro optical elements in an array, respectively) on either side of a tile border.

Figure 18:
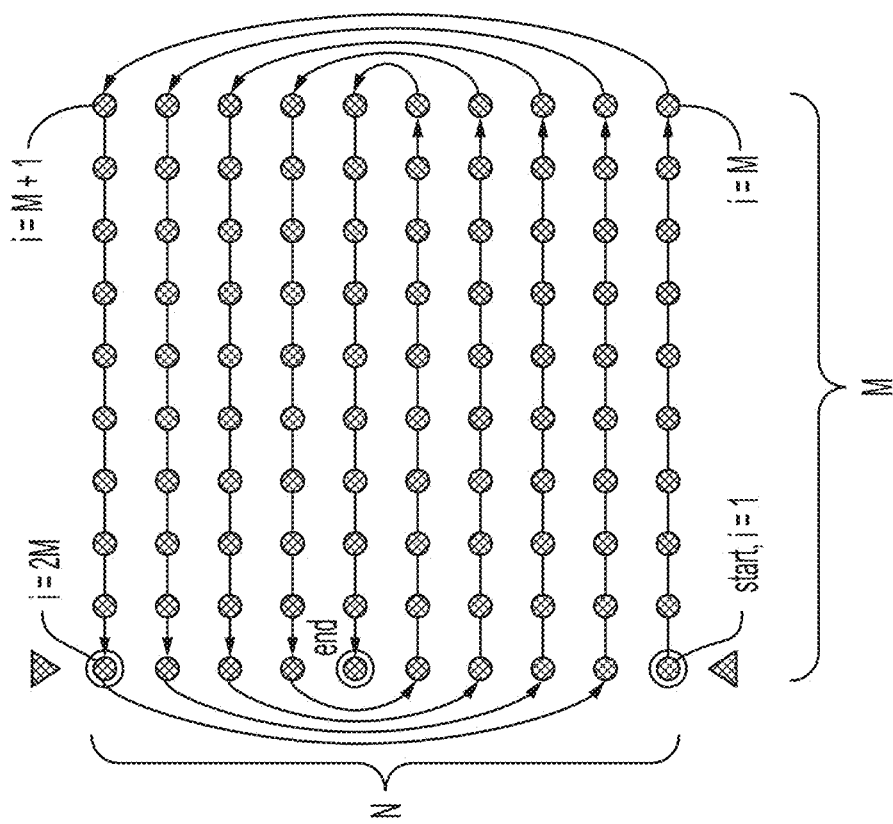
FIG. 18 illustrates relative acquisition times for various points in an inward bidirectional alternating rows scan pattern that starts with a bottom row, according to illustrative embodiments of the present disclosure.
Figure 17:
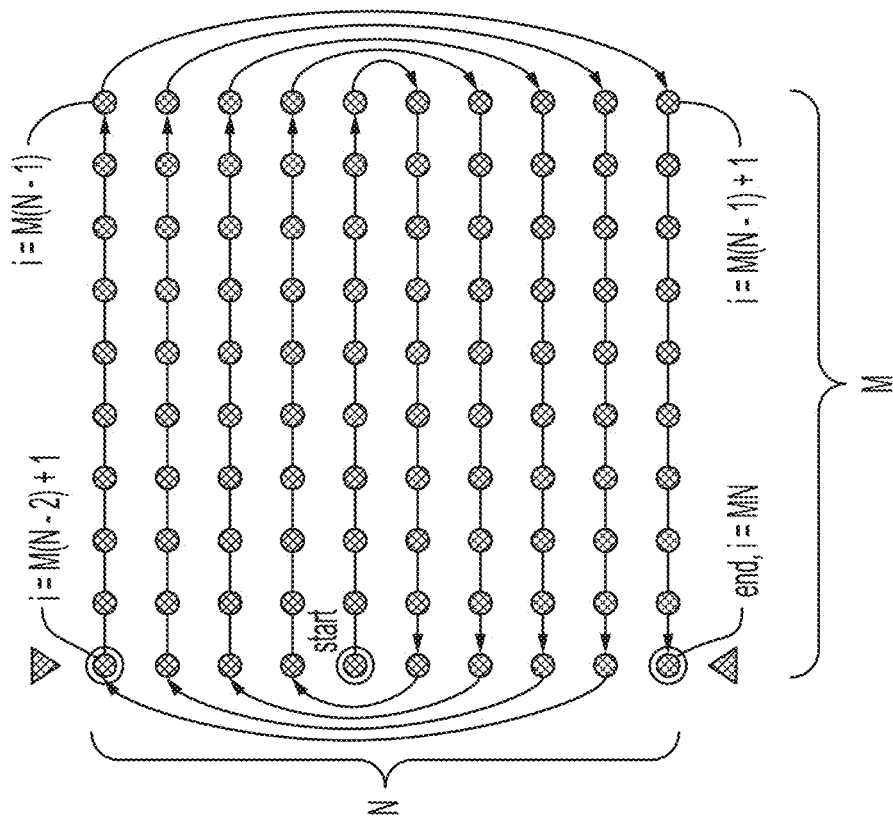
FIG. 17 illustrates relative acquisition times for various points in an outward bidirectional alternating rows scan pattern that starts with a middle row, according to illustrative embodiments of the present disclosure.

In the case of the conventional bidirectional raster scan pattern, the characteristic time difference for adjacent positions (or pixels) in the fast scan direction (borders 2 and 4 in this example) is (M−1)dt, but the characteristic time difference in the slow scan direction (borders 1 and 3) is (MN−1)dt. For both the inward and outward spiral scan patterns, the characteristic time difference at borders 1 and 3 is (2M+N−3)dt and at borders 2 and 4 is (M+2N−5)dt. Thus, the characteristic time difference of the spiral scan patterns is appreciably less than that of the conventional bidirectional raster scan pattern for certain borders (borders 1 and 3, where it is on the order of M instead of MN) and only slightly more for other borders (borders 2 and 4, where it is approximately 3M (assuming N=M) instead of M). It is, therefore, on average less about the whole perimeter. (Note that the "fast scan axis" and "slow scan axis" nomenclature does not apply to the spiral patterns.) For both the inward and outward bidirectional alternating row scan patterns, the characteristic time difference at borders 1 and 3 is (2M−1)dt and at borders 2 and 4 is (M−1)dt. Thus, the characteristic time difference of the bidirectional alternating row scan patterns is appreciably less than that of the conventional bidirectional raster scan pattern along the slow scan axis (for borders 1 and 3, where it is on the order of M instead of MN) and equivalent along the fast scan axis (for borders 2 and 4). For both the inward and outward unidirectional alternating row scan patterns, the characteristic time difference at borders 1 and 3 is Mdt and at borders 2 and 4 is (M−1)dt. Thus, the characteristic time difference of the unidirectional alternating row scan patterns is appreciably less than that of the conventional bidirectional raster scan pattern along the slow scan axis (for borders 1 and 3, where it is on the order of M instead of MN) and equivalent along the fast scan axis (for borders 2 and 4). See FIGS. 17-18 for reference figures with corner points labelled. Notably, in the alternating rows examples, no border has a longer characteristic time difference than the corresponding border in the conventional raster scan.

Referring still to FIG. 12, not only is the characteristic time difference less for the spiral scan patterns comparing to the corresponding slow scan axis borders (borders 1 and 3) of the conventional raster scan, but the characteristic time difference is less than the minimum time difference between adjacent positions (or pixels) along the slow scan axis borders. In the raster scan, the minimum time difference between adjacent pixels along slow scan axis borders is either (MN−M)dt or (MN−2M+1)dt depending on whether N is odd or even. So the minimum possible time difference for the conventional raster scan along slow scan axis borders is (MN−2M+1)dt, assuming M≥N and M is sufficiently large (e.g., >5), whereas the characteristic time difference (which was taken as the maximum) for the spiral scan patterns along equivalent borders is (2M+N−3)dt. It is clear that the latter is always less than the former for sufficiently large M and N (e.g., M≥N, M>5) and is over an order of magnitude less for relatively large M and N (e.g., M≥N, M>50). (For M<5, image resolution is often too low to be practically usable.) The corresponding characteristic time difference for the alternating rows examples (FIGS. 10-11 and 17-18) is 2M−1, which is even less than the characteristic time difference for the spiral scan pattern examples.

Table 2 gives a summary of maximum acquisition time differences for various examples of scan patterns at various example relative sizes and compared to a bidirectional raster scan. Table 2 further includes the maximum time difference (for slow scan axis or equivalent borders) as a percentage of the full scan time for the pattern (in addition to being expressed in a scan point position difference within the respective scan pattern). The conventional raster scan pattern has a maximum time difference on the order of MN while the maximum time difference of the spiral and alternating rows scan patterns is roughly on the order of M or N. Accordingly, the percentage of the full scan time for the maximum acquisition time difference for the spiral and alternating rows examples decreases with increasing relative scan pattern size (increasing number of positions) while the percentage of the full scan time for the maximum acquisition time difference for the convention raster scan actually increases (slightly) with increasing relative scan pattern size. For example, for a relatively large array of scan positions in a scan pattern (e.g., M=N=125 or 250), which may be used to acquire a full image of a sample, a maximum time difference for a conventional scan pattern is >99% of a full scan time, whereas it is <2% for a spiral scan pattern and <1% for an alternating rows scan pattern. Thus, image artifacts from sample motion should be greatly reduced or even eliminated (e.g., become unnoticeable) for such large arrays with spiral or alternating rows scan patterns. For smaller arrays in a scan pattern (e.g., M=N=25), which may be used to acquire a test scan pattern (e.g., as used in "Testing to Determine If Sample Has Self-stabilized" below), a maximum time difference is still at least 8 times smaller for spiral or alternating rows than a conventional raster scan. The spiral scan pattern has a maximum time difference of less than 30% of the full scan time and the alternating rows scan pattern has a maximum time difference of less than 20% of the full scan time.

patterns) may be more practical to implement (e.g., with respect to triggering the collection of the signal corresponding to a given scan point) than bidirectional scan patterns (e.g., bidirectional raster scan pattern or bidirectional alternating row scan patterns), as the step points are always acquired when traveling along the same direction. In the unidirectional raster scan, the maximum time difference between adjacent pixels within the same tile (i.e. pixels not located on either sides of a tile borders) is (M−1)dt, assuming that the line return takes a time of dt. In practice, the line return may take more than dt to accomplish, though still on the order of dt (e.g., <10dt). But even considering practical line return time of the unidirectional raster scan, there can be essentially no discontinuities (sample motion artifacts) between adjacent pixels within the same tiles, for both bidirectional and unidirectional raster scans used in a parallel imaging system, as shown in FIG. 4, even when a sample does move somewhat during imaging. For example, M=125 and dt=2 ms can be sufficiently small compared to the time it takes a resected breast lump sample to move over a distance of about 2 micrometers. In a spiral scan, the maximum time difference between adjacent pixels within the same tile (i.e. pixels not located on either sides of a tile borders) is (2M+2N−5)dt. In both unidirectional and bidirectional alternating row scans, the maximum time difference between adjacent pixels within the same tile (i.e. pixels not located on either sides of a tile borders) is (2M)dt, which is less than for the spiral scan and comparable with the bidirectional raster scan, and there can be almost no discontinuities (sample motion artifacts) between adjacent pixels within the same tiles, for both bidirectional and unidirectional alternating rows scans used in a parallel imaging system, even when a sample does move somewhat during imaging.

Lower time difference between acquisition of adjacent pixels in neighboring tiles achieved by, for example, spiral and alternating row scan patterns reflects in various properties of the scan pattern. In some embodiments, a time difference between acquisition of each pair of adjacent pixels in neighboring tiles is less than (MN−2M+1)dt, wherein dt is a time step for scanning. Alternatively put, in some embodiments, a position difference in an array of sequential positions defining a scan pattern is no more than (MN−2M+1). In some embodiments, the time difference is no more than (3M−3)dt (e.g., and M=N). In some embodiments, the time difference is no more than (2M−1)dt (e.g.,

TABLE 2

| Scan Pattern | | M = N = | 10 | 25 | 125 | 250 |
|---|---|---|---|---|---|---|
| | | Total # of scan points | 100 | 625 | 15,625 | 62,500 |
| Raster Bidirectional | Max. time difference | Scan points | 99 | 624 | 15,624 | 62,499 |
| | | % of full scan time | 99% | >99% | >99% | >99% |
| Raster Unidirectional | Max. time difference | Scan points | 90 | 600 | 15,500 | 62,250 |
| | | % of full scan time | 90% | 96% | >99% | >99% |
| Spirals | Max. time difference | Scan points | 27 | 72 | 372 | 772 |
| | | % of full scan time | 27% | <12% | <3% | <2% |
| Alternating Rows Bidirectional | Max. time difference | Scan points | 19 | 49 | 249 | 499 |
| | | % of full scan time | 19% | <8% | <2% | <1% |
| Alternating Rows Unidirectional | Max. time difference | Scan points | 10 | 25 | 125 | 250 |
| | | % of full scan time | 10% | 4% | <1% | <1% |

In the bidirectional raster scan, the maximum time difference between adjacent pixels within the same tile (e.g., pixels not located on either sides of a tile borders) is (2M−1)dt. Unidirectional scan patterns (e.g., unidirectional raster scan pattern or unidirectional alternating row scan and M=N). In some embodiments, an array of micro optical elements moves, during scanning and after a change of direction, to a number of positions in a series of sequential positions that is (i) always no less than or (ii) always no more than a number of positions that were moved to since an immediately prior direction change (e.g., moves in an outward or inward spiral, respectively). In some embodiments, an average sequence location of all of the perimeter positions in a scan pattern is less than MN/2. That is, in some embodiments, there are more positions in the perimeter of the scan pattern that occur before the middle position than after. In some embodiments, the average sequence location is less than 0.6*(MN/2). In some embodiments, the average sequence location is less than 0.1*(MN/2).

Detecting Sample Motion in Images

It can be advantageous for an imaging system to detect that the sample has moved during imaging based on an acquired image. During imaging or immediately after imaging, such a system could inform the user about the presence of sample motion. An imaging system could also inform the user about the size of area affected by sample motion artifacts (e.g., in absolute or relative to the sample surface area or relative to an entire image area). An imaging system could also output a visual representation of where it has detected sample motion artifacts. For example, an imaging system could display a thumbnail of the entire image where detected sample motion artifacts are indicated (e.g., color-coded on top of image thumbnail). With this information, a user wanting to have an image that would be free, or substantially free, of sample motion artifacts could then make another attempt at imaging the sample—with or without actively trying to further stabilize the sample and prevent it from undesired motion during imaging.

As described previously, a common sample motion artifact in a parallel imaging system is a discontinuity at tile borders in an image (where each tile corresponds to a respective objective in an array of objectives (e.g., an array of micro optical elements)). Discontinuities are often visible because of large intensity differences in adjacent perimeter pixels of different tiles as compared to intensity variations between adjacent interior pixels in tiles. Depending on sample characteristic(s) as well as features that are imaged (e.g., organelles of a tissue sample, which may be differentially stained), intensity variation between adjacent interior pixels of tiles in an image may be different in images of different samples or taken at different times or with different imaging settings. However, regardless of a particular range of adjacent interior pixel intensity variation in tile(s) of an image, intensity variation between adjacent perimeter pixels in adjacent tiles where an artifact is located will very likely be greater. Therefore, whether sample motion has occurred during imaging may be determined based, at least in part, on pair(s) of adjacent perimeter pixels (from adjacent tiles). In some embodiments, an intensity difference between at least one pair adjacent perimeter pixels, one being from a first tile and one being from a second adjacent tile, is compared to a threshold determined based on intensity variation in interior pixels of tile(s) to determine whether sample motion has occurred during imaging.

Figure 19:
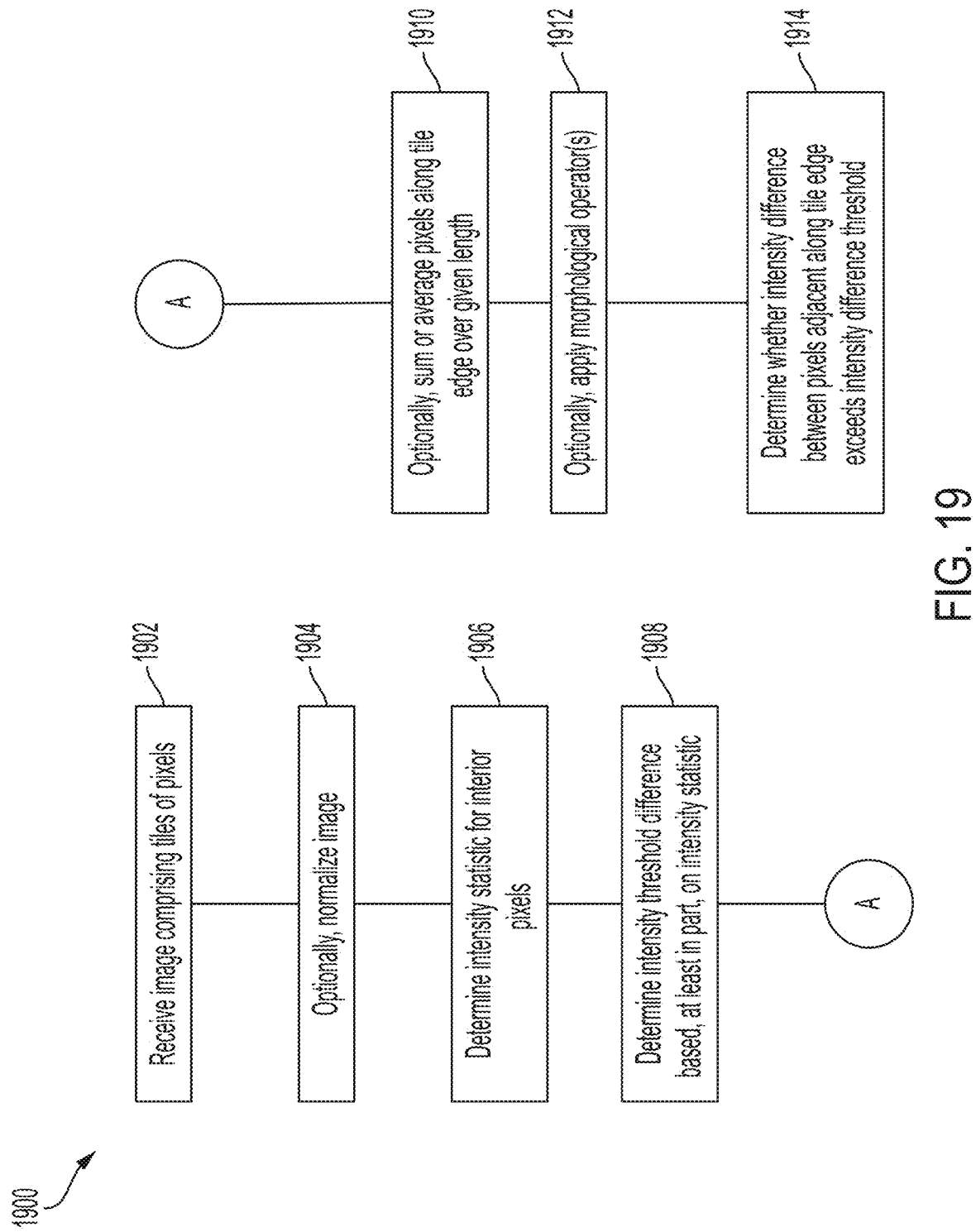
FIG. 19 is a process diagram of a method for determining whether sample motion occurred during acquisition of an image, according to illustrative embodiments of the present disclosure.
Figure 20:
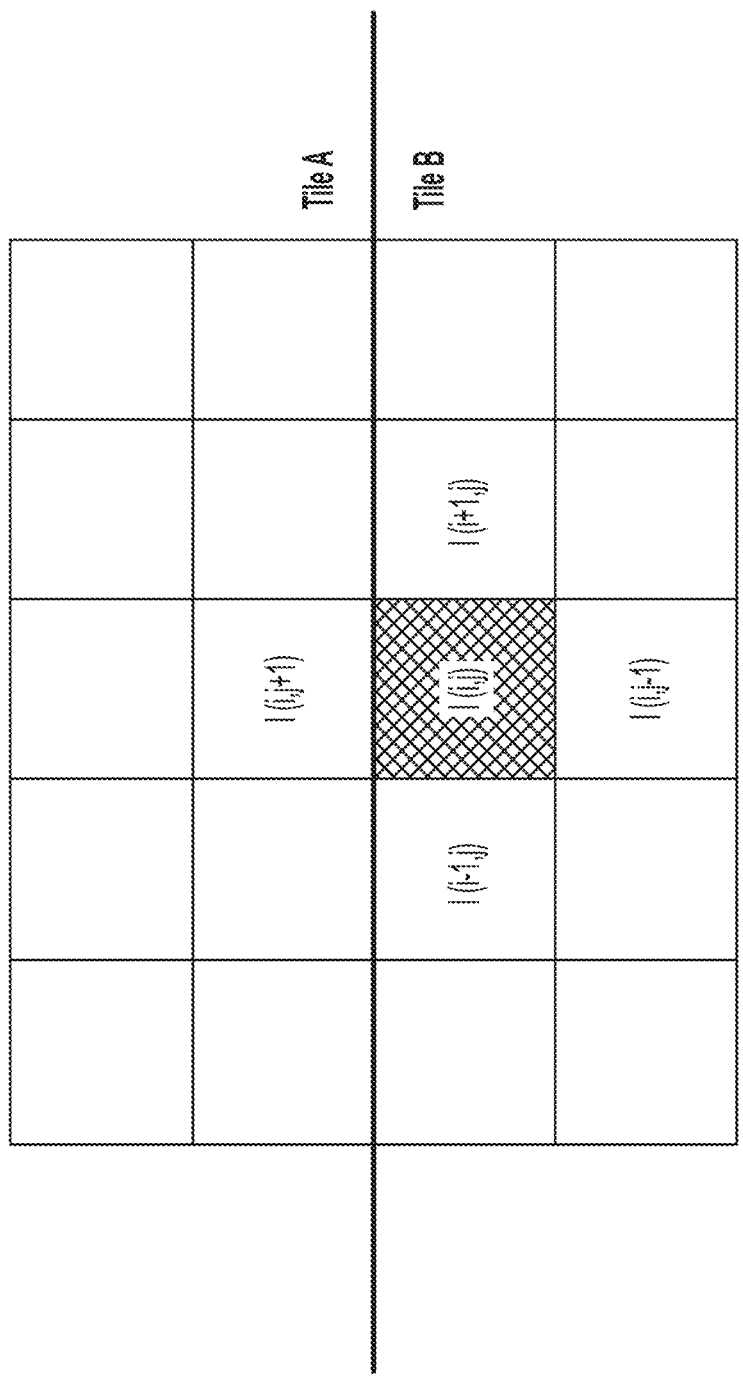
FIG. 20 illustrates adjacent pixels to a perimeter pixel (that is along a tile edge), including a pixel in a neighboring tile, according to illustrative embodiments of the present disclosure.

In some embodiments, and with reference to FIGS. 19 and 20, a method includes determining whether sample motion has occurred during imaging based on an image that includes tiles of pixels. The tiles may each correspond to a micro optical element in an array of micro optical elements. In step 1902 of method 1900, a processor of a computing device receives an image that includes tiles of pixels. Each of the tiles corresponds to a micro optical element in an array of micro optical elements. In some embodiments, a size of each tile corresponds to a unit cell of a micro optical element in the array that is scanned over during imaging. In optional step 1904, the image is normalized. For example, in some embodiments an illumination beam provided through an array of micro optical elements has a Gaussian distribution that may cause intensity to vary tile to tile such that image normalization can reduce effects of this variation.

In step 1906, the processor determines an intensity statistic (e.g., difference, average difference, mean, median, mode, standard deviation, variation) for interior pixels in one or more tiles. For example, an intensity statistic may be an average intensity for a plurality (e.g., all) of the pixels in a tile. As another example, an intensity statistic may be an average difference in intensity between an interior pixel and each of its adjacent pixels, for example averaged over all interior pixels in a tile. (Pixel (i,j−1) in FIG. 20 is an interior pixel; pixel (i,j) is adjacent to pixel (i,j−1). Each pixel shown in FIG. 20 corresponds to a position of a micro optical element during image acquisition where the micro optical element is moved along a scan pattern.) In step 1908, the processor determines an intensity difference threshold based, at least in part, on the intensity statistics. In this way, the intensity difference threshold is reflective typical variation in intensity between adjacent interior pixels in tiles of the image. It would be expected then that intensity differences between adjacent interior pixels falls below the threshold and intensity differences between adjacent perimeter pixels in adjacent tiles (for example, pixel (i,j+1) and pixel (i,j) in FIG. 20) where a sample motion artifact (e.g., discontinuity) occurs would exceed the threshold. If no artifact exists between adjacent tile edges of adjacent tiles, it would be expected that intensity differences between adjacent perimeter pixels across those edges (for example, pixel (i,j+1) and pixel (i,j) in FIG. 20) would not exceed the threshold.

In step 1914, the processor determines whether an intensity difference between adjacent perimeter pixels along a tile edge (for example, pixel (i,j+1) and pixel (i,j) in FIG. 20) exceeds the threshold in order to determine whether sample motion has occurred. In some embodiments, only one pair of adjacent perimeter pixels having an intensity difference greater than the threshold may be used to determine that sample motion has occurred. In some embodiments, a plurality of pairs of adjacent perimeter pixels are used.

In some embodiments method 1900 includes optional step 1910 wherein the processor sums or averages intensity differences of pairs of adjacent perimeter pixels, or intensities of perimeter pixels for a pair of tile edges, and then differences the sums or averages before comparing to an intensity difference threshold. (In FIG. 20, pixels (i−1,j), (i,j), and (i+1,j) are perimeter pixels along an edge of Tile B and pixel (i,j+1) is a perimeter pixel along an edge of Tile A that is adjacent to the edge of Tile B.)

In some embodiments method 1900 includes optional step 1912 wherein one or more morphological operators are applied to an image prior to comparing an intensity difference of adjacent pixels along adjacent tile edges of adjacent tiles to an intensity difference threshold. For example, (e.g., one dimensional) operators such as an erode and/or dilate operator may be applied. In some embodiments, applying an erode operator followed by a dilate operator exaggerates intensity differences between adjacent pixels in adjacent tiles of an image such that their intensity difference is greater relative to intensity differences between adjacent interior pixels in tiles of the image. One dimensional morphological operator(s) may be applied along a slow scan direction (e.g., along a direction with stronger sample motion artifacts). An intensity difference threshold may be determined after applying morphological operator(s).

Method 1900 may include one or both of optional step 1910 and optional step 1912, applied in either order.

In some embodiments, whether sample motion has occurred during imaging (e.g., and an amount of sample motion) is determined based, at least in part, on at least one pair of adjacent perimeter pixels in an image. Each of the at least one pair may include a first perimeter pixel in a first tile and an adjacent second perimeter pixel in a second tile adjacent to the first tile (e.g., intensities of the pixels in the at least one pair). In some embodiments, whether sample motion has occurred during imaging is determined based, at least in part, on an average or sum of intensities of a plurality of first pixels in an edge of a first tile and an average or sum of intensities of a plurality of second pixels in an edge of a second tile adjacent to the edge of the first tile, respectively. For example, with reference to FIG. 20, a difference between an average of intensities of pixels (i−1,j), (i,j), and (i+1,j) and an average of intensities of pixels (i−1,j+1), (i,j+1), and (i+1,j+1) may be compared to an intensity difference threshold to determine whether sample motion has occurred. As another example, again with reference to FIG. 20, a difference between a sum of intensities of pixels (i−1,j), (i,j), and (i+1,j) and a sum of intensities of pixel may be compared to an intensity difference threshold to determine whether sample motion has occurred. Perimeter pixels from multiple pairs of adjacent tiles (e.g., every tile) in an image may be used to determine whether sample motion has occurred. For example, FIG. 20 only shows Tile A and Tile B, but intensity differences of pixels from a tile horizontally adjacent to Tile A and a tile horizontally adjacent to Tile B may be used in combination with pixels from Tile A and Tile B In some embodiments, a user is automatically notified (e.g., in one or more graphical user interfaces) that sample motion has occurred during imaging (e.g., and the amount of sample motion) upon determining that the sample motion has occurred. In some embodiments, a second image of a sample is automatically acquired upon determining that sample motion has occurred. For example, a first image of a sample can be obtained, method 1900 can be performed, and if it is determined that sample motion has occurred during imaging of the first image, a second image may then be automatically acquired. In some embodiments, an intensity difference threshold is applied to an image and the resulting thresholded image is then displayed to a user. In such a manner, a user can make a quick qualitative assessment of whether sample motion has occurred and/or of how much sample motion has occurred.

An amount of sample motion may be estimated from an absolute intensity difference between pair(s) of adjacent perimeter pixels in adjacent tile edges. For example, intensity differences may be used to determine a displacement vector that corresponds to an amount of sample motion. In some embodiments, an amount of sample motion is displayed to a user (e.g., in a graphical user interface).

FIGS. 21A-E illustrate another method to determine whether sample motion has occurred during imaging based on pairs of adjacent pixels at tile edges of adjacent tiles in an image. FIG. 21A shows a normalized image with sample motion artifacts. FIG. 21B shows a difference image where the difference image has been generated based on a single pixel horizontal shift in the image from FIG. 21A. FIG. 21C shows a one dimensional plot of intensities across the difference image shown in FIG. 21B. The dashed line in FIG. 21C shows an intensity threshold based on intensities of interior pixels (the cluster) that can be used to determine whether sample motion has occurred during imaging. For example, spikes (pixel intensities) in the plot of FIG. 21C occur due to large intensity differences between adjacent pixels at adjacent vertical tile edges of adjacent tiles and exceed the intensity threshold. FIG. 21D shows the difference image after a one dimensional (along the vertical direction) erode operator, then one dimensional dilate operator have been applied to the difference image. FIG. 21E shows a one dimensional plot of intensities across the modified difference image in FIG. 21D. The dashed line in FIG. 21E shows a different intensity threshold determined after the morphological operators have been applied. As can be seen qualitatively in FIG. 21D and quantitatively in FIG. 21E, sample motion artifacts (corresponding to spikes in FIG. 21E) are more apparent after application of morphological operators. An image without sample motion artifacts would not have appreciable spikes in a one dimensional intensity plot (e.g., similar to FIGS. 21C and 21E). In some embodiments, an intensity threshold is based on an average intensity of pixels (e.g., all pixels) (e.g., interior pixels) in the difference image.

Figure 41:
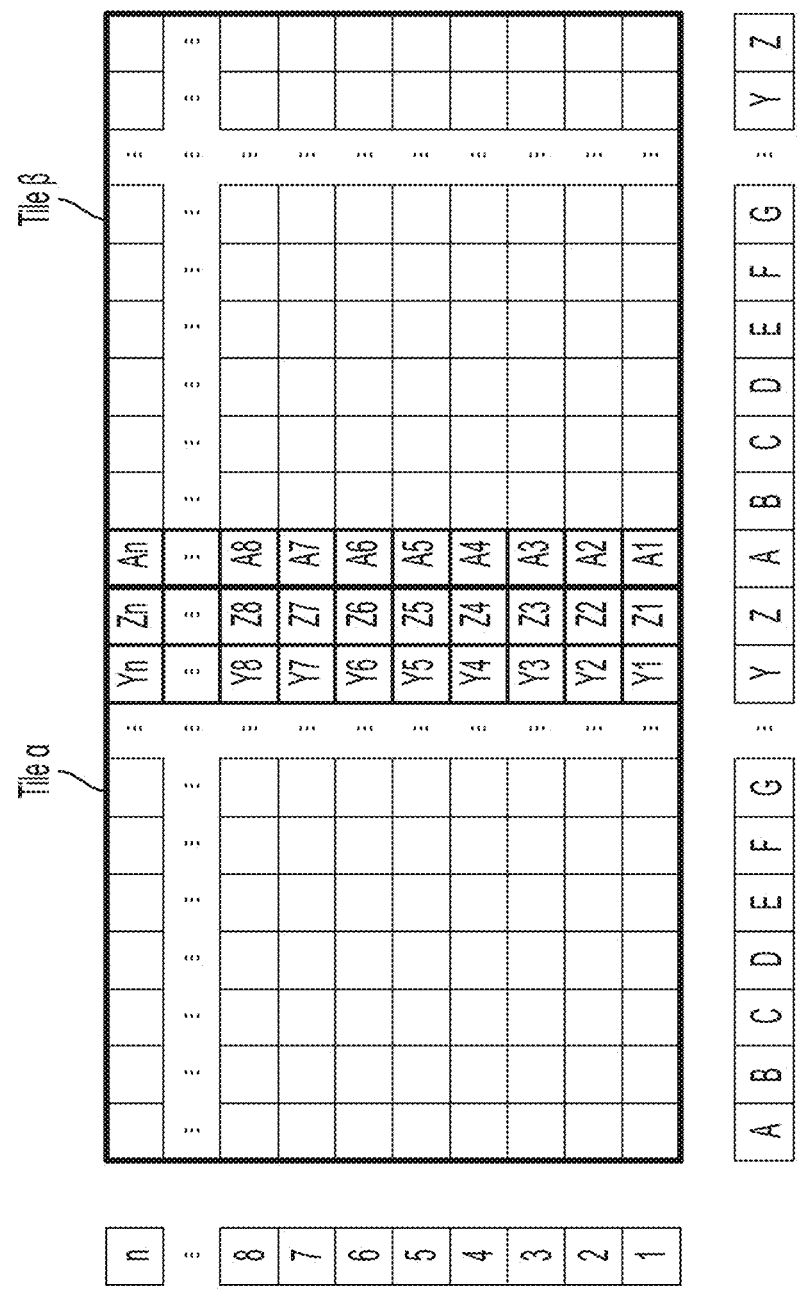
FIG. 41 illustrates methods of determining whether sample motion has occurred during imaging based on comparing the intensity difference between pairs of adjacent pixels located on either side of a tile boundary, according to illustrative embodiments of the present disclosure.

FIG. 41 illustrates methods to determine whether sample motion has occurred during imaging based on comparing the intensity of pairs of adjacent pixels at tile edges of adjacent tiles in an image, with the intensity of pairs of adjacent pixels within the same tile. In some embodiments, the intensity comparison may involve calculating the intensity difference between adjacent pixels across the tile edge and comparing it to the intensity difference between adjacent pixels within the tile. For example, pairs of adjacent pixels at tile edges may belong to the line of pixels Z of tile α and to the line of pixels A of tile β, and pairs of adjacent pixels within the same tile may belong to line of pixel Y and Z of tile α. Such a method may use one or more pairs of pixels at the tile edge of adjacent tiles in an image and one or more pairs of pixels within the same tile. For example, all pairs of pixels Z-A at the tile edge of adjacent tiles in an image may be used, and all pairs of pixels Y-Z within tile α may be used. Let $I_\alpha(Y_1)$ be the intensity value of pixel $Y_1$ for tile α and $I_\alpha(Z_1)$ be the intensity value of pixel $Z_1$ for tile α, and so on. The mean absolute intensity difference $\Delta\text{ext}_{\alpha\beta}$ along the boundary between tile α and tile β may calculated as follows:

$$\Delta\text{ext}_{\alpha\beta}=(1/n)*[|I_\alpha(Z_1)-I_\beta(A_1)|+|I_\alpha(Z_2)-I_\beta(A_2)|+\ldots+|I_\alpha(Z_n)-I_\beta(A_n)|]$$

Similarly, the mean absolute intensity difference $\Delta\text{int}_\alpha$ along a horizontal segment located 1 pixel away from the boundary between tile α and tile β may be calculated as follows:

$$\Delta\text{int}_\alpha=(1/n)*[|I_\alpha(Z_1)-I_\alpha(Y_1)|+|I_\alpha(Y_2)-I_\alpha(Y_2)|+\ldots+|I_\alpha(Z_n)-I_\beta(A_n)|]$$

And a motion index $M_{\alpha\beta}$ for the boundary between tile α and tile β may be calculated as the ratio between $\Delta\text{ext}_{\alpha\beta}$ and $\Delta\text{int}_\alpha$:

$$M_{\alpha\beta}=\Delta\text{ext}_{\alpha\beta}/\Delta\text{int}_\alpha$$

Figure 42A:
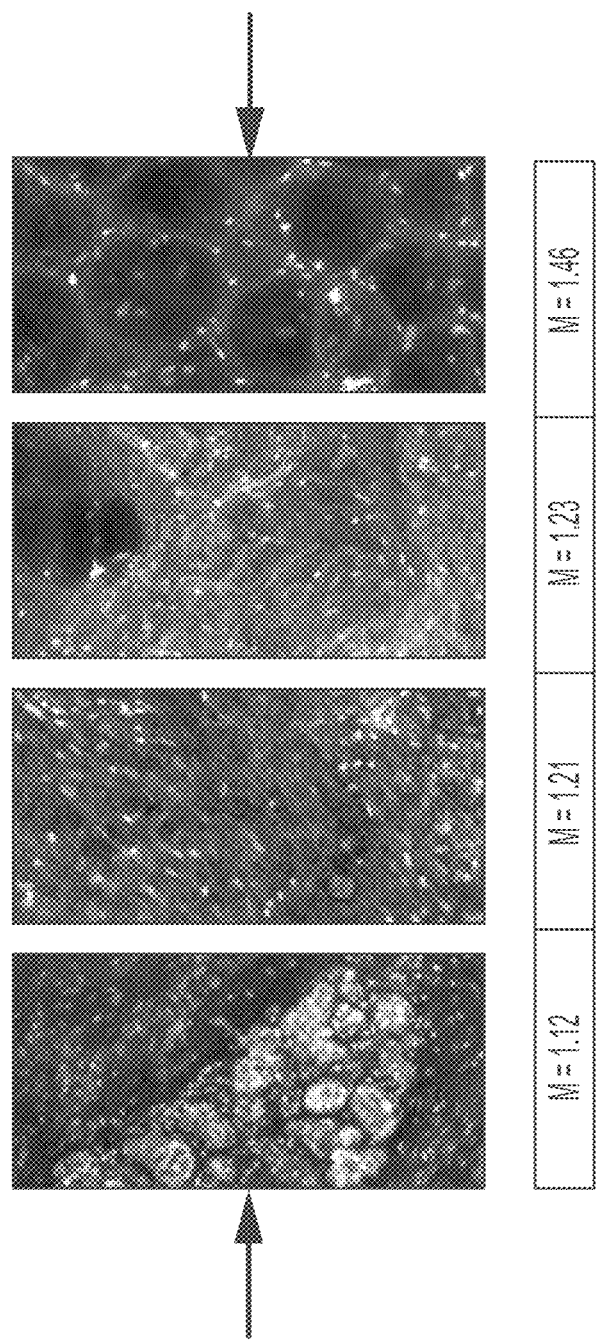
FIGS. 42A-D presents example images acquired by an imaging system with different levels of sample motion occurred during acquisition, according to illustrative embodiments of the present disclosure.
Figure 42B:
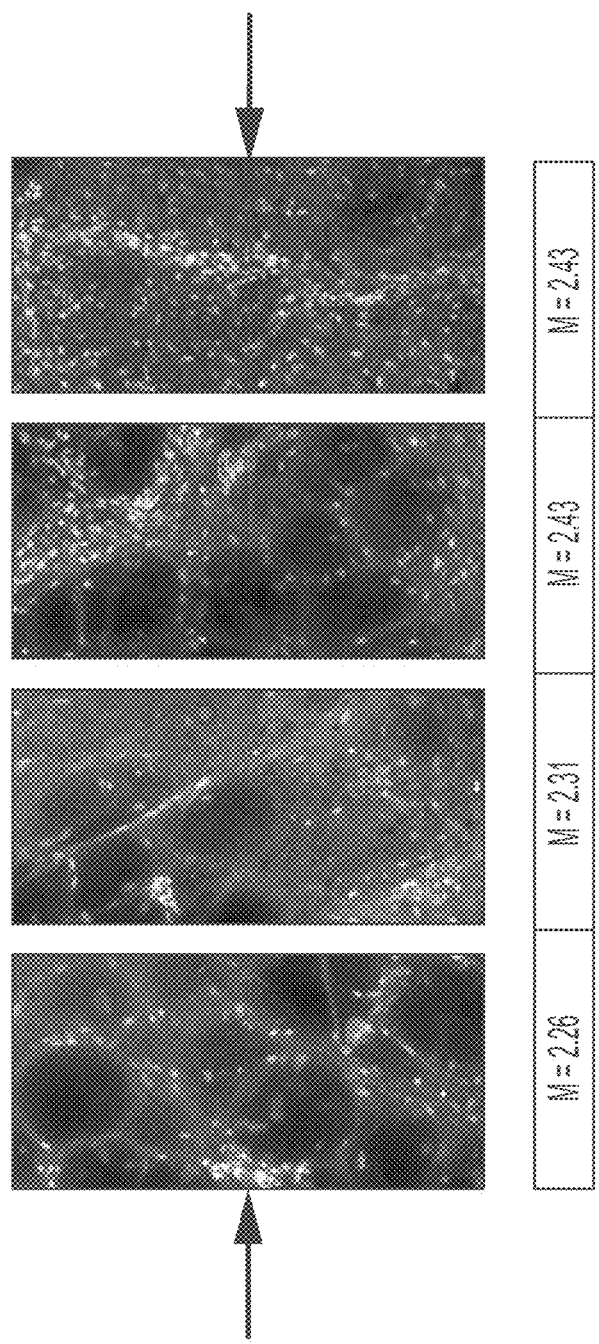
Figure 42C:
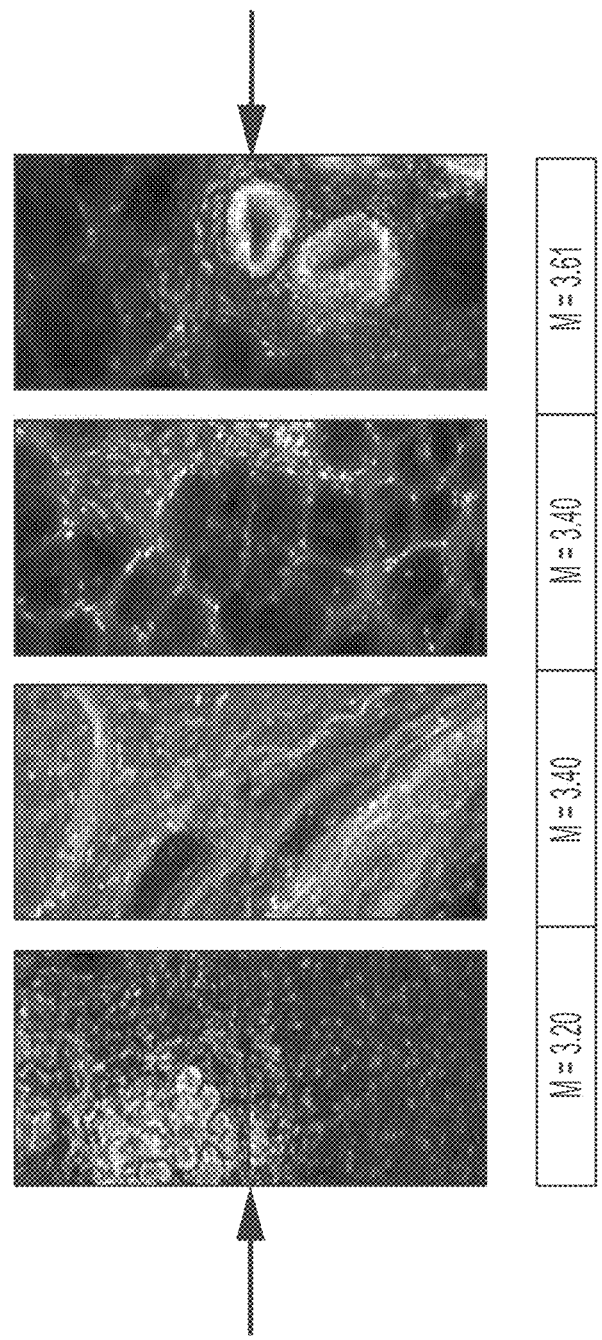
Figure 42D:
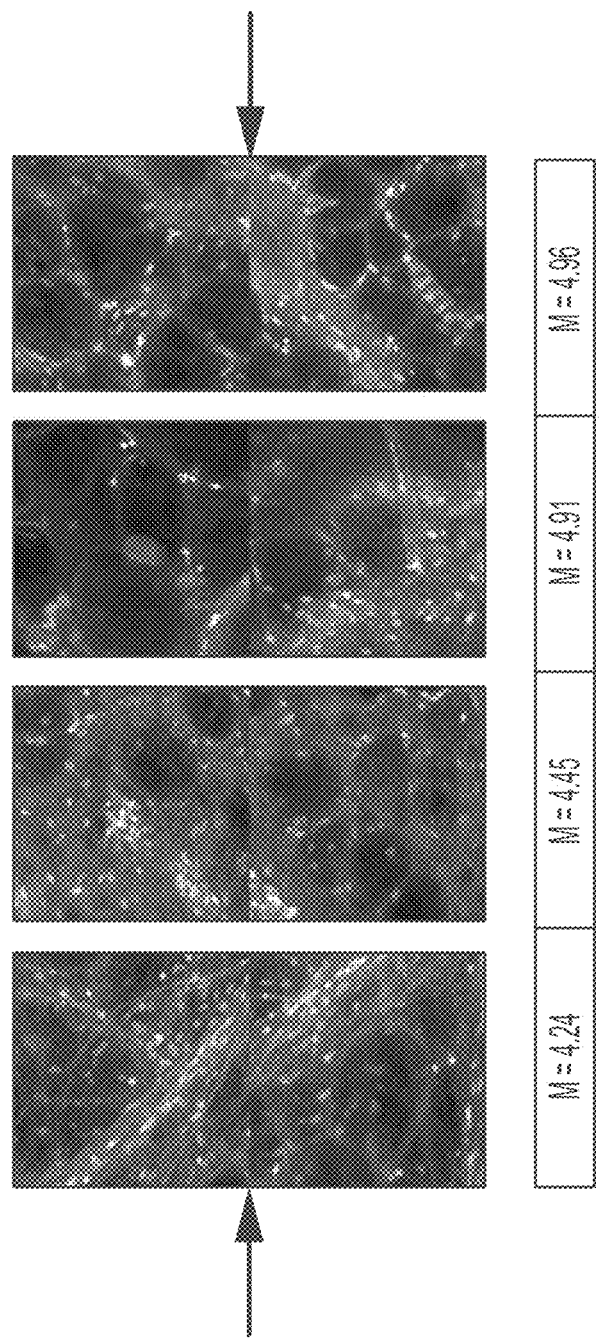

In the above example, a motion index $M_{\alpha\beta}$ close to 1 indicates that the intensity difference of pairs of adjacent pixels across the tile boundary is not significantly different from the intensity difference of pairs of adjacent pixels within the tile. For some imaging parameters, a motion index $M_{\alpha\beta}$ below 1.5 (as in FIG. 42A) is observed when no significant motion of the sample has occurred during the imaging, and the resulting image may be seamless or present only motion artifacts that would be imperceptible or nearly imperceptible by a user during image interpretation. A motion index $M_{\alpha\beta}$ between 1.5 and 2.75 (as in FIG. 42B) is observed when a relatively small motion of the sample has occurred during the imaging and results in images presenting minor motion artifacts, e.g., discontinuities across the tile boundary, that would not materially affect ease of image interpretation by a user. A motion index $M_{\alpha\beta}$ between 2.75 and 4 (as in FIG. 42C) is observed when a relatively large motion of the sample has occurred during the imaging and results in images presenting major motion artifacts that may annoy a user but would not materially affect image interpretation. A motion index $M_{\alpha\beta}$ above 4 (as in FIG. 42D) is observed when a relatively very large motion of the sample has occurred during the imaging and results in images presenting critical motion artifacts that may adversely impact image interpretation (e.g., part of the sample may be too strongly distorted in the image, or missing from the image). In some embodiments, sample motion is determined to have occurred (e.g., automatically) if $M_{\alpha\beta}$>2.75 (e.g., $M_{\alpha\beta}$>2). The arrows in FIGS. 42A-D indicate the horizontal position in the figure of the tile boundary.

In some embodiments, a motion index may be calculated for pairs of adjacent pixels belonging to the same tile. For example, referring to FIG. 41, one may calculate a similar motion index for pairs of adjacent pixels wherein the first pixel of a pair belongs to pixel row Y and the second pixel of a pair belongs to pixel row Z. For some scan patterns (e.g., raster scan patterns, spiral scan patterns, alternating rows scan patterns), the time difference between two adjacent pixels in pixel row Y may be significantly smaller than the time difference between one pixel in pixel row Y and an adjacent pixel in pixel row Z, and the latter may be large enough to present some motion artifacts. Let $I(Y_1)$ be the intensity value of pixel $Y_1$ and $I(Z_1)$ be the intensity value of pixel $Z_1$ in the same tile, and so on. A motion index $M_{YZ}$ may, for example, be calculated as follows:

$$M_{YZ} = \Delta ext_{YZ}/\Delta int_Y$$

where $$\Delta ext_{YZ} = (1/(n-1))*[|I(Z_1)-I(Y_1)|+|I(Z_2)-I(Y_2)|+ \ldots + |I(Z_n)-I(Y_n)|]$$

and $$\Delta int_Y = (1/(n-1))*[|I(Y_2)-I(Y_1)|+|I(Y_3)-I(Y_2)|+ \ldots + |I(Y_n)-I(Y_{n-1})|]$$

In some embodiments, sample motion is determined to have occurred (e.g., automatically) if $M_{YZ}$>2.75 (e.g., $M_{YZ}$>2). In some embodiments, a method to detect sample motion in the images may be used after the image acquisition has been completed. In some embodiments, a method to detect sample motion in the images may also be used during the image acquisition. Optionally, a system may notify a user whenever sample motion above a predetermined level is detected during the image acquisition (e.g., as determined using a motion index). Optionally, a system may also automatically terminate an image acquisition whenever sample motion above a predetermined level is detected during the image acquisition (e.g., as determined using a motion index). Optionally, a system may also automatically terminate the current image acquisition and automatically relaunch an image acquisition whenever sample motion above a predetermined level is detected during the image acquisition (e.g., as determined using a motion index). A user may manually determine to reacquire an image or continue interpreting an image based on a user receiving an automatic output of a motion index (e.g., presented by graphical representation or in text form).

Testing to Determine if Sample has Self-Stabilized

To reduce the effect of sample motion in high resolution images, it can be enough to leave a sample untouched on a transparent imaging window for some time, allowing it to stabilize itself on the imaging window. Starting the imaging process only after the sample has reached a sufficient stabilization level (e.g., when its motion rate during the time it takes to acquire an image becomes less than the resolution of the image) can significantly reduce or even completely eliminate sample motion artifacts. However, because sample motion that affects image quality is on a micro-scale (e.g., ~10-100 µm over tens of seconds), it is not always perceptible to an unaided user. Moreover, a sample self-stabilization time period differs from one sample to another and it is usually longer for larger samples than for smaller ones. Furthermore, some sample motion may be acceptable for certain applications, while that same amount of motion may be unacceptable for other applications. Therefore, convenient testing to determine, qualitatively, semi-quantitatively, or quantitatively, that sample motion has not exceeded some predetermined (e.g., preselected) threshold is desirable. The predetermined threshold may be determined empirically or computationally for, for example, a given sample type (e.g., material and/or size). In some embodiments, to detect when a sample has sufficiently stabilized for a desired application, an imaging system can launch a stabilization test scan process, comparing scanned sample positioning across predefined (e.g., preselected) intervals of time.

Any test scan of a sample should take less time to run (e.g., be smaller in size) than the full scan that will be run to image the sample once it has self-stabilized. In some embodiments, the time intervals and other parameters of a self-stabilization test scan can be selected to detect motion rate corresponding to about one image pixel over the imaging time. In some embodiments, a higher resolution test scan can be used in order to ensure that when no sample motion is noticeable in the test scan, no sample motion will be noticeable in the complete scan. By using an appreciably smaller test scan size (e.g., no more than 50%, or no more than 25%, of an area of a complete scan) (e.g., no more than 50%, or no more than 25%, of an area of a unit cell of a micro optical element in an array of micro optical elements being scanned during imaging), the higher resolution test scan can still take less time to run than a complete scan, even for a constant time step. Alternatively or additionally, a faster time step can be used. In some embodiments, when a stabilization test scan process detects no difference in a position of a sample between successive intervals (e.g., by comparing successive test scans), an imaging process can be launched that will produce a full image free of sample motion artifacts.

In some application contexts under high time pressure (e.g., when imaging is performed intraoperatively), it may be that a sample takes relatively too long to stabilize to the point where the motion rate corresponds to about one image pixel over the imaging time. In such application contexts, it might be preferable to launch an image acquisition, even if the sample still is not fully stabilized and if the resulting image would contain some level and distribution of motion artifacts. Motion artifacts of small to moderate magnitude and/or motion artifacts localized in some areas of the sample may be tolerable, so long as they do not compromise the interpretation of the image and, thus, the clinical outcome. However, widespread motion artifacts and/or motion artifacts of critical magnitude that may adversely impact the interpretation of the image and the clinical outcome must be avoided. Therefore, in such application contexts, it is desirable to monitor the stabilization state of the sample, in order to determine a good moment at which to launch an image acquisition, e.g. a moment at which the sample motion has reduced to a level that should not adversely impact the interpretation of the image and, thus, the clinical outcome. In some embodiments, when a stabilization test scan process detects no difference in a position of a sample between successive intervals (e.g., by comparing successive test scans), an imaging process can be launched that will produce a full image in which motion artifacts, if any, should not adversely impact the interpretation of the image and, thus, the clinical outcome.

A stabilization test scan can be made at the same resolution as the image to be acquired after and with a time interval corresponding to the imaging time. However, such a stabilization test would not allow a user to save time, in comparison to simply acquiring the image and detecting the presence of sample motion, e.g. using the methods described above. To save time, a stabilization test scan can be made at the same resolution than the image to be acquired after, but over a smaller scan area to be completed in a shorter time. Alternatively, the stabilization test scan can be made with a higher resolution than the image to be acquired after, but over a smaller scan area to be completed in a shorter time. For a parallel imaging system, a scan area could be significantly smaller than an area between adjacent micro optical elements (e.g., a unit cell of a micro optical element), allowing to significantly save on the scan time. Then, comparing stabilization test scans acquired at different moments in time (e.g., successive stabilization test scans), it can be determined whether a sample is still in motion (e.g., still relaxing).

Figure 22A:
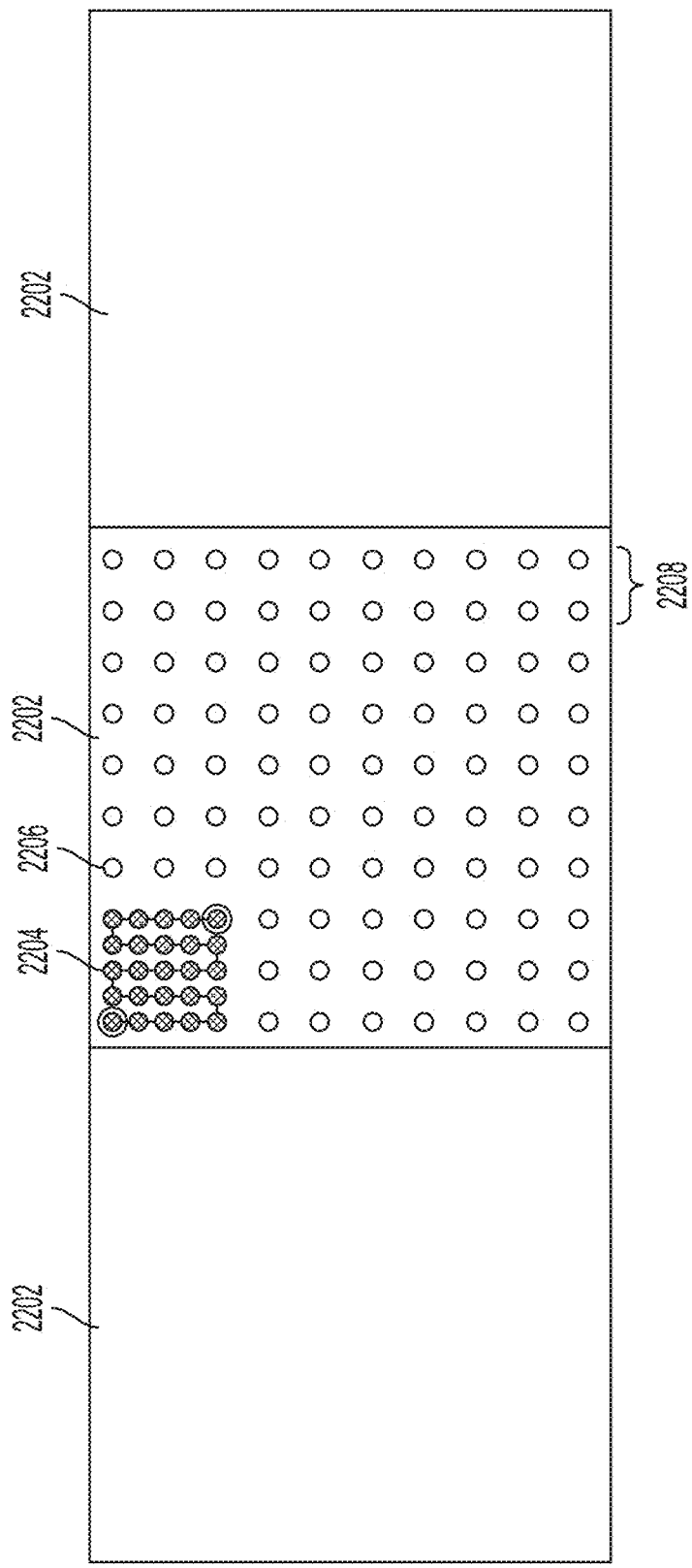
FIGS. 22A-B illustrate a comparison between a test scan patterns and positions in a scan pattern used to acquire a full image, according to illustrative embodiments of the present disclosure.
Figure 22B:
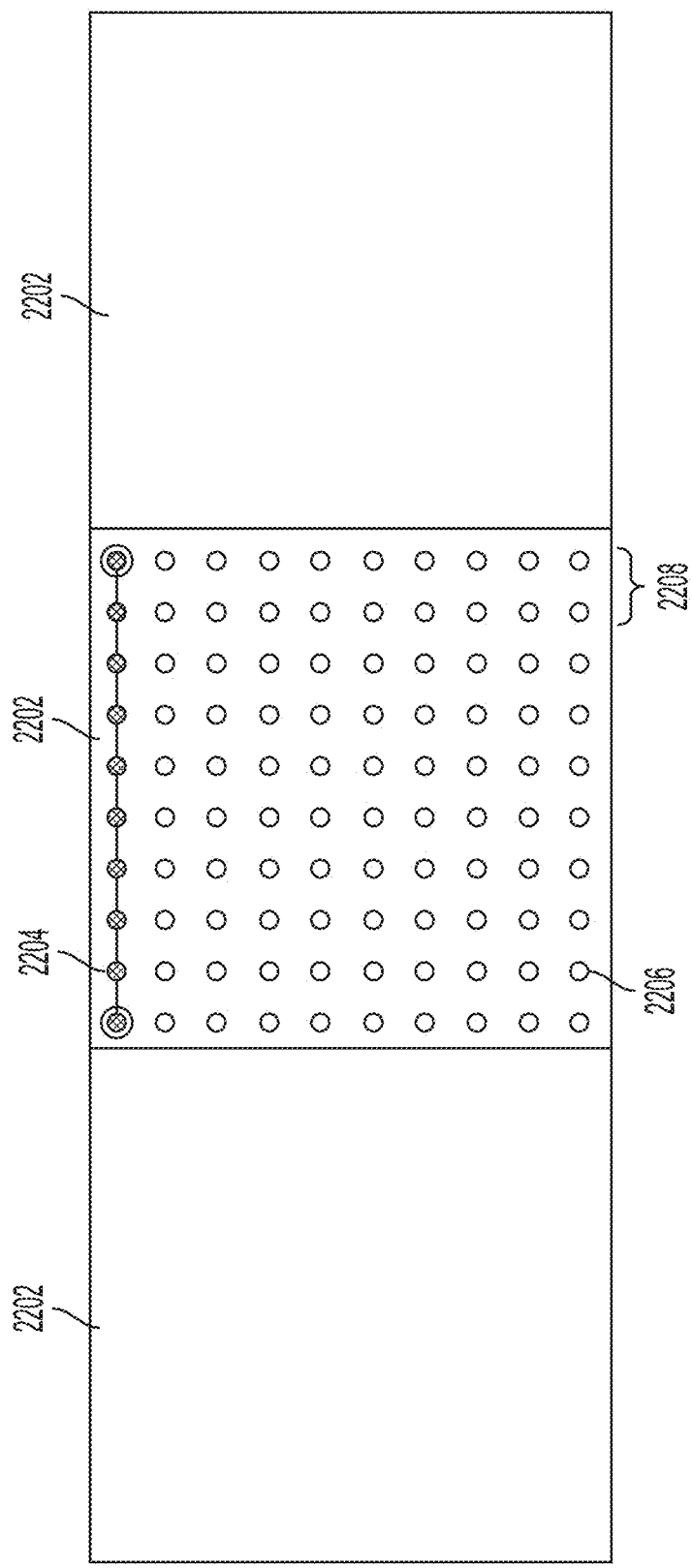

FIGS. 22A-B show a comparison between example test scan patterns 2204 and a scan pattern used to acquire a full image (a "full scan pattern") that includes a series of sequential positions 2206. Each box 2202 indicates an area that would be scanned by a respective micro optical element in an array of micro optical elements. Thus, the three boxes 2202 that are shown would correspond to a respective unit cell of each of three micro optical elements in an array of micro optical elements. Test scan pattern 2204 has a higher resolution than the full scan pattern as indicated by the relative density of positions in the respective scan patterns (where span 2208 indicates a resolution of the full scan pattern). In FIG. 22A, test scan pattern 2204 has an area of no more than about 10% of the area of the corresponding unit cell, but other sizes of test scan pattern 2204 may be used. In FIG. 22B test scan pattern 2204 has the same resolution as the full scan pattern as indicated by the relative density of positions in the respective scan patterns (where span 2208 indicates a resolution of the full scan pattern). It is desirable, but not strictly necessary, that the combination of resolution and step time used to scan over test scan pattern 2204 results in faster acquisition time than the combination of resolution and step time used in the full scan pattern. It is generally undesirable to use a lower resolution for a test scan pattern because sample motion that may be apparent in a higher resolution full scan pattern may be obfuscated by the lower resolution test scan pattern. In some embodiments, a test scan pattern and a full scan pattern use the same step time. In order to determine whether sample motion is occurring or has occurred, an array of micro optical elements can be scanned over test scan pattern 2204 multiple times to acquire multiple images, each at a different time, and the images can be subsequently compared. Test scan pattern 2204 is shown as a bidirectional raster scan, but other scan patterns can be used (e.g., as described above, see "Scan Patterns").

The test scan pattern 2204 shown in FIG. 22A extends along two dimensions. Other test scan patterns can be obtained by scanning along a single dimension, for example as test scan pattern 2204 in FIG. 22B. In imaging systems comprising a fast scan axis and a slow scan axis, it is advantageous, time-wise, to produce one-dimensional test scan patterns by scanning only along the fast scan axis. For example, a test scan pattern may be obtained by scanning a single line along the fast scan axis, while the slow scan axis remains in the same position. In some embodiments, the one-dimensional test scan pattern and the two-dimensional full scan pattern use the same resolution and step time. In some such embodiments, if the full scan pattern consists of M×N scan steps of equal distances along the fast and the slow scan axes, the one-dimensional test scan pattern will be N times faster. This gain in time is more substantial for large N (e.g., N=125 or N=250). In some embodiments, the one one-dimensional test scan pattern extends over the same length as the full scan pattern fast axis. In some embodiments, the one-dimensional scan pattern extends only over a fraction of the range of the full scan pattern. Thus, the gain in time may be even larger.

One-dimensional test scan may be acquired successively, even at high frequency since their scan time is small, and compared one to another to detect sample motion. A one-dimensional test scan may be compared to the immediate next or previous one-dimensional test scan or to another one-dimensional test scan separated in time by one or more other one-dimensional test scans. The longer the time difference between the compared one-dimensional test scans, the more sensitive they will be to detect sample motion.

Figure 45:
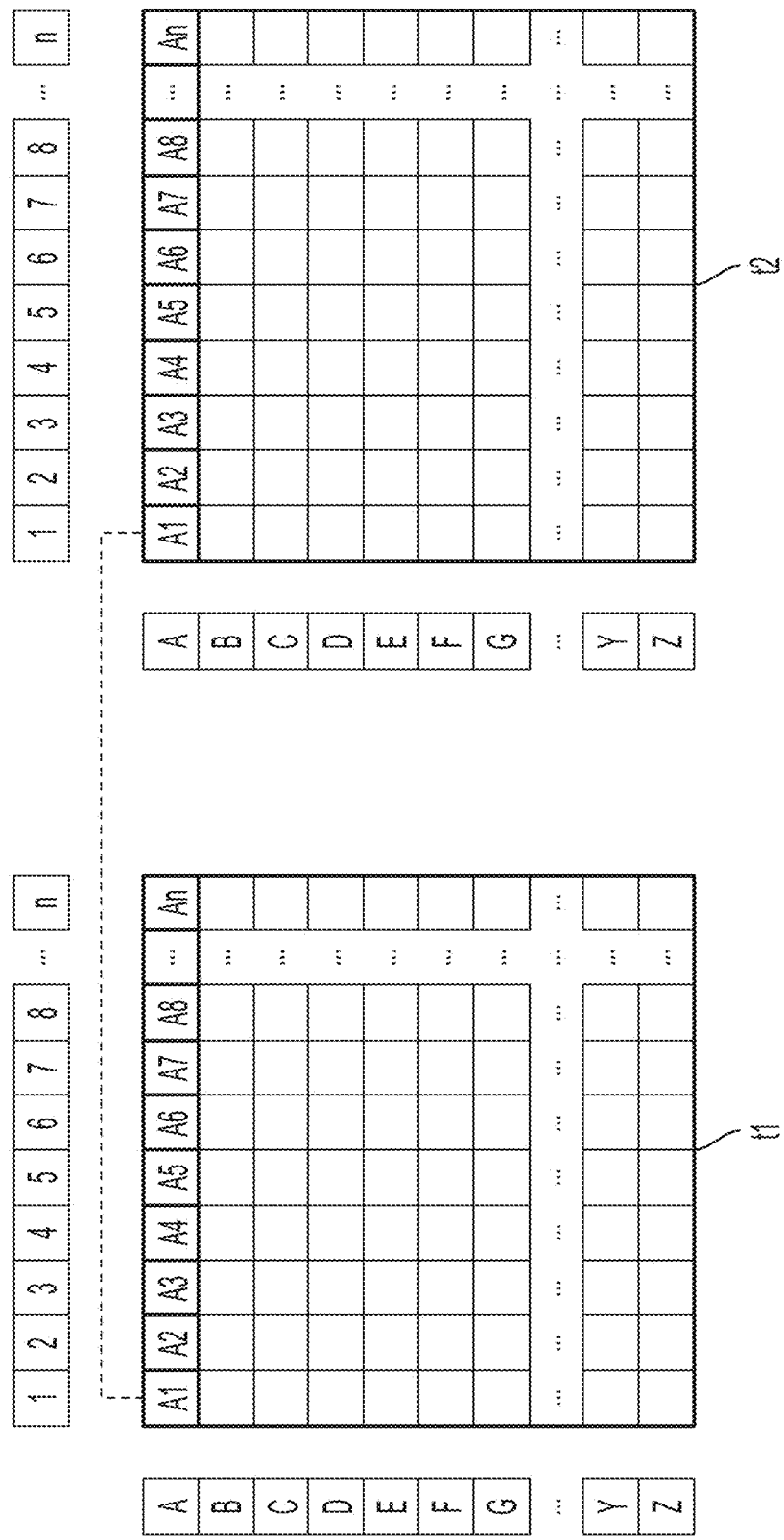
FIG. 45 illustrates a method to determine whether a sample has self-stabilized, based on comparing the intensity of pairs of corresponding pixels belonging to test scans acquired at different moments in time, according to illustrative embodiments of the present disclosure.

FIG. 45 illustrates a method to determine whether a sample has self-stabilized, based on comparing the intensity of pairs of corresponding pixels belonging to test scans acquired at different moments in time. For example, the mean absolute intensity difference between pixels belonging to the line of pixels A of two different scan patterns may be compared to a predetermined (e.g., predefined) threshold or to the intensity of the pixels. Let $I(A_1, t_1)$ be the intensity value of pixel $A_1$ at moment at time $t_1$, $I(A_1, t_2)$ be the intensity value of pixel $A_1$ at time $t_2$, and so on. The mean absolute intensity difference $\Delta(t_2-t_1)$ between corresponding pixels belonging to the line of pixels A of two different scan patterns is:

$$\Delta(t_2-t_1)=(1/n)*[|I(A_1,t_2)-I(A_1,t_1)|+|I(A_2,t_2)-I(A_2,t_1)|+\ldots+|I(A_n,t_2)-I(A_n,t_1)|]$$

In some embodiments, $\Delta(t_2-t_1)$ may be compared to a predetermined threshold based on intensity variation in interior pixels of tile(s) in reference images of the same tissue sample type (e.g. breast lumpectomy). In some embodiments, a relative stabilization index may be obtained by dividing $\Delta(t_2-t_1)$ by the sum of the intensity of pixels in line A at time $t_2$ (or $t_1$):

$$S(t_2-t_1)=\Delta(t_2-t_1)/[I(A_1,t_2)+I(A_2,t_2)+\ldots+I(A_n,t_2)]$$

$S(t_2-t_1)$ may be compared to a predetermined (e.g., predefined) threshold to determine whether sample motion is occurring or has occurred. The predetermined (e.g., predefined) threshold may be determined empirically or computationally for, for example, a given sample type (e.g., material and/or size).

Figure 46:
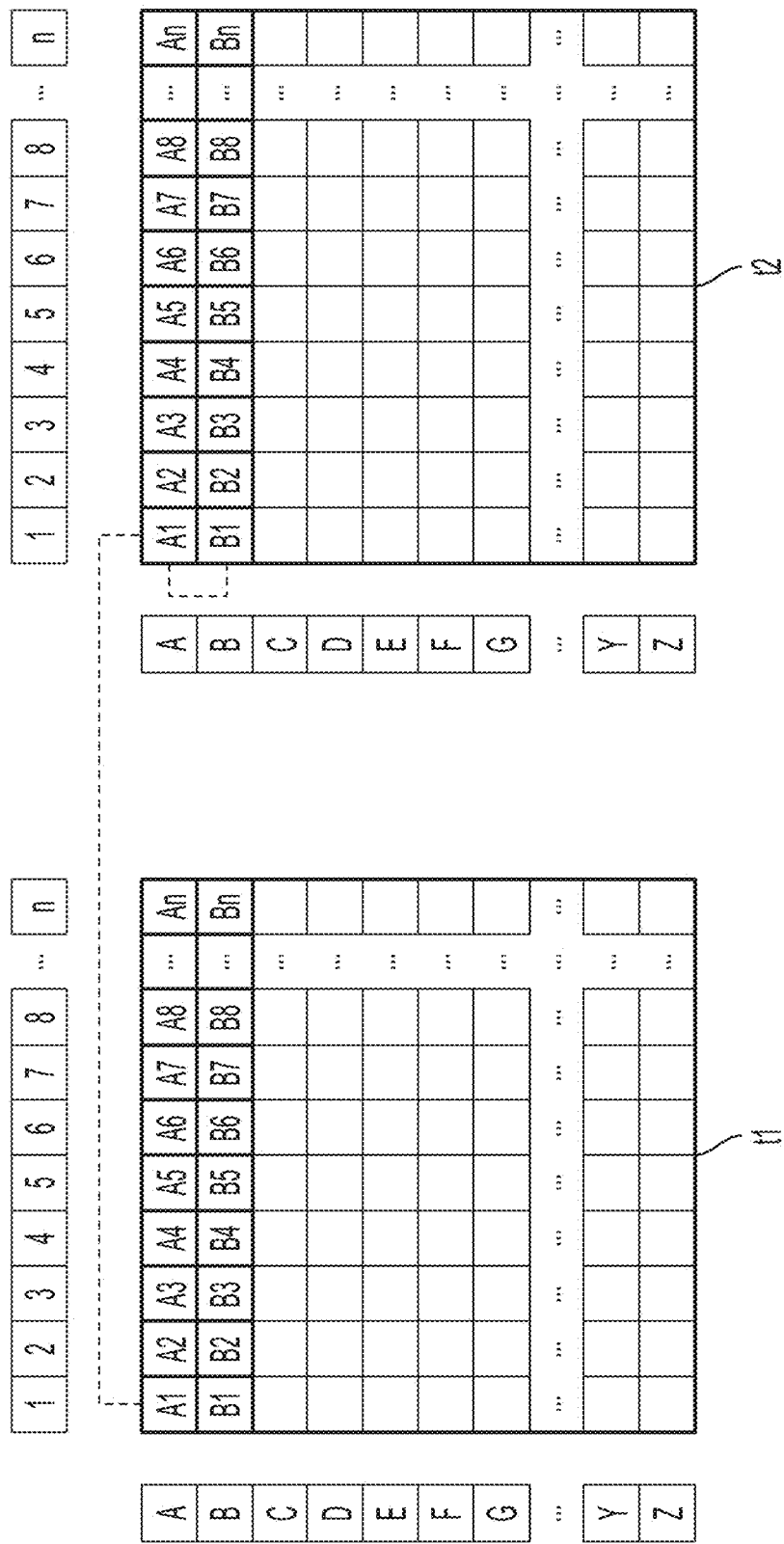
FIG. 46 illustrates a method to determine whether a sample has self-stabilized, based on comparing the intensity of pairs of corresponding pixels belonging to test scans acquired at different moments in time to the intensity of pairs of adjacent pixels belonging to the same test scan, according to illustrative embodiments of the present disclosure.

FIG. 46 illustrates a method to determine whether a sample has self-stabilized, based on comparing the intensity of pairs of corresponding pixels belonging to test scans acquired at different moments in time to the intensity of pairs of adjacent pixels belonging to the same test scan. In some embodiments, the intensity comparison may involve calculating the intensity difference between corresponding pixels belonging to two different test scans and comparing it to the intensity difference between adjacent pixels within the same test scan. For example, the mean absolute intensity difference between pixels belonging to the line of pixels A of two different scan patterns may be compared to the mean absolute intensity difference between adjacent pixels belonging to the line of pixels A and B of the same test scan. Let $I(A_1, t_1)$ be the intensity value of pixel $A_1$ at moment at time $t_1$, $I(A_1, t_2)$ be the intensity value of pixel $A_1$ at time $t_2$, and so on. The mean absolute intensity difference $\Delta(t_2-t_1)$ between corresponding pixels belonging to the line of pixels A of two different scan patterns is:

$$\Delta(t_2-t_1)=(1/n)*[|I(A_1,t_2)-I(A_1,t_1)|+|I(A_2,t_2)-I(A_2,t_1)| + \ldots + |I(A_n,t_2)-I(A_n,t_1)|]$$

The mean absolute intensity difference between adjacent pixels belonging to the line of pixels A and B of the same test scan is:

$$\Delta \text{int}=(1/n)*[|I(A_1)-I(B_1)|+|I(A_2)-I(B_2)|+ \ldots +|I(A_n)-I(B_n)|]$$

And the stabilization index $S(t_2-t_1)$ is:

$$S(t_2-t_1)=\Delta(t_2-t_1)/\Delta \text{int}$$

In the above example, a stabilization index S of 1 indicates that the intensity difference of between the two test scans is equal to the intensity difference between pairs of adjacent pixels within the tile. If the time difference between the two test scans corresponds to the imaging time of the full imaging scan, and if the resolution of the test scan is the same as that of the full imaging scan, this would indicate that an image acquired after the last test scan would not present motion artifacts resulting from sample motion larger than 1 pixel. It will now become apparent to one of skill in the art that similar implementations may be used (e.g., implementations in which more than 2 lines of pixels are used for the calculation of the mean absolute intensity difference between adjacent pixels and/or for the calculation of the stabilization index).

In some embodiments, the time interval between the test scans to be compared needs to be carefully chosen. If the time difference between the test scans that are compared is too small, small motions of the sample may not be perceptible at this time scale, while yet resulting in visible motion artifacts in the full image that is acquired afterwards. On the contrary, if the time difference is too large, motions of the sample that have occurred early in the observation period will lead to believing that the sample still is in motion, even though it may have stabilized in the meantime, thus resulting in a waste of time. A good compromise between the two results in an ideal time difference between the test scans to be compared of about 1-10 seconds (e.g., 2-8 seconds, 3-7 seconds). Of course, the test scans may be acquired at a higher frequency, but compared to on another separated in time by this ideal time difference. This would result in a higher refresh rate.

The parameters of the test scan may be such that one or more tiles of the test scan may not be sensitive enough to sample motion (e.g., if there is no tissue structure of sufficient spatial frequency modulation and/or contrast in the tile area of the test scan). It may thus be advantageous to consider areas made up from multiple tiles when assessing whether sample motion has occurred or is occurring. For example, a unique stabilization index may be calculated for each area that is made up from multiple tiles (e.g., the stabilization index of each tile of an area may be averaged to give the stabilization index for that area). These areas may be constructed from isotropic binning (e.g., grouping 2×2 tiles, 3×3 tiles, 4×4 tiles, 6×6 tiles, 8×8 tiles, 16×16 tiles) of from anisotropic binning (e.g., 1×2 tiles, 3×4 tiles, 6×8 tiles, 1×12 tiles). As sample motion sometimes is localized to a relatively small area, it may be counterproductive to combine too many tiles together in a given area, especially if the tiles are located relatively far away from one another. A good compromise may be obtained for areas that are at least 2 tiles, but no more than 16 tiles across and totaling between 4 and 256 tiles (e.g., 2×2, 3×3, 4×4, 6×6, 8×8, 9×9, 12×12, 16×16, 3×4, 6×8, 9×12).

In some embodiments, a method comprising monitoring intensity of pixel(s) (e.g., a single pixel) includes determining a metric (e.g., a statistic) for each of a plurality of tiles or binned tiles in an image. Subsequently, a difference or statistic may be determined as a function of time to determine whether sample motion is occurring or has occurred over a period of time. For example, intensity may be averaged over each tile for each of a plurality of points of time (during a period of time). Sample motion having occurred may then be determined based on comparing fluctuations in the average of each of the plurality of tiles over time (e.g., where it is determined to have occurred if the fluctuation exceeds a threshold over the period of time). As another example, changes in a min or max average intensity or changes in a difference between min and max average intensities or differences between min or max average intensities in adjacent tiles may all be used as a basis to determine whether a sample is moving or has moved (e.g., whether sample motion has occurred). (It will be clear to one ordinary skill in the art that such metrics may also be used with respect to single pixels as opposed to tiles or average intensity of tile(s). For example, changes in a min or max intensity of a single pixel or changes in a difference between min and max intensity of a pixel or differences between min or max intensities in adjacent single pixels may all be used as a basis.)

Figure 47B:
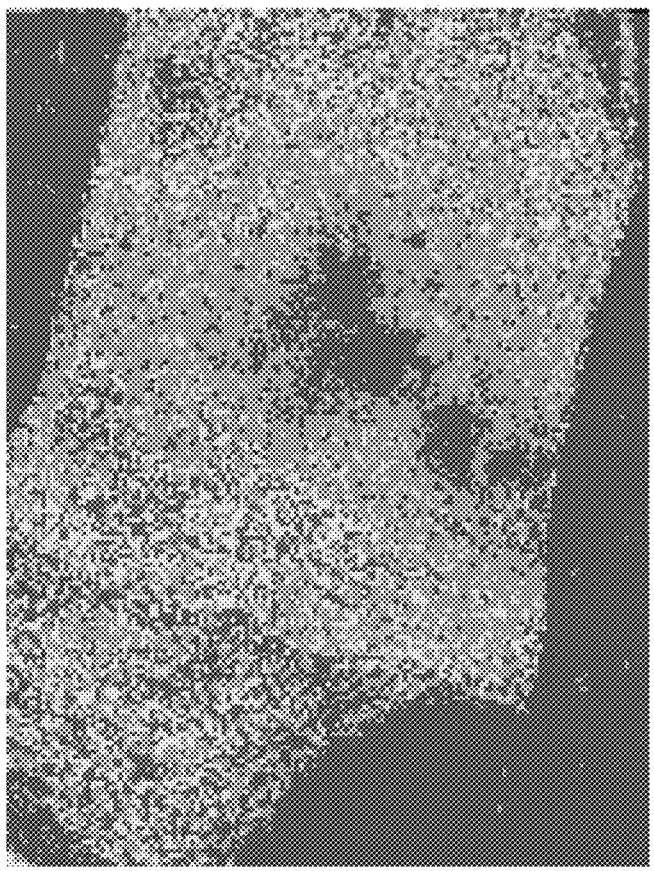
FIGS. 47A-B illustrate example representations of a stabilization index and of a corresponding motion index, according to illustrative embodiments of the present disclosure.
Figure 47A:
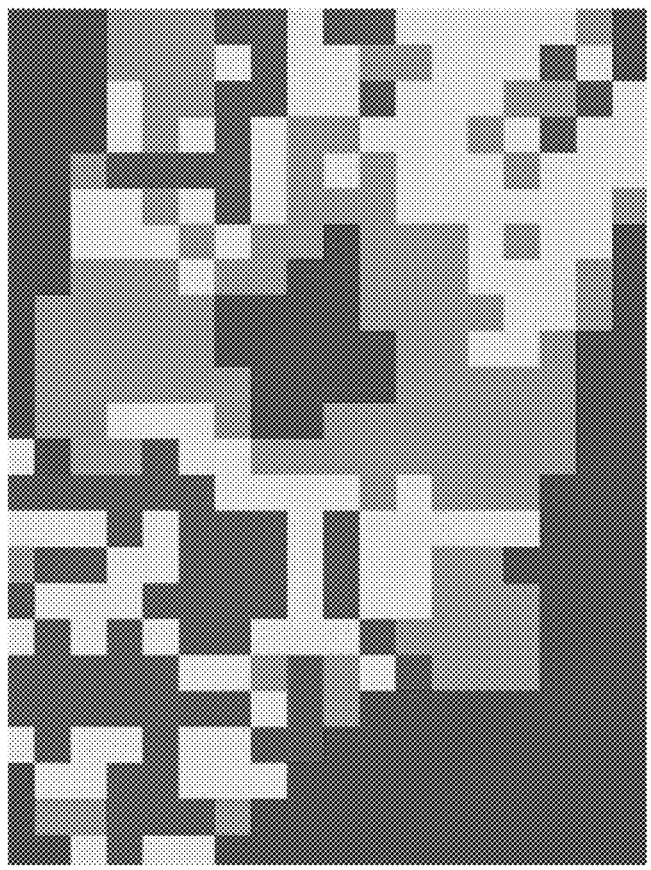

The stabilization index as calculated above may be compared to a predetermined (e.g., predefined) threshold to reveal the presence or absence of significant sample motion. The predetermined (e.g., predefined) threshold may be determined empirically or computationally for, for example, a given sample type (e.g., material and/or size). Given its similarity with the motion index presented above, the stabilization index may also be used as a predictive indicator of the magnitude of the sample motion that will be observed in an image that would be acquired. The stabilization index may thus be represented as a motion index to reveal sample motion that will result in motion artifacts of different magnitudes, corresponding to those presented with the motion indices above. FIGS. 47A-B are a colormap representation of sample motion. FIG. 47A is a representation of the stabilization index calculated from test scans, where one stabilization index is calculated for an ensemble of 8×8 tiles. The colormap reads from blue to green to yellow to red with increasing sample motion. FIG. 47B is a representation of the motion index calculated from the full image acquired immediately after the last test scan used for FIG. 47A. There is no binning, so one motion index per tile is represented. The colormap reads from blue to green to yellow to red with increasing sample motion artifact magnitude. In the above example, the color blue represents a motion index $M_{\alpha\beta}$ below 1.5 (no motion artifacts or minor motion artifacts that would not even be noticed by the user during image interpretation); the color green represents a motion index $M_{\alpha\beta}$ between 1.5 and 2.75 (minor motion artifacts that would not affect user comfort for image interpretation); the color yellow represents a motion index $M_{\alpha\beta}$ between 2.75 and 4 (major motion artifacts that would be annoying for the interpretation of the image); and the color red represents a motion index $M_{\alpha\beta}$ above 4 (critical motion artifacts that may adversely impact image interpretation).

Figure 23:
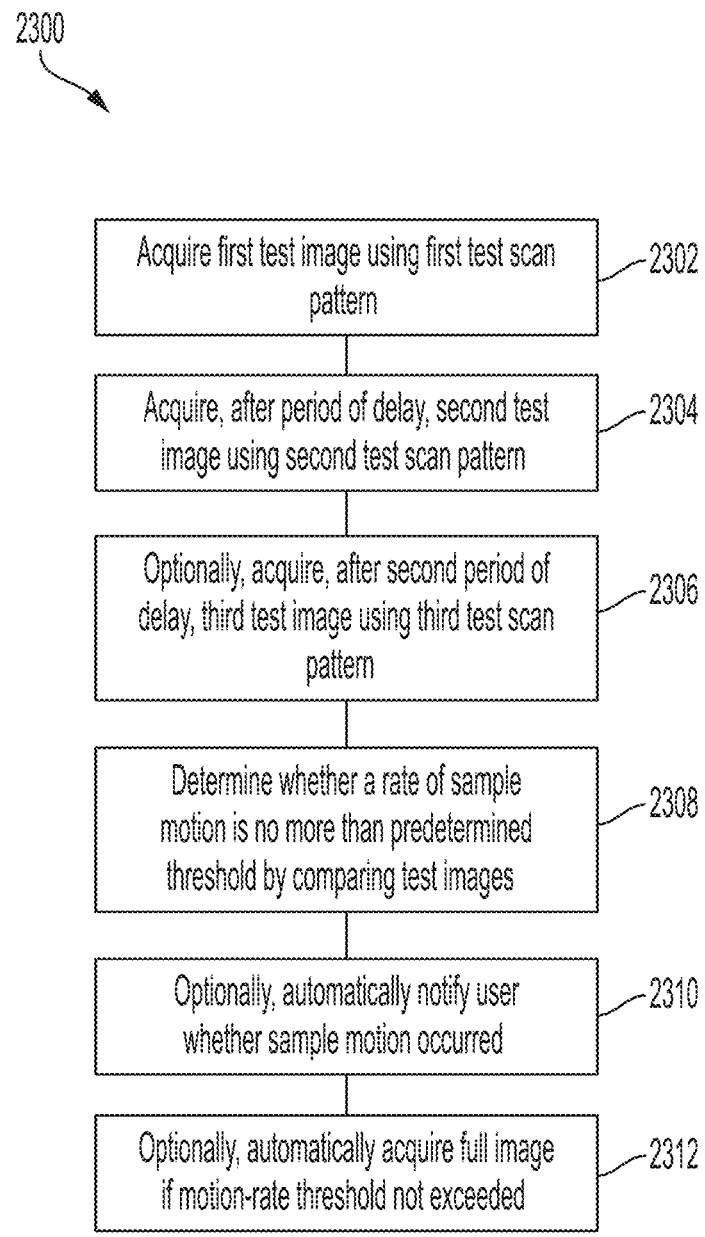
FIG. 23 is a process diagram of a method for determining whether a sample has moved, according to illustrative embodiments of the present disclosure.
Figure 48:
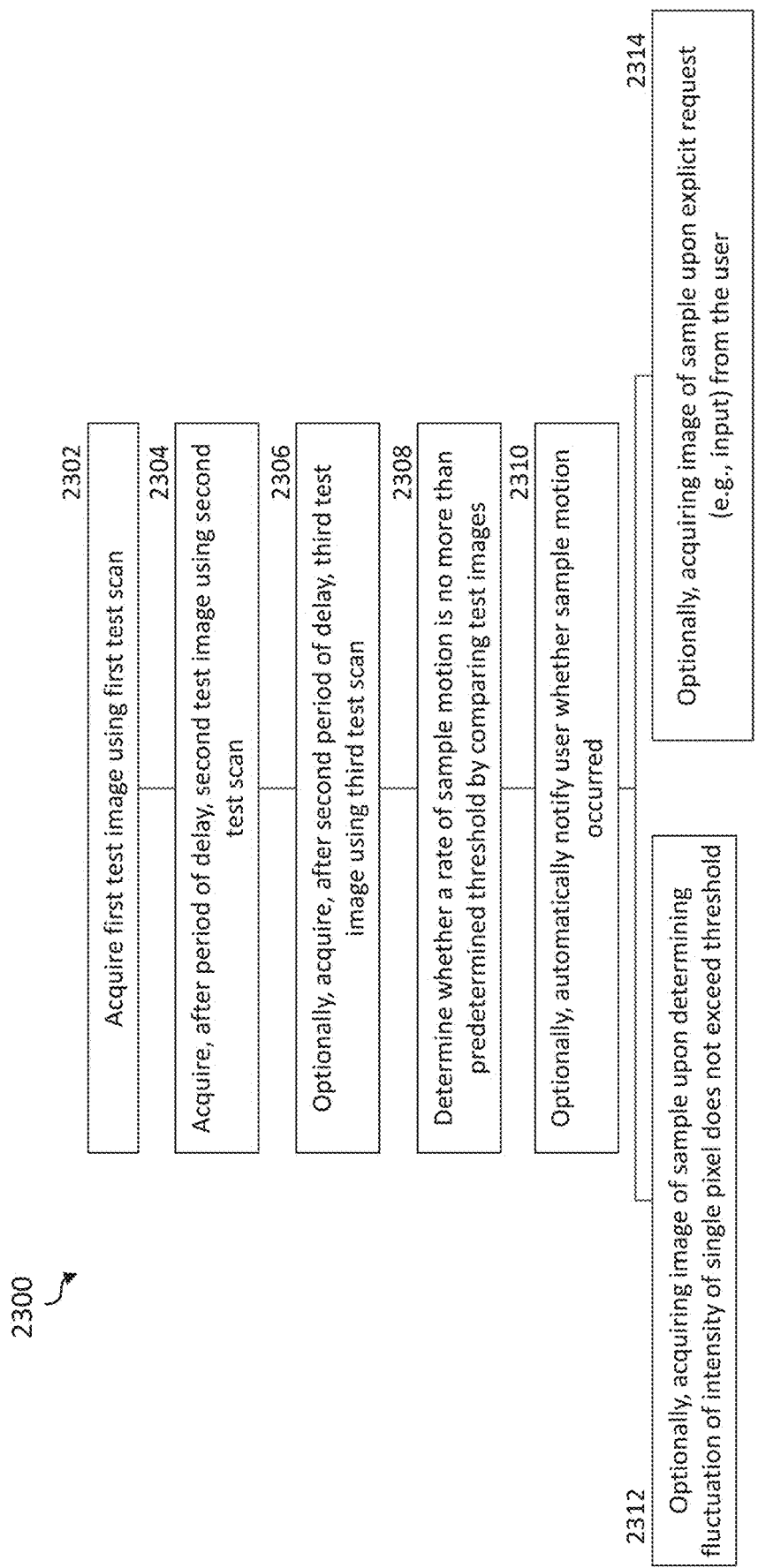
FIG. 48 is a process diagram of a method for determining whether a sample has moved, according to illustrative embodiments of the present disclosure.

FIGS. 23 and 48 are process diagrams of a method 2300 for determining whether a sample has moved. In step 2302, a first test image is acquired using a first test scan pattern. In step 2304, a second test image is acquired using a second test scan pattern after a first period of delay. The second test scan pattern may be the same as the first test scan pattern or may be different (e.g., the first test scan pattern can be an inward spiral and the second test scan pattern can be an outward spiral). The second test scan pattern may have a size corresponding to a size of the first test scan pattern or a different size. No manipulation of the sample (e.g., by a user) occurs between acquiring the first test image and acquiring the second test image; of course, natural sample motion (e.g., due to relaxation) may occur between acquiring the first and second test images. The first period of delay may be at least 2 seconds (e.g., at least 5 seconds) and no more than 60 seconds (e.g., no more than 30 seconds); the first period of delay may be chosen based on sample characteristic(s), such as sample size or sample material. The two test scans may also be acquired immediately one after another, with no period of delay. In such cases, the time difference between scan points in the two test scans corresponds to the duration of test scan. In optional step 2306, a third test image is acquired using a third test scan pattern after a second period of delay. The third test scan pattern may be the same as one or more of the first and/or second test scan patterns or different. The second period of delay may be the same as the first period of delay or different (e.g., may be chosen based on an amount or rate of sample motion determined by comparing the first and second test images, such that step 2306 occurs after step 2308). A sample stabilization monitoring tool may continuously acquire test scans, with or without a period of delay between each test scan, and determine sample motion by comparing one test scan to one or more test scans that is(are) the immediate previous/next test scan(s) or test scan(s) separated in time by one or more other test scans.

A period of delay may be the time it takes to reset to a starting point of a scan pattern and begin scanning again or the time it takes to make another scan (e.g., where every other scan is compared or otherwise analyzed).

In step 2308, a rate of sample motion is determined based at least in part on comparing the first test image to the second test image. In some embodiments, the first test image and/or the second test image are also compared with the third test image (from step 2306). In some embodiments, a sample motion rate is determined based on the comparison and sample motion is determined to have occurred if the sample motion rate exceeds a predetermined sample-motion-rate threshold. In some embodiments, an amount of sample motion is determined and compared to a sample motion threshold.

In optional step 2310, a user is notified (e.g., automatically) as to whether sample motion has occurred (e.g., and also a rate or amount of sample motion between acquisition of the first and second test images). A system may notify a user about the stabilization state of the sample to support the user in deciding when best to launch an image acquisition. In some embodiments, a user may be notified via a single event automatically triggered when sample motion meets a predetermined rule (e.g., when sample motion has become sufficiently small not to produce visible motion artifacts in the full image to be acquired). In some embodiments, a user is continuously notified of the current state of sample motion via a continuously updated indicator (e.g., graphical or textual), that may be reduced to a single scalar (e.g., color or symbol if graphical or value (e.g., measure) if textual) for the entire sample. In some embodiments, a user is continuously notified of the current state of sample motion via a continuously updated indicator array, that locally represents the state of sample motion (e.g., displayed as a color-coded miniature map of the sample).

In optional step 2312, a full image is acquired (e.g., automatically) if sample motion has not occurred (e.g., if a sample-motion-rate threshold is not exceeded).

In an additional optional step 2314, a full image is acquired upon an explicit request from the user. In application contexts under high time-pressure, a user may want to be empowered with the ability to launch an acquisition at any moment (s)he feels appropriate (e.g., based on a continuous notification of the current state of sample motion). See FIG. 48, which shows an additional process flow for method 2300.

Test images can be compared in any manner that is suitable to determine sample motion. The particular manner of comparison performed may depend on sample characteristic(s), such as which material(s) are in the sample or which features are to be imaged in the sample (e.g., cells, cell nuclei, or other cell organelles). In one example of a comparison, average intensity of each tile in a first test image is compared to average intensity of a corresponding tile in a second test image. A comparison between two test images may involve only comparing a portion of one test image to a corresponding portion of the other test image (e.g., comparing a subset of all tiles). In some embodiments, comparing test images comprises determining an intensity difference (e.g., of normalized intensity) (e.g., an average intensity difference) between a portion of the first test image and a spatially corresponding portion of the second test image. In some embodiments, determining the intensity difference comprises directly comparing a pixel of the first test image to a pixel of the second test image (e.g., comprises directly comparing a subset of pixels of the first test image to a subset of pixels of the second test image). Comparing test images may include using an image correlation technique (e.g., using an image mapping or image matching algorithm). In some embodiments, an image correlation technique determines a displacement vector based on intensity shifts between two test images that can be used to determine a rate or amount of sample motion.

Test scan patterns can generally be any size. Extremely small test scan patterns may make test images hard to compare, for example due to a particular image correlation technique used to compare test images. Relatively large test scan patterns may offer little time savings over simply performing full image acquisitions. In some embodiments, an area of a test scan pattern is no less than one thousandth (e.g., no less than one hundredth) and no more than one quarter (e.g., no more than one tenth or no more than one twentieth, no more than one hundredth) of an area of a unit cell of a micro optical element in an array of micro optical elements. In some embodiments, an area of a test scan pattern is no more than one hundredth of an area of a unit cell of a micro optical element in an array of micro optical elements. Using no more than one hundredth of a unit cell area may provide sufficient area for a sufficiently representative test scan while minimizing acquisition and comparison time, thereby expediting an overall imaging process. In some embodiments, each position in a first test scan pattern corresponds to a respective position in a second test scan pattern (e.g., the second test scan pattern is the first test scan pattern).

Whether sample motion has occurred may be directly or indirectly based on a rate of sample motion that occurs between acquisition of test images. Generally, when a sample moves less than a spatial resolution of an image, for example over a time it takes to scan a scan pattern, sample motion artifacts will be eliminated. Therefore, in some embodiments, determining whether sample motion has occurred (e.g., whether a sample has self-stabilized) includes determining whether a rate of sample motion exceeds a predetermined sample-motion-rate threshold based on comparing test images acquired by scanning over test scan pattern(s). The sample-motion-rate threshold may be predetermined, for example, based on an acquisition time that will be used for acquiring a full image (e.g., a 30 s or 60 s scanning time for a full scan pattern). In some embodiments, a predetermined sample-motion-rate threshold is no more than 1.5× a pixel size (e.g., an image resolution) of a full image to be acquired divided by an acquisition time of the full image. For example, a pixel size to be used for a full image (which also corresponds to a spatial step size in a full scan pattern) may be approximately 100 µm and an acquisition time to be used for the full image may be 25 s, such that a predetermined sample-motion-rate threshold is no more than 6 µm/s. In some embodiments, a predetermined sample-motion-rate threshold is a pixel size (e.g., an image resolution) of a full image to be acquired divided by an acquisition time of the full image. In some embodiments, a sample is said to be self-stabilized once motion of the sample over an image acquisition time is less than a resolution of the image acquired, so as to produce images in which no motion artifacts are visible. For example, a pixel size to be used for a full image (which may also correspond to a spatial step size in a full scan pattern) may be approximately 2 µm and an acquisition time to be used for the full image may be 40 s, such that a predetermined sample-motion-rate threshold is no more than 0.05 µm/s. As another example, a pixel size to be used for a full image (which may also correspond to a spatial step size in a full scan pattern) may be approximately 10 µm and an acquisition time to be used for the full image may be 2.5 s, such that a predetermined sample-motion-rate threshold is no more than 4 µm/s. A period of delay may correspond to an acquisition time of a full image to be acquired (e.g., be no more 10% longer and, optionally, no less than 10% shorter than the acquisition time). Such a period of delay may improve accuracy in assessing whether a sample has sufficiently self-stabilized prior to acquiring a full image. However, such a delay would not allow a user to save time, in comparison to simply acquiring the image and detecting the presence of sample motion, e.g. using the methods described above. A period of delay may correspond to only a fraction (e.g., no more than 50%, no more than 25%, no more than 10%) of an acquisition time of a full image to be acquired.

More than two test images may be compared (e.g., to each other as combinations of pairs) to determine whether sample motion has occurred and/or determine a rate of sample motion. A period of delay between test images may be constant or may vary. For example, where sample motion is determined to be occurring at a relatively high rate between a first two test scan patterns, a third test image may be taken after a longer delay period in order to avoid acquiring test images when it is highly likely that sample motion is still occurring at an undesirably high rate (e.g., self-stabilization has likely not occurred). Subsequent periods of delay between acquiring test images may be selected based on a rate of sample motion determined from comparison of prior (e.g., immediately prior) test images. For example, a period of delay before acquiring a third test image may be chosen (e.g., automatically) based on a rate of sample motion determined from comparison of a first test image and a second test image.

An alternative approach that may be even more time efficient is to monitor intensity versus time for only one pixel within each tile (or several pixels within each tile or one pixel every few tiles or several pixels every few tiles). For a parallel imaging system, for example including an array of micro optical elements, monitoring one pixel within each tile does not even require any motion of the optical elements (nor the sample). Intensity fluctuations in time would be larger for a sample that is moving significantly (e.g., compared to image resolution and/or imaging rate) than for a sample that is not moving significantly (e.g., compared to image resolution and/or imaging rate). A threshold amount may be set based on, for example, typical intensity variation between neighboring pixels in an image, below which intensity fluctuations of the single pixel(s) would indicate sample motion is not occurring (e.g., compared to image resolution and/or imaging rate). Typical intensity variation may be known and/or determined based on image parameters (e.g., resolution) and/or sample characteristic(s). The threshold amount may be predetermined or determined during monitoring, for example as a percentage of intensity fluctuation over an initial period.

Figures 24A, 24B:
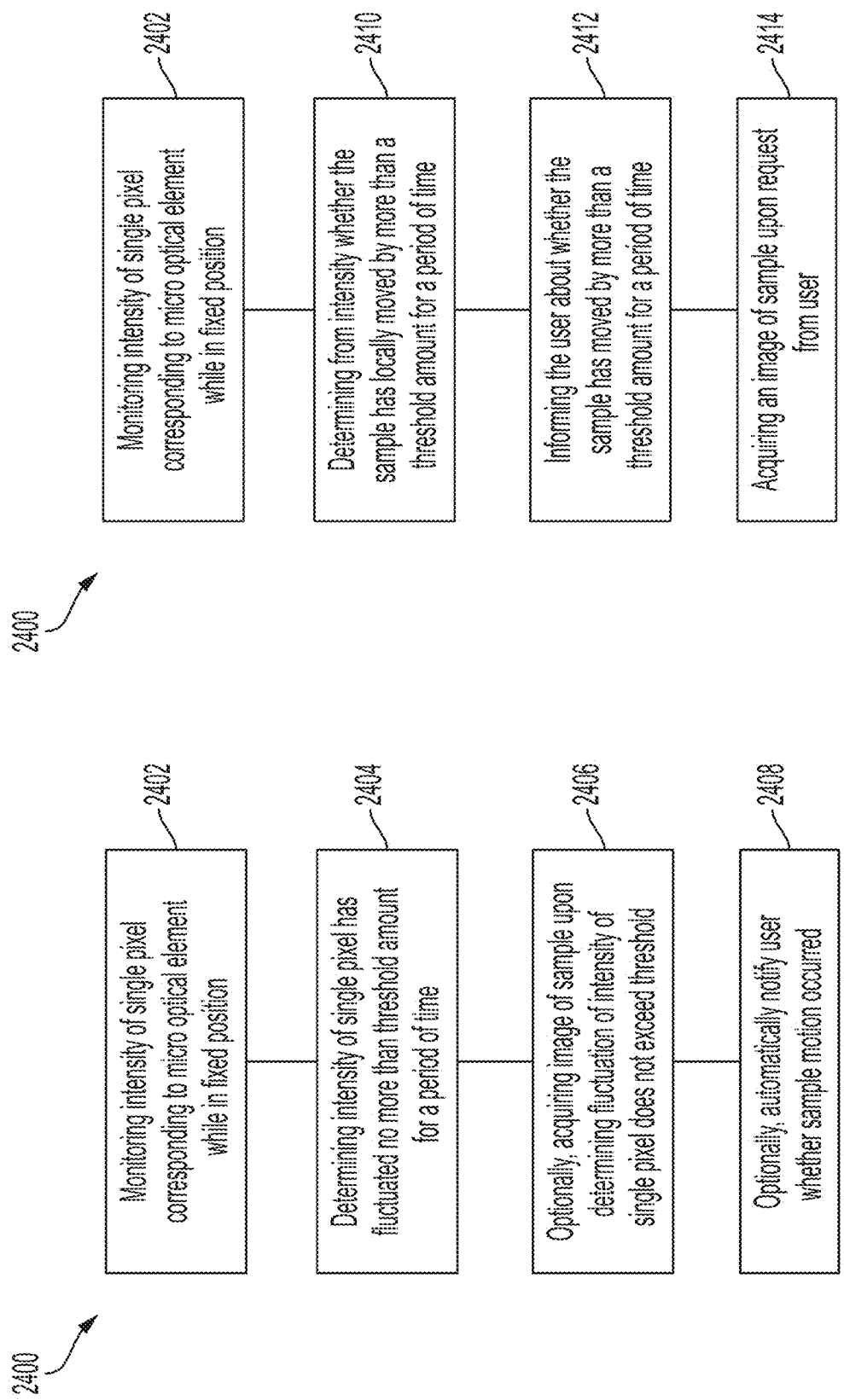
FIGS. 24A-B are process diagrams of methods for determining whether a sample has moved, according to illustrative embodiments of the present disclosure.

FIGS. 24A-B and 49 are process diagrams of methods 2400 for determining whether a sample has moved. In step 2402, a single pixel corresponding to a micro optical element in an array of micro optical elements is monitored while the micro optical element remains in a fixed position. Intensity of the single pixel is based on the amount of back-emitted light received by a detector that has been collected through the corresponding micro optical element. In step 2404, it is determined whether sample motion has occurred, which in this example is determined based, at least in part, on whether fluctuation of intensity of the single pixel was no more than a threshold amount for a period of time. In some embodiments, multiple single pixels are monitored simultaneously (e.g., each corresponding to a respective micro optical element in an array of micro optical elements, for example wherein the respective micro optical elements are at least a quarter, at least half, or all of the micro optical elements in the array) to determine whether sample motion has occurred. Determining whether sample motion has occurred may be based, at least in part, on fluctuation of each respective single pixel not exceeding a threshold amount; on an average intensity fluctuation of the respective single pixels not exceeding a threshold amount; or on fluctuation of an average intensity of the respective single pixels not exceeding a threshold amount. The period of time may correspond to an acquisition time of a full image to be acquired. In optional step 2406, an image of the sample is acquired (e.g., automatically) upon determining that fluctuation of intensity of the single pixel does not exceed the threshold amount for the period of time. In optional step 2408, a user is notified (e.g., automatically) (e.g., via a graphical user interface, e.g., a pop-up notification) whether sample motion has occurred based on the determination in step 2404. A system may notify a user about the stabilization state of the sample to support the user in deciding when best to launch an image acquisition. In some embodiments, a user may be notified via a single event automatically triggered when sample motion meets a predetermined rule (e.g., when sample motion has become sufficiently small not to produce visible motion artifacts in the full image to be acquired, e.g., as determined by a motion index). In some embodiments, a user is continuously notified of the current state of sample motion via a continuously updated indicator (e.g., graphical or text indicator), that may be reduced to a single scalar for the entire sample (e.g., a single color or symbol if graphical or a single value (e.g., measure) if text). In some embodiments, a user is continuously notified of the current state of sample motion via a continuously updated indicator array, that locally represents the state of sample motion (e.g., displayed as a color-coded miniature map of the sample).

In some embodiments of method 2400, as shown in FIG. 24B, in step 2410 intensity is used to determine whether a sample has locally moved by more than a threshold amount for a period of time. In step 2412, a user is informed that the sample has moved more than the threshold amount. In step 2414, an image is acquired upon an explicit request from the user. In application contexts under high time-pressure, a user may want to be empowered with the ability to launch an acquisition at any moment (s)he feels appropriate (e.g., based on a continuous notification of the current state of sample motion).

FIG. 49 shows an additional illustrative process flow for method 2400.

In some embodiments, an image of a sample is acquired (e.g., automatically, e.g., without user input) upon determining that intensity of a single pixel has fluctuated no more than a threshold amount for a period of time. In some embodiments, the threshold amount is a predetermined (e.g., predefined) threshold amount and the method comprises predetermining the threshold amount based on a resolution (e.g., a selected resolution) of the image to be acquired before beginning the monitoring. In some embodiments, the threshold amount is a predetermined (e.g., predefined) threshold amount and the method comprises predetermining the threshold amount based on one or more characteristics of the sample. In some embodiments, a threshold amount is no more than 20% or no more than 10%. Generally, as sample motion slows or stops, intensity fluctuations will be reduced because there are generally no sharp discontinuities in intensity between adjacent pixels and pixel drift due to sample motion will slow. Using absolute threshold amounts of no more than 20% or no more than 10% may be sufficient, in some embodiments, to reduce or eliminate noticeable sample motion artifacts from a subsequently acquired image. In some embodiments, the period of time is at least 2 s and no more than 90 s. In some embodiments, the period of time is at least 5 s and no more than 30 s.

Monitoring intensity of a single pixel may include making discrete measurements of back-emitted light received over separate short periods. For example, intensity at a first time may be based on back-emitted light received at a detector (e.g., a CCD or CMOS camera) through a micro optical element for a first short period (e.g., less than a millisecond) and intensity at a second time may be based on back-emitted light received at the detector through the micro optical element for a second short period that is an equal length of time to the first short period. There may be a period of delay between the first short period and the second short period (e.g., of at least 1 s and no more than 60 s). Determining whether a sample has moved may include processing (e.g., comparing) the intensity at the first time to the intensity at the second time. In some embodiments, the period of delay needs to be carefully chosen. If the period of delay is too small, small motions of the sample may not be perceptible at this time scale, while yet resulting in visible motion artifacts in the full image that is acquired afterwards. On the other end, if the period of delay is too large, motions of the sample that have occurred early in the observation period will lead to believing that the sample still is in motion, even though it may have stabilized in the meantime, thus resulting in a waste of time. In some embodiments, a good compromise between the two results in a period of delay between 2 and 30 seconds. Fluctuations of intensity over time may be based on discrete measurements of intensity made at a set of times during the monitoring. Of course, the intensity of a single pixel may be recorded at a higher frequency, but compared to the intensity of that same pixel at another time separated by this period of delay. This would result in a higher refresh rate.

Intensity fluctuations may be calculated simply by taking the absolute value of the difference in intensity of a pixel at two moments in time separated by a period of delay. Such an approach provides only sparse sampling and may therefore not be sensitive to intensity fluctuation that has occurred between the two sampled moments in time (e.g. the intensity may have changed and returned to more or less the same value). Intensity fluctuations may be calculated more sensitively by recording the pixel intensity at multiple moments in time and by taking the intensity difference between the maximum and the minimum values recorded over a period of time. Such an intensity fluctuation metric may also be normalized by dividing it by the time elapsed between the maximum and the minimum values. Intensity fluctuation may be calculated more sensitively by recording the pixel intensity at multiple moments in time and by taking the cumulative absolute difference in intensity between all successive values recorded over a period of time. Such an intensity fluctuation metric may be normalized by dividing it by the period of delay over which it is calculated. This approach has the advantage of being more sensitive to sample motions causing intensity of a pixel to vary non-monotonously in time. It has, however, the drawback of being also more sensitive to noise in intensity signals. It may therefore be desirable to smooth the intensity signals, e.g. with a moving average filter, before calculating the intensity fluctuation in this way. For example, for intensity values recorded continuously, some 1-5 ms apart, averaging (e.g., with a moving window filter) over at least 25 values may be desirable.

A period of delay may be the time it takes to reset to a starting point of a scan pattern and begin scanning again or the time it takes to make another scan (e.g., where every other scan is compared or otherwise analyzed).

When monitoring the intensity of a single pixel per tile, it is relatively likely, depending on the nature of the sample, that there is no tissue structure of sufficient spatial frequency modulation and/or contrast in the tile area of the test scan to provide enough sensitivity on sample motion. It may thus be advantageous to consider areas made up from multiple tiles when assessing whether sample motion has occurred or is occurring. For example, a unique intensity fluctuations metric may be calculated for an area that is made up from multiple tiles (e.g., the intensity fluctuation in each tile of an area may be averaged to give a mean intensity fluctuation for that area). These areas may be constructed from isotropic binning (e.g., grouping 2×2 tiles, 3×3 tiles, 4×4 tiles, 6×6 tiles, 8×8 tiles, 16×16 tiles) of from anisotropic binning (e.g., 1×2 tiles, 3×4 tiles, 6×8 tiles, 1×12 tiles). As sample motion sometimes is localized to a relatively small area, it may be counterproductive to combine too many tiles together in a given area, especially if the tiles are located relatively far away from one another. A good compromise may be obtained for areas that are at least 2 tiles, but no more than 16 tiles across and totaling between 4 and 256 tiles (e.g., 2×2, 3×3, 4×4, 6×6, 8×8, 9×9, 12×12, 16×16, 3×4, 6×8, 9×12).

Imaging workflow can be designed in a way that allows a user to execute one or more useful tasks during sample self-stabilization time period. For example, a low resolution, fast test image can be acquired during a sample self-stabilization period, to assure that sample positioning allows to scan a desired area of a sample (e.g., of a sample surface). In some embodiments, a test image will be acquired by an imaging system in priority over monitoring single pixel(s) (e.g., during method 2400) or small test image acquisition (e.g., during method 2300), which will resume after the test image is obtained. In some embodiments, a test image of the sample is acquired concurrently with monitoring of intensity of a single pixel (e.g., by acquiring the test image between discrete measurements of the intensity of the single pixel). In some embodiments, a measurement of intensity or test image acquisition is interrupted or cancelled by a low resolution test image acquisition. In some embodiments, a full (e.g., low resolution) test image of a sample is acquired between acquiring a first test image and a second test image. In some embodiments, acquiring a (e.g., low resolution) test image comprises scanning an array of micro optical elements over a scan pattern, wherein the scan pattern has an area corresponding to an area of a unit cell of a micro optical element in the array. In some embodiments, a test image of a sample is acquired (i) relatively quickly, (ii) at a relatively low resolution, or (iii) both relatively quickly and at a relatively low resolution and a subsequently acquired image of the sample is acquired (i) relatively slowly, (ii) at a relatively high resolution, or (iii) both relatively slowly and at a relatively high resolution, respectively.

Flattening Tools, Reshaping Tools, and Methods of their Use

Another approach to reducing sample motion artifacts is to act on the sample itself, to prevent it from moving during imaging. For that purpose, reshaping tools (e.g., clamps) are useful. While clamps (e.g., forceps) are normally intended for hand-held manipulation of objects, they can prove very practical to hold a sample in place and prevent it from moving during imaging. In general, heavy clamps work better to stabilize a sample and prevent undesired motions. Clamps with locking mechanisms may also be preferable, in order to stabilize a sample and prevent undesired motions. Physical manipulation, including flattening (described further subsequently), may be especially useful with large samples that may have long self-stabilization times.

In some embodiments, force exerted by a sample on a clamp will make them slide, if placed on a surface with a low friction coefficient. Increasing the friction coefficient between the forceps and the surface on which they rest helps in stabilizing a sample and preventing undesired motions. This can be achieved, e.g., by placing a rubber or silicone mat between a clamp and an imaging system surface, as described in further detail below. Alternatively or additionally, the material of an upper working surface of an imaging system surface and/or the material of a clamp that makes contact with the imaging system surface can be such as to provide a high friction coefficient. For example, stainless steel forceps with rubber coated finger rings may be used in some embodiments.

The shape of the clamp jaw may also impact how efficient it is at stabilizing (e.g., reshaping) a sample and preventing undesired motions. In some embodiments, one of three approaches is used to stabilize (e.g., reshape) a sample: (i) applying a force from above to flatten a sample, and accelerate the self-stabilizing motion; (ii) holding the sample from the side; or (iii) a combination of (i) and (ii). Approach (i) has an advantage in that it can maximize the surface of the tissue in contact with the imaging window and therefore the imaged tissue (e.g., it can reduce the "valleys" in the tissue). Approach (ii) reduces the direction (space) in which a sample can move (because the forces are compensated) and therefore reduces the self-stabilizing motion time. Approach (ii) may also have an advantage of enabling imaging surfaces of a sample on which the sample would not stay by itself.

In some embodiments, a sample is reshaped during imaging, for example to reduce or eliminate sample motion during imaging. FIG. 25 shows an imaging system 2500 on which a sample may be stabilized during imaging. Imaging system 2500 includes a transparent imaging window 2502 on which sample 2520 is disposed during imaging. Illumination light is provided to sample 2520, and back-emitted light is collected from sample 2520, during imaging. Sample 2520 is accessible to a user during imaging. Sample 2520 is disposed directly on sample dish 2504, which is disposed directly on transparent imaging window 2502. Imaging system 2500 includes an upper working surface 2506 that includes a high friction material (e.g., rubber or silicone). The high friction material may be removable (e.g., as a mat) or irremovable. Sample 2520 is reshaped using clamp 2510 that includes two gripping members 2512. The high friction material keep clamp 2510 in a desired position after a user releases clamp 2510 (e.g., prevents arms of clamp 2510 from spreading or retracting) thereby reshaping sample 2520, which can remain reshaped throughout imaging.

Figure 26:
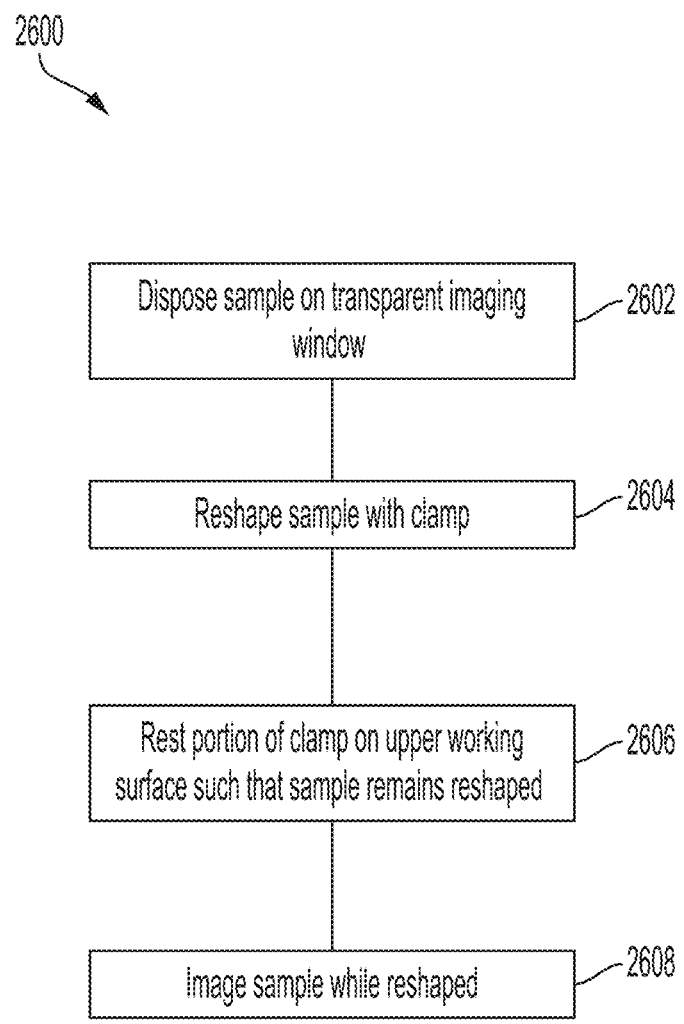
FIG. 26 is a process diagram of a method of reshaping a sample and imaging the reshaped sample, according to illustrative embodiments of the present disclosure.

FIG. 26 is a process flow diagram of an example of a method for stabilizing a sample [e.g., a biological sample (e.g., a resected tissue sample) (e.g., a stained biological sample)] during imaging. For example, imaging system 2500 can be used to perform the method. In step 2602, a sample is disposed on a transparent imaging window such that the sample is accessible to a user during imaging. In step 2604, a clamp is used to reshape the sample, for example by squeezing the clamp partially closed. In step 2606, a portion of the clamp is rested on an upper working surface of the imaging system such that the sample remains reshaped during subsequent imaging. For example a high friction material in the upper working surface maintains a position of the clamp after they are rested (e.g., as in imaging system 2500 in FIG. 25). In some embodiments, a sample remains reshaped even though slight movement (e.g., settling) occurs after resting the clamp. In step 2608, the sample is imaged while reshaped. A clamp may be a forceps or tweezer.

Figure 31:
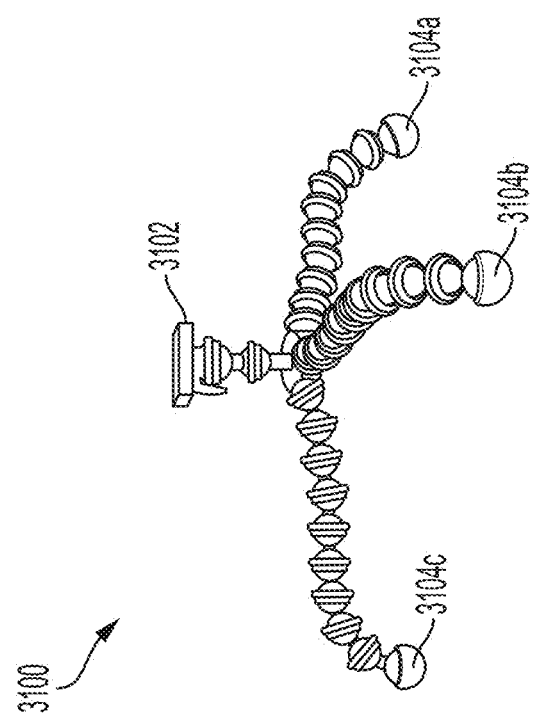
FIG. 31 is an illustration of a clamp, according to illustrative embodiments of the present disclosure.
Figure 30:
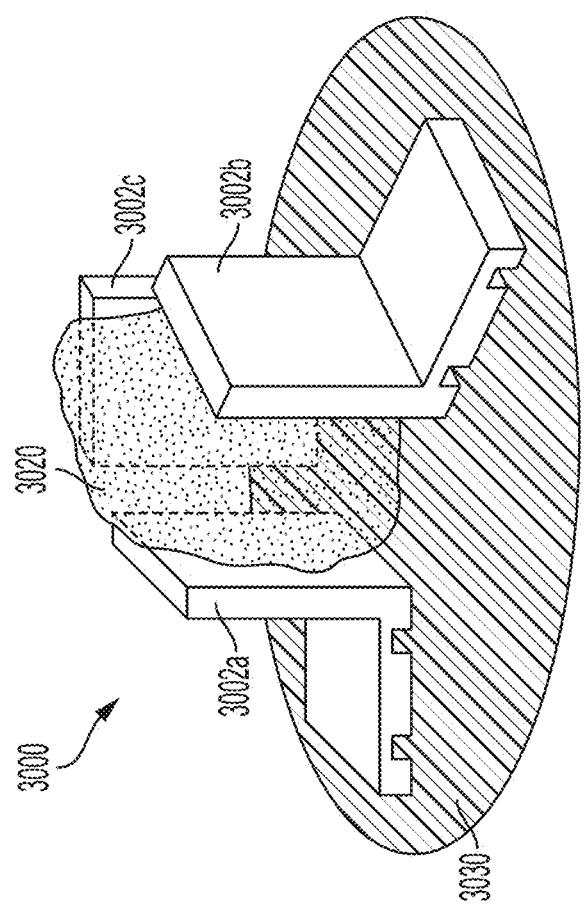
FIG. 30 is an illustration of a reshaping tool, according to illustrative embodiments of the present disclosure.

FIGS. 27-31 show examples of clamps or reshaping tools that may be used to reshape a sample during imaging. FIG. 27 shows clamp 2700 that includes manipulation elements 2702, lock 2704, hinge 2706 (e.g., a high friction hinge), and gripping members 2712. Gripping members 2712 have length 2713a and width 2713b. In some embodiments, a height and a length of a gripping member is at least 50% of a height and a length of a sample with which it is used, respectively. Larger gripping members better support reshaped samples during imaging. In some embodiments, a gripping member has a ribbed surface to improve friction with a sample. Gripping members 2712 each include an aperture 2714, which allows a sample to be reshaped without substantially deforming (e.g., compressing) it, such that sample relaxation that may cause sample motion artifacts is minimized. Lock 2704 can be used to maintain a particular shape of a sample. Alternatively or additionally, hinge 2706 may be a high friction hinge that resists movement (e.g., undesired opening) thereby improving sample stability during imaging and possibly reducing sample motion artifacts. FIGS. 28A-C illustrates horizontal ribs (FIG. 28A), vertical ribs (FIG. 28B), and hashed ribs (FIG. 28C). FIG. 29 shows an example of a clamp 2900 that includes manipulation elements 2902, hinge 2906, and two parallel gripping member 2912 that are holding sample 2902. FIG. 30 shows an example of a reshaping tool 3000 that includes three angled pieces 3002*a-c* that are reshaping sample 3020 on sample dish 3030. Angled pieces 3002*a-c* have flat surfaces contacting sample 3020, but angled or curved (e.g., circular) surfaces may also be used. Angled pieces 3002*a-c* may hold their position on sample dish 3030 due to one or more of weight, friction, suction, and magnets for example. FIG. 31 shows a posable clamp 3100 that includes three posable (e.g., flexible) arms 3104*a-c* and a manipulation element 3102. Manipulation element(s) may be used to handle clamps, for example during sample positioning and/or reshaping.

In some embodiments, a flattening tool is provided on a sample during imaging, for example in order to reduce or eliminate sample motion during imaging. FIGS. 32-35 show examples of flattening tools that may be used. It is contemplated that one or more features from one of the examples of a flattening tool may be used or adapted for use in other example(s) of a flattening tool. In some embodiments, a flattening tool is made of injection molded plastic. In some embodiments, a flattening tool comprises metal (e.g., is made from metal). In some embodiments, a flattening tool is sterilizable.

Figure 32:
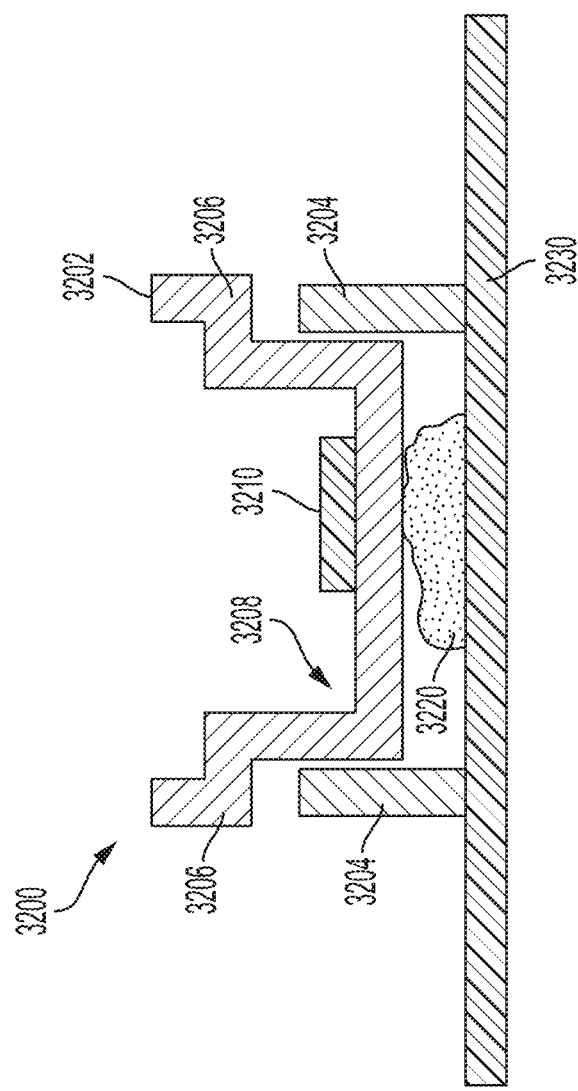
FIG. 32 is a schematic of a sample flattening tool, according to illustrative embodiments of the present disclosure.

FIG. 32 is a cross section of an example of a flattening tool 3200. Flattening tool 3200 includes a support member 3204 and a removable flattening member 3202. Support member 3204 has a shape that defines a channel. Sample 3220 sits inside support member 3204 during imaging. Sample 3220 may be reshaped in part by support member 3004. Removable flattening member 3202 includes retention lip 3206 and insertable portion 3208. Retention lip 3206 is sized and shaped to rest on support member 3204, while insertable portion 3208 is inserted into the channel defined by support member 3204. Support member 3204 may include one or more pieces. Flattening tool 3200 includes removable weight 3210, which may be placed on flattening member 3202 (e.g., on a top side of insertable portion 3208) during imaging to further flatten sample 3220. Removable weights may be made of, for example, metal and/or plastic. Sample 3220 and support member 3204 disposed on sample dish 3230. In some embodiments, sample 3220 and support member 3204 are disposed directly on a transparent imaging window during imaging. Support member 3204 has an annular cross section (when the cross section is taken perpendicular to the cross section shown in FIG. 32). In some embodiments, a support member has a rectangular cross section. When retention lip 3206 of flattening member 3202 rests on support member 3204, flattening member 3202 is disposed no more than 1 mm above a bottom of support member 3204.

Figure 33:
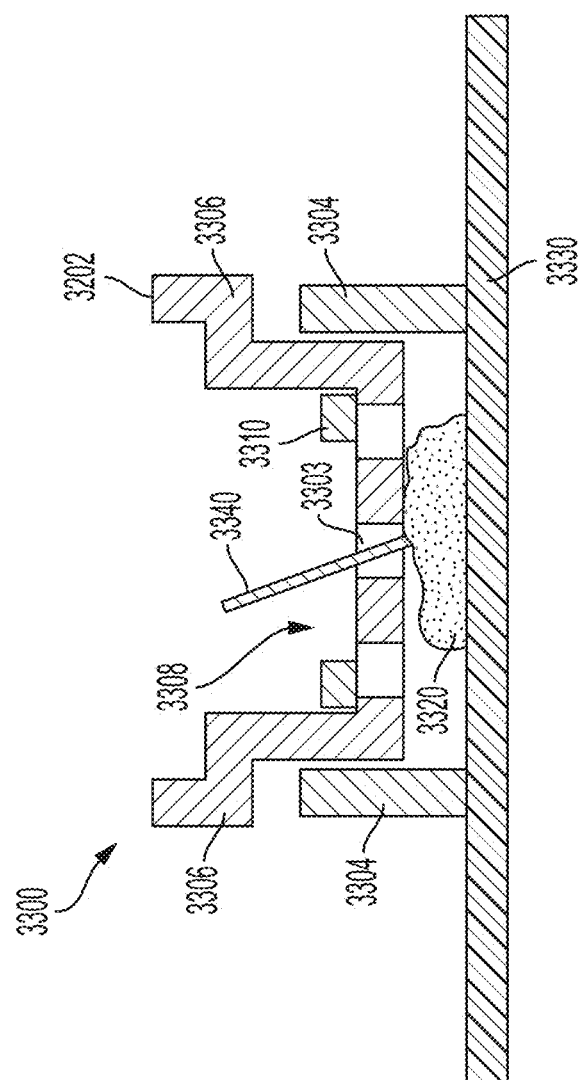
FIG. 33 is a schematic of a sample flattening tool, according to illustrative embodiments of the present disclosure.

FIG. 33 is a cross section of an example of a flattening tool 3300. Flattening tool 3300 includes similar features as flattening tool 3300. For example, flattening tool 3300 includes support member 3304, removable flattening member 3302 that includes retention lip 3306 and insertable portion 3308, and removable weights 3310. Flattening tool 3300 includes additional features not in flattening tool 3200. Specifically, removable flattening member 3302 has a shape that defines a plurality of through holes 3303 that are sized and shaped to accommodate a harpoon 3340 (e.g., are square or circular holes). For example, each hole may have a dimension of no more than 1 cm (e.g., no more than 5 mm). In some embodiments, a harpoon 3340 is used to mark a sample (e.g., an orientation or position of a sample) and, additionally or alternatively, can be used as a fiducial marker. For example, one or more harpoons may be placed in a patient prior to surgery in order to identify a portion of tissue to be resected (e.g., the tip of the harpoon(s) may be located near a cancerous region). A removable flattening member that has one or more holes can accommodate harpoon(s) thereby reducing or obviating the need to remove the harpoon(s) prior to imaging, which may otherwise be time consuming and/or damaging to a tissue sample. Multiple holes can allow a sample to be oriented in different ways while leaving the harpoon in approximately its original position and/or accommodate multiple harpoons. Although not shown in FIG. 33, support member 3304 may additionally or alternatively have a shape that defines one or more holes sized and shaped to accommodate a harpoon. Removable weights 3310 do not cover at least one of the holes in removable flattening member 3302. Flattening tool 3300 is flattening sample 3320 that is disposed on sample dish 3330.

Figure 34:
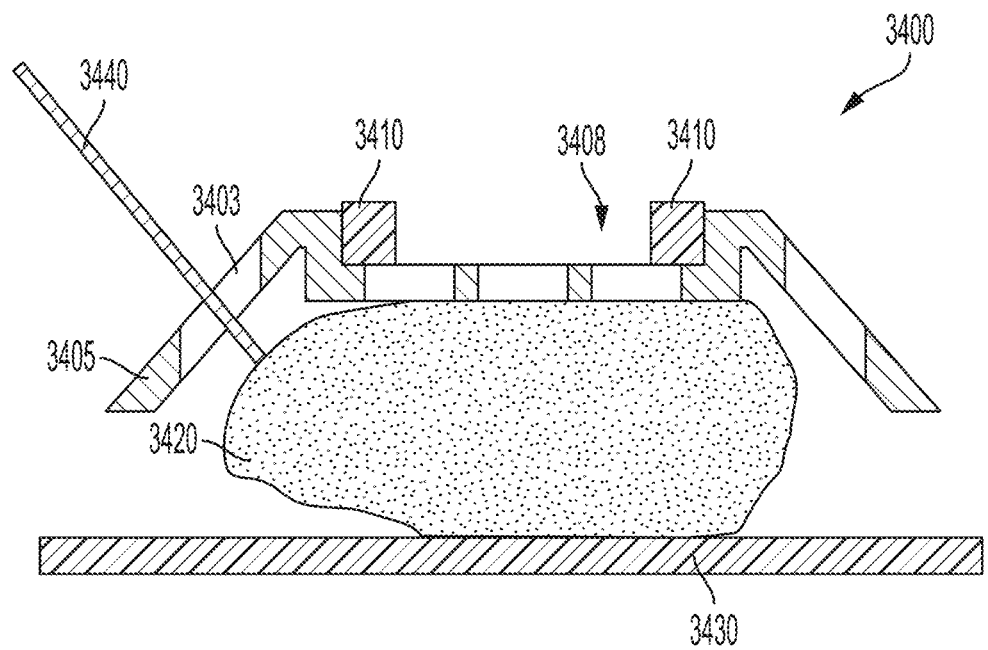
FIG. 34 is a schematic of a sample flattening tool, according to illustrative embodiments of the present disclosure.

FIG. 34 is a cross section of an example of a flattening tool 3400. Flattening tool 3400 includes planar top portion 3408 and one or more wings 3405 extending downward from top portion 3408. In flattening tool 3400, one or more wings 3405 is a single annular shaped wing. In some embodiments, a flattening tool has a rotational symmetry (e.g., three-fold, four-fold, five-fold, or an infinite order of symmetry). One or more wings 3405 extend above a top surface of planar top portion 3408 thereby defining a recess in which to keep removable weights 3410 in place. Removable weights 3410 may be sized and shaped to be disposed at least partially (e.g., entirely) in the recess. One or more wings 3405 partially cover sample 3420 that is disposed on sample dish 3430. Flattening tool 3400 has a shape that defines one or more holes 3403 sized and shaped to accommodate harpoon 3440. The shape of one or more wings 3405 defines some of one or more holes 3403 and the shape of planar top portion 3408 defines others of one or more holes 3403. In some embodiments, a wing has a shape with no holes. In some embodiments, a planar top portion has a shape with no holes. In some embodiments, one or more holes (e.g., through a planar top portion) remain uncovered when one or more removable weights are disposed (e.g., on a top surface of the planar top portion).

Figure 35:
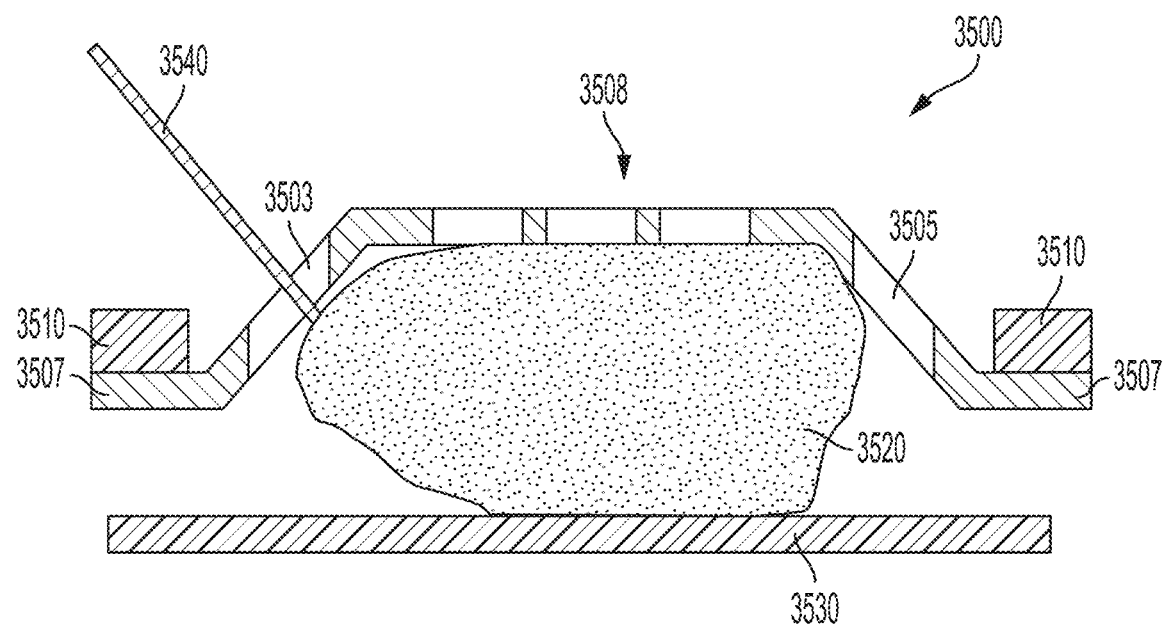
FIG. 35 is a schematic of a sample flattening tool, according to illustrative embodiments of the present disclosure.

FIG. 35 is a cross section of an example of a flattening tool 3500. Flattening tool 3500 has some similar features to flattening tool 3400. Flattening tool 3500 additionally includes one or more weight supports 3507. The inclusion of one or more weight supports 3307 extending from one or more wings 3505 allows removable weight(s) 3510 to be disposed around a perimeter of flattening tool 3500, which may assist in more evenly distributing the added weight to sample 3520. Sample 3520 is disposed on transparent imaging window 3530. One or more weight supports 3507 extend horizontally and parallel to planar top portion 3508.

Figure 38:
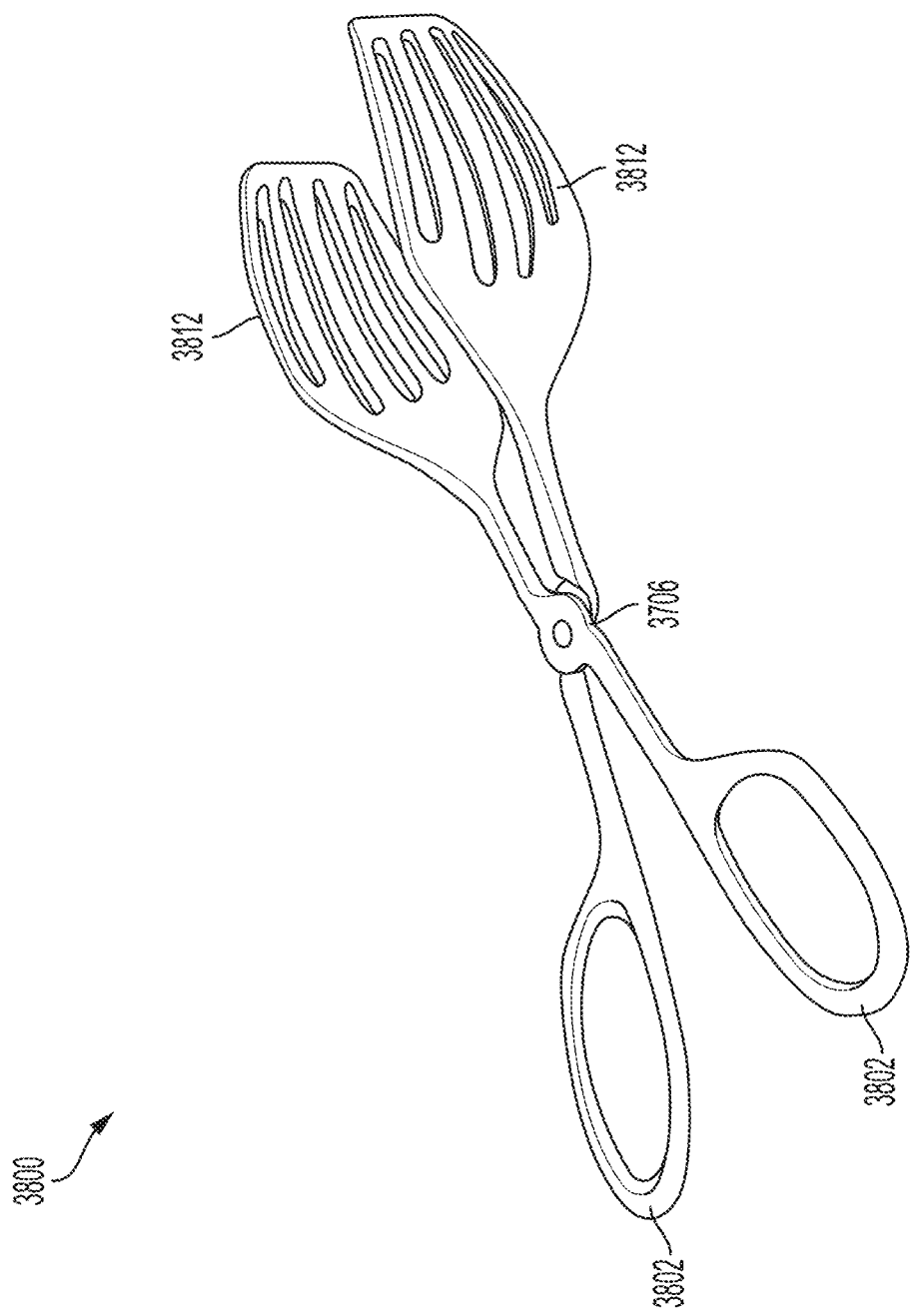
FIG. 38 is a schematic of a reshaping tool having concave gripping members, according to illustrative embodiments of the present disclosure.

A reshaping tool may include concave gripping members and/or gripping members with apertures. FIG. 36 is a cross section of reshaping tool 3600 that includes concave gripping members 3612 that hold convex sample 3620 to reshape it on sample dish 3630. FIG. 37 is a cross section of reshaping tool 3700 that includes gripping members 3712 having apertures holding convex sample 3720 (which protrudes through the apertures). Each of the gripping members have different shaped cross sectional perimeters of the apertures (elliptical on the left member and square on the right member). FIG. 38 shows reshaping tool 3800 that includes manipulation elements 3802, high friction hinge 3706, and concave gripping members 3812 that also include multiple apertures per member. High friction hinges and/or locks (e.g., as in reshaping tool 2700 illustrated in FIG. 27) can be particularly useful to prevent undesired sample motion during imaging (e.g., resulting from force exerted on the reshaping tool by a reshaped sample). Given a typical shape of certain tissue samples (e.g., breast lumpectomy samples), concave gripping members and gripping members with apertures can be particularly useful to help maintain sample in stable position (prevent movement) without substantially deforming (e.g., constraining or compressing) it. Deforming or constraining a sample may frequently lead to motion artifacts as the sample finds a way to relax.

Computer System and Network Implementations

Figure 39:
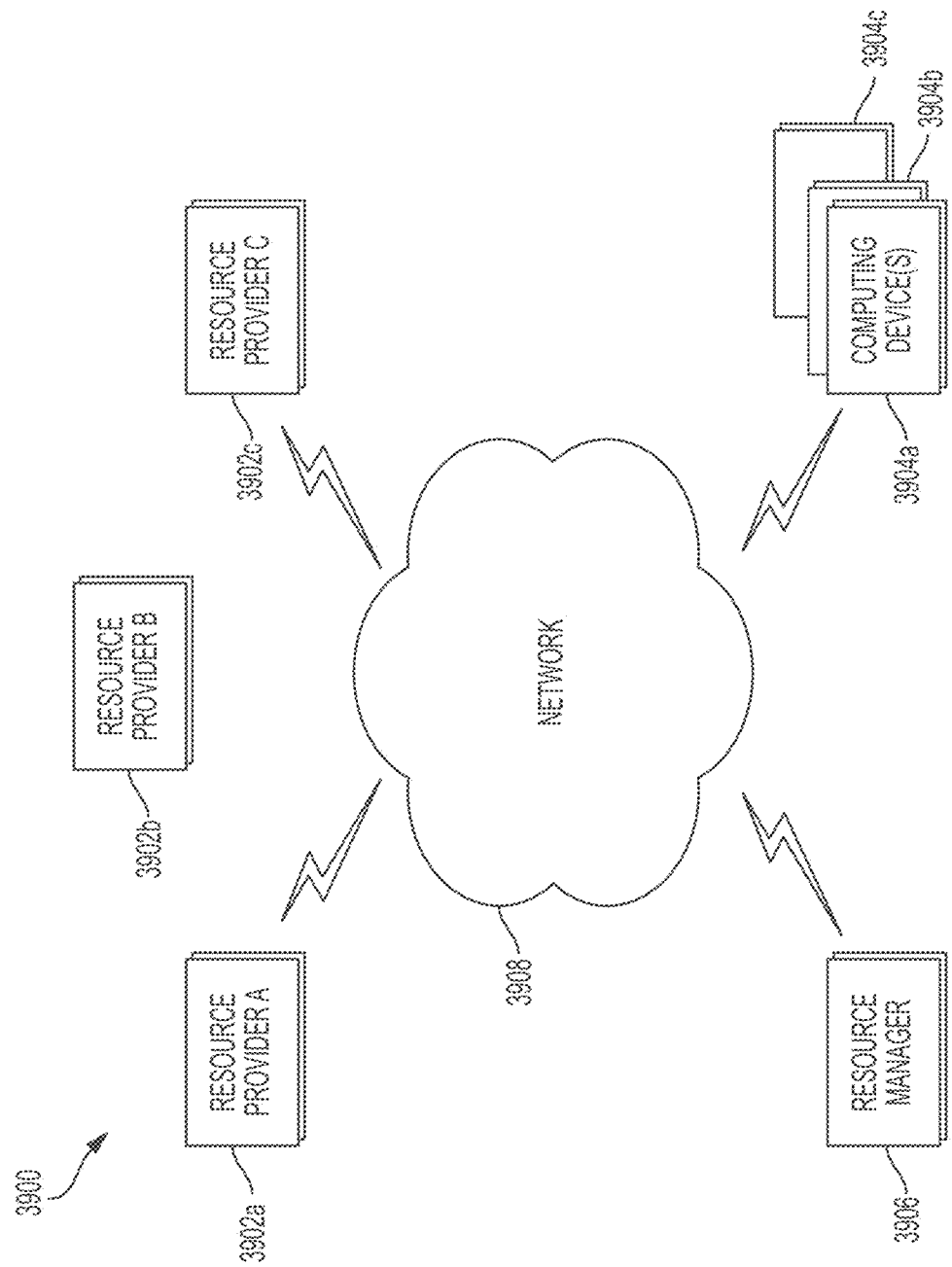
FIG. 39 is a block diagram of an example network environment for use in the methods and systems described herein, according to illustrative embodiments of the present disclosure.

Illustrative embodiments of systems and methods disclosed herein were described above with reference to computations performed locally by a computing device. However, computations performed over a network are also contemplated. FIG. 39 shows an illustrative network environment 3900 for use in the methods and systems described herein. In brief overview, referring now to FIG. 39, a block diagram of an illustrative cloud computing environment 3900 is shown and described. The cloud computing environment 3900 may include one or more resource providers 3902a, 3902b, 3902c (collectively, 3902). Each resource provider 3902 may include computing resources. In some implementations, computing resources may include any hardware and/or software used to process data. For example, computing resources may include hardware and/or software capable of executing algorithms, computer programs, and/or computer applications. In some implementations, illustrative computing resources may include application servers and/or databases with storage and retrieval capabilities. Each resource provider 3902 may be connected to any other resource provider 3902 in the cloud computing environment 3900. In some implementations, the resource providers 3902 may be connected over a computer network 3908. Each resource provider 3902 may be connected to one or more computing device 3904a, 3904b, 3904c (collectively, 3904), over the computer network 3908.

The cloud computing environment 3900 may include a resource manager 3906. The resource manager 3906 may be connected to the resource providers 3902 and the computing devices 3904 over the computer network 3908. In some implementations, the resource manager 3906 may facilitate the provision of computing resources by one or more resource providers 3902 to one or more computing devices 3904. The resource manager 3906 may receive a request for a computing resource from a particular computing device 3904. The resource manager 3906 may identify one or more resource providers 3902 capable of providing the computing resource requested by the computing device 3904. The resource manager 3906 may select a resource provider 3902 to provide the computing resource. The resource manager 3906 may facilitate a connection between the resource provider 3902 and a particular computing device 3904. In some implementations, the resource manager 3906 may establish a connection between a particular resource provider 3902 and a particular computing device 3904. In some implementations, the resource manager 3906 may redirect a particular computing device 3904 to a particular resource provider 3902 with the requested computing resource.

Figure 40:
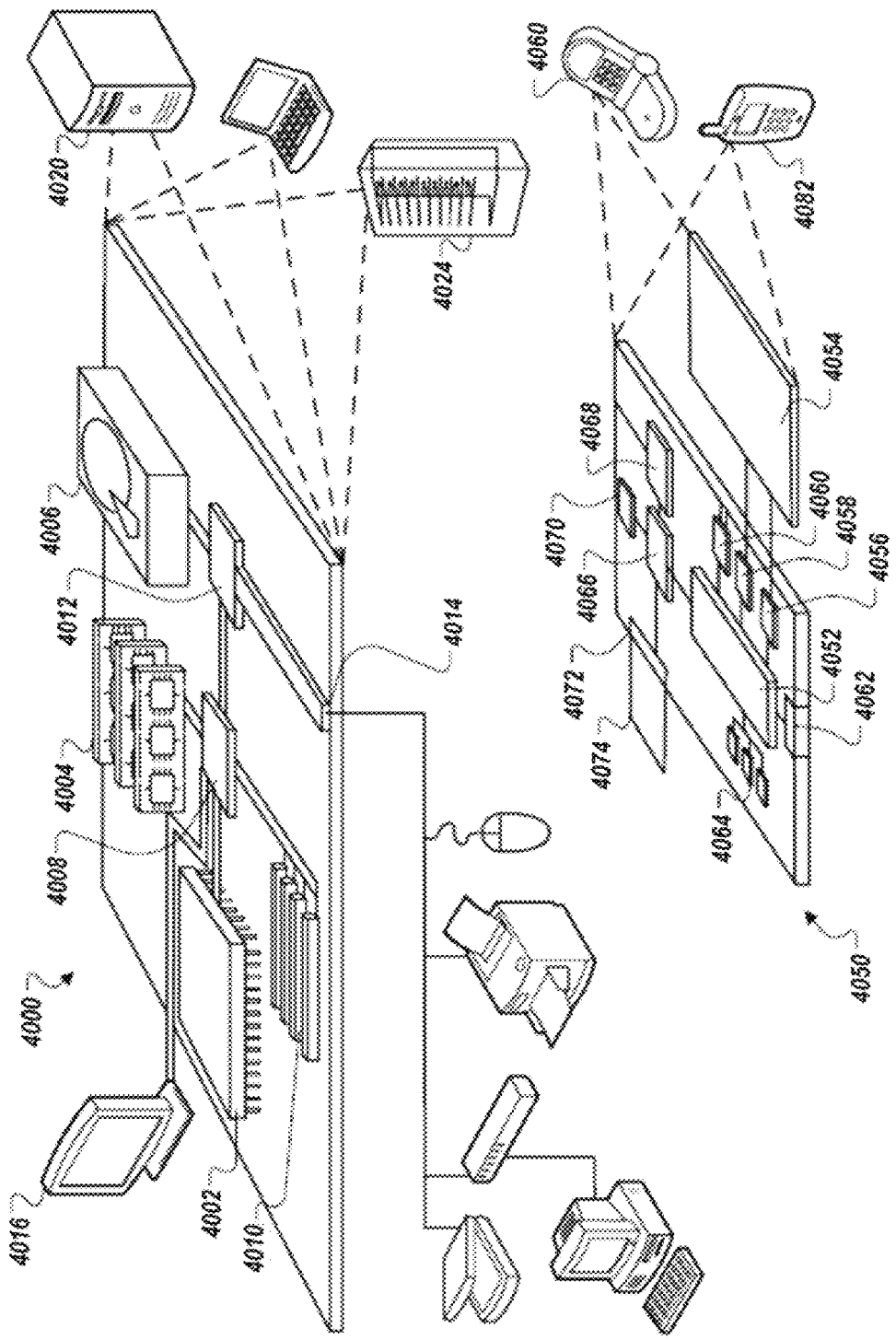
FIG. 40 is a block diagram of an example computing device and an example mobile computing device, for use in illustrative embodiments of the present disclosure.

FIG. 40 shows an example of a computing device 4000 and a mobile computing device 4050 that can be used in the methods and systems described in this disclosure. The computing device 4000 is intended to represent various forms of digital computers, such as laptops, desktops, workstations, personal digital assistants, servers, blade servers, mainframes, and other appropriate computers. The mobile computing device 4050 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 4000 includes a processor 4002, a memory 4004, a storage device 4006, a high-speed interface 4008 connecting to the memory 4004 and multiple high-speed expansion ports 4010, and a low-speed interface 4012 connecting to a low-speed expansion port 4014 and the storage device 4006. Each of the processor 4002, the memory 4004, the storage device 4006, the high-speed interface 4008, the high-speed expansion ports 4010, and the low-speed interface 4012, are interconnected using various busses, and may be mounted on a common motherboard or in other manners as appropriate. The processor 4002 can process instructions for execution within the computing device 4000, including instructions stored in the memory 4004 or on the storage device 4006 to display graphical information for a GUI on an external input/output device, such as a display 4016 coupled to the high-speed interface 4008. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (e.g., one or more processors) of any number of computing devices (e.g., one or more computing devices). Furthermore, where a function is described as being performed by "a processor", this encompasses embodiments wherein the function is performed by any number of processors (e.g., one or more processors) of any number of computing devices (e.g., one or more computing devices) (e.g., in a distributed computing system).

The memory 4004 stores information within the computing device 4000. In some implementations, the memory 4004 is a volatile memory unit or units. In some implementations, the memory 4004 is a non-volatile memory unit or units. The memory 4004 may also be another form of computer-readable medium, such as a magnetic or optical disk.

The storage device 4006 is capable of providing mass storage for the computing device 4000. In some implementations, the storage device 4006 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 4002), perform one or more methods, such as those described above. The instructions can also be stored by one or more storage devices such as computer- or machine-readable mediums (for example, the memory 4004, the storage device 4006, or memory on the processor 4002).

The high-speed interface 4008 manages bandwidth-intensive operations for the computing device 4000, while the low-speed interface 4012 manages lower bandwidth-intensive operations. Such allocation of functions is an example only. In some implementations, the high-speed interface 4008 is coupled to the memory 4004, the display 4016 (e.g., through a graphics processor or accelerator), and to the high-speed expansion ports 4010, which may accept various expansion cards (not shown). In the implementation, the low-speed interface 4012 is coupled to the storage device 4006 and the low-speed expansion port 4014. The low-speed expansion port 4014, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 4000 may be implemented in a number of different forms, as shown in the figure. For example, it may be implemented as a standard server 4020, or multiple times in a group of such servers. In addition, it may be implemented in a personal computer such as a laptop computer 4022. It may also be implemented as part of a rack server system 4024. Alternatively, components from the computing device 4000 may be combined with other components in a mobile device (not shown), such as a mobile computing device 4050. Each of such devices may contain one or more of the computing device 4000 and the mobile computing device 4050, and an entire system may be made up of multiple computing devices communicating with each other.

The mobile computing device 4050 includes a processor 4052, a memory 4064, an input/output device such as a display 4054, a communication interface 4066, and a transceiver 4068, among other components. The mobile computing device 4050 may also be provided with a storage device, such as a micro-drive or other device, to provide additional storage. Each of the processor 4052, the memory 4064, the display 4054, the communication interface 4066, and the transceiver 4068, are interconnected using various buses, and several of the components may be mounted on a common motherboard or in other manners as appropriate.

The processor 4052 can execute instructions within the mobile computing device 4050, including instructions stored in the memory 4064. The processor 4052 may be implemented as a chipset of chips that include separate and multiple analog and digital processors. The processor 4052 may provide, for example, for coordination of the other components of the mobile computing device 4050, such as control of user interfaces, applications run by the mobile computing device 4050, and wireless communication by the mobile computing device 4050.

The processor 4052 may communicate with a user through a control interface 4058 and a display interface 4056 coupled to the display 4054. The display 4054 may be, for example, a TFT (Thin-Film-Transistor Liquid Crystal Display) display or an OLED (Organic Light Emitting Diode) display, or other appropriate display technology. The display interface 4056 may comprise appropriate circuitry for driving the display 4054 to present graphical and other information to a user. The control interface 4058 may receive commands from a user and convert them for submission to the processor 4052. In addition, an external interface 4062 may provide communication with the processor 4052, so as to enable near area communication of the mobile computing device 4050 with other devices. The external interface 4062 may provide, for example, for wired communication in some implementations, or for wireless communication in other implementations, and multiple interfaces may also be used.

The memory 4064 stores information within the mobile computing device 4050. The memory 4064 can be implemented as one or more of a computer-readable medium or media, a volatile memory unit or units, or a non-volatile memory unit or units. An expansion memory 4074 may also be provided and connected to the mobile computing device 4050 through an expansion interface 4072, which may include, for example, a SIMM (Single In Line Memory Module) card interface. The expansion memory 4074 may provide extra storage space for the mobile computing device 4050, or may also store applications or other information for the mobile computing device 4050. Specifically, the expansion memory 4074 may include instructions to carry out or supplement the processes described above, and may include secure information also. Thus, for example, the expansion memory 4074 may be provided as a security module for the mobile computing device 4050, and may be programmed with instructions that permit secure use of the mobile computing device 4050. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 4052), perform one or more methods, such as those described above. The instructions can also be stored by one or more storage devices, such as one or more computer- or machine-readable mediums (for example, the memory 4064, the expansion memory 4074, or memory on the processor 4052). In some implementations, the instructions can be received in a propagated signal, for example, over the transceiver 4068 or the external interface 4062.

The mobile computing device 4050 may communicate wirelessly through the communication interface 4066, which may include digital signal processing circuitry where necessary. The communication interface 4066 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 4068 using a radio-frequency. In addition, short-range communication may occur, such as using a Bluetooth®, Wi-Fi™, or other such transceiver (not shown). In addition, a GPS (Global Positioning System) receiver module 4070 may provide additional navigation- and location-related wireless data to the mobile computing device 4050, which may be used as appropriate by applications running on the mobile computing device 4050.

The mobile computing device 4050 may also communicate audibly using an audio codec 4060, which may receive spoken information from a user and convert it to usable digital information. The audio codec 4060 may likewise generate audible sound for a user, such as through a speaker, e.g., in a handset of the mobile computing device 4050. Such sound may include sound from voice telephone calls, may include recorded sound (e.g., voice messages, music files, etc.) and may also include sound generated by applications operating on the mobile computing device 4050.

The mobile computing device 4050 may be implemented in a number of different forms, as shown in the figure. For example, it may be implemented as a cellular telephone 4080. It may also be implemented as part of a smart-phone 4082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Certain embodiments of the present disclosure were described above. It is, however, expressly noted that the present disclosure is not limited to those embodiments, but rather the intention is that additions and modifications to what was expressly described in the present disclosure are also included within the scope of the disclosure. Moreover, it is to be understood that the features of the various embodiments described in the present disclosure were not mutually exclusive and can exist in various combinations and permutations, even if such combinations or permutations were not made express, without departing from the spirit and scope of the disclosure. Having described certain implementations of systems and methods for imaging samples, it will now become apparent to one of skill in the art that other implementations incorporating the concepts of the disclosure may be used. Therefore, the claimed invention should not be limited to certain described embodiments, but rather should be limited only by the spirit and scope of the following claims.

The invention claimed is:

1. A method of imaging a sample using an array of micro optical elements, the method comprising:
   scanning the array of micro optical elements along a scan pattern defined by an array of sequential positions to generate an image of the sample, wherein the array of sequential positions is an M×N array, M and N are each no less than 10, and M≥N;
   wherein the image comprises tiles of pixels, the tiles each corresponding to a respective micro optical element in the array and the pixels each corresponding to a position in the array of sequential positions,
   wherein, for each pair of a first pixel in a first one of the tiles and a second pixel adjacent to the first pixel, the second pixel being in a different one of the tiles than the first one of the tiles, a position difference between the position corresponding to the first pixel and the position corresponding to the second pixel is less than (MN−2M+1).

2. The method of claim 1, wherein a position difference in the sequence of scan positions of a scan pattern between the position corresponding to the first pixel and the position corresponding to the second pixel is no more than (3M−3).

3. The method of claim 1, wherein a position difference in the sequence of scan positions of a scan pattern between the position corresponding to the first pixel and the position corresponding to the second pixel is no more than (2M−1).

4. The method of claim 1, wherein for each pair of adjacent pixels belonging to the same one tile, a position difference in the sequence of scan positions of a scan pattern between the position corresponding to the first pixel and the position corresponding to the second pixel is no more than (2M+2N−5).

5. The method of claim 1, wherein for each pair of adjacent pixels belonging to the same one tile, a position difference in the sequence of scan positions of a scan pattern between the position corresponding to the first pixel and the position corresponding to the second pixel is no more than (2M).

6. The method of claim 1, wherein for each pair of a first pixel in a first one of the tiles and a second pixel adjacent to the first pixel, the second pixel being in a different one of the tiles than the first one of the tiles, a position difference between the position corresponding to the first pixel and the position corresponding to the second pixel is less than 30% of the total number of scan positions in the scan pattern.

7. The method of claim 1, wherein for each pair of adjacent pixels belonging to the same one tile, a position difference between the position corresponding to the first pixel and the position corresponding to the second pixel is less than 30% of the total number of scan positions in the scan pattern.

8. The method of claim 1, wherein the array of sequential positions forms a spiral.

9. The method of claim 1, wherein the array of sequential positions is a regular array.

10. The method of claim 1, wherein the scan pattern has a size corresponding to a size of a unit cell of a micro optical element in the array of micro optical elements.

11. The method of claim 1, comprising, during the scanning, (i) providing illumination light to the sample through the micro optical elements and (ii) collecting corresponding back-emitted light from the sample with the micro optical elements that is subsequently received at a detector.

12. The method of claim 11, comprising generating, by a processor of a computing device, the image of the sample based on the corresponding back-emitted light received at the detector.

13. The method of claim 1, wherein the series of sequential positions comprises a series of sequential rows of positions, wherein each of the sequential rows in the series is temporally separated from its spatially adjacent rows in the series by no more than two rows in the series.

14. The method of claim 13, wherein a starting position of the scan pattern is in an interior one of the sequential rows of positions and a final position of the scan pattern is in an exterior one of the sequential rows of positions.

15. The method of claim 14, wherein each row in the series of sequential rows of positions is no closer to the interior one of the sequential rows of positions than an immediately preceding row in the series of sequential rows of positions.

16. The method of claim 13, wherein a starting position of the scan pattern is in an exterior one of the sequential rows of positions and a final position of the scan pattern is in an interior one of the sequential rows of positions.

17. The method of claim 16, wherein each row in the series of sequential rows of positions is no further from the interior one of the sequential rows of positions than an immediately preceding row in the series of sequential rows of positions.

18. The method of claim 13, wherein the scan pattern is unidirectional.

19. The method of claim 13, wherein the scan pattern is bidirectional.

* * * * *

UNITED STATES PATENT AND TRADEMARK OFFICE
CERTIFICATE OF CORRECTION

Page 1 of 1

PATENT NO. : 12,236,603 B2
APPLICATION NO. : 17/174919
DATED : February 25, 2025
INVENTOR(S) : Andrey Naumenko et al.

It is certified that error appears in the above-identified patent and that said Letters Patent is hereby corrected as shown below:

In the Specification

Column 22, Line 37:
Please replace "5A" with --1A--

Column 22, Line 42:
Please replace "5B" with --1B--

Signed and Sealed this
Twenty-seventh Day of January, 2026

John A. Squires
*Director of the United States Patent and Trademark Office*